US012723112B2

(12) United States Patent
Alexanian et al.

(10) Patent No.: US 12,723,112 B2
(45) Date of Patent: Sep. 1, 2026

(54) REAGENTS AND METHODS FOR ALIPHATIC CARBON-HYDROGEN BOND FUNCTIONALIZATION

(71) Applicant: THE UNIVERSITY OF NORTH CAROLINA AT CHAPEL HILL, Chapel Hill, NC (US)

(72) Inventors: Erik Alexanian, Chapel Hill, NC (US); Jill Alty, Chapel Hill, NC (US); Timothy Fazekas, Chapel Hill, NC (US); Frank Leibfarth, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 18/560,665

(22) PCT Filed: May 12, 2022

(86) PCT No.: PCT/US2022/029013
§ 371 (c)(1),
(2) Date: Nov. 13, 2023

(87) PCT Pub. No.: WO2022/241129
PCT Pub. Date: Nov. 17, 2022

(65) Prior Publication Data

US 2024/0336711 A1 Oct. 10, 2024

Related U.S. Application Data

(60) Provisional application No. 63/188,215, filed on May 13, 2021.

(51) Int. Cl.
*C08F 8/30* (2006.01)
*C07C 259/10* (2006.01)
*C08F 8/32* (2006.01)

(52) U.S. Cl.
CPC ............. *C08F 8/32* (2013.01); *C07C 259/10* (2013.01)

(58) Field of Classification Search
CPC ........................................................ C08F 8/30
See application file for complete search history.

(56) References Cited

FOREIGN PATENT DOCUMENTS

WO WO 2014/210270 12/2014

OTHER PUBLICATIONS

Miller, Austin, et al. "Diversification of aliphatic C—H bonds in small molecules and polyolefins through radical chain transfer." Science. (Feb. 4, 2022), 375, pp. 545-550. (Year: 2022).*

Chen et al., "Methanol-assisted phthalimide ring opening: concerted or stepwise mechanism?," The Journal of Physical Chemistry A, 122(12):3115-3119, (2018).

Davies et al., "Recent advances in C—H functionalization," The Journal of Organic Chemistry, 81(2):343-350, (2016).

Margrey et al., "A general strategy for aliphatic C—H functionalization enabled by organic photoredox catalysis," Journal of the American Chemical Society, 140(12):4213-4217, (2018).

Phipps et al., "Rh (III)-catalyzed C—H activation-initiated directed cyclopropanation of allylic alcohols," Journal of the American Chemical Society, 141(17):6807-6811, (2019).

WIPO Application No. PCT/US2022/029013, PCT International Search Report and Written Opinion of the International Searching Authority mailed Sep. 1, 2022.

* cited by examiner

*Primary Examiner* — John S Kenyon
(74) *Attorney, Agent, or Firm* — Alston & Bird LLP

(57) ABSTRACT

The subject matter contained herein relates generally to methods and compounds that facilitate aliphatic carbon-hydrogen bond functionalization by group transfer via a nitrogen-centered radical in the presence of a trap, and the functionalized compounds prepared therefrom. The subject matter described herein provides a platform and the ability to efficiently and selectively introduce a range of valuable functionality on diverse hydrocarbon substrates ranging from methane to polyolefins with >3500 carbon atoms. As described herein, the reagents employed can form reactive N-centered radicals, the kinetics of which do not compete with companion radical traps. This technology finds usefulness in enhancing capabilities in late-stage diversification, while the molecules and materials now made accessible can provide solutions to important challenges in medicinal chemistry and materials science.

19 Claims, 21 Drawing Sheets

C.

B.

C.

B.

LLDPE

P21
5 mol %

P22
4 mol %

C.

| | LLDPE | Polyolefin Ionomer |
|---|---|---|
| $\sigma_B$ (MPa) | 13 ± 1 | 15 ± 1 |
| $\varepsilon_B$ | 250 ± 51% | 675 ± 69% |
| E (MPa) | 27 ± 2 | 1.9 ± 0.2 |
| $U_T$ (MPa) | 387 ± 74 | 696 ± 49 |

REAGENTS AND METHODS FOR ALIPHATIC CARBON-HYDROGEN BOND FUNCTIONALIZATION

RELATED APPLICATIONS AND INCORPORATION BY REFERENCE

This application is the national phase entry of International Application No. PCT/US22/29013 filed May 12, 2022, which claims the benefit of U.S. Provisional Application No. 63/188,215 filed May 13, 2021, which is herein incorporated by reference in its entirety for all purposes.

STATEMENT OF GOVERNMENT SUPPORT

This invention was made with government support under Grant No. GM131708 awarded by National Institutes of Health and Grant No. FA9550-18-1-0085 awarded by Air Force Office of Scientific Research. The government has certain rights in the invention.

FIELD OF THE INVENTION

The subject matter contained herein relates generally to methods and compounds that facilitate aliphatic carbon-hydrogen bond functionalization by group transfer via a nitrogen-centered radical in the presence of a trap, and the functionalized compounds prepared therefrom.

BACKGROUND

Unactivated carbon-hydrogen (C—H) bond functionalization is useful in chemical synthesis, enabling an array of new approaches in the synthesis and late-stage derivatization of complex molecules. In drug discovery and development, C—H functionalization offers the ability to facilitate the preparation of structural analogs of drugs with enhanced structure-activity relationships (SAR) or other desired physicochemical properties. Owing to the plethora of different C—H bonds present in most organic molecules, great effort has been devoted to the site-selective and predictable functionalization of C—H bonds in complex targets. While the number and diversity of the above mentioned different C—H bonds may render a single synthetic approach impractical, there remains a need for methods and reagents capable of aliphatic carbon-hydrogen bond functionalization via radical chain transfer.

The ability to selectively introduce diverse functionality to hydrocarbons is of significant value in the synthesis of both small molecules and polymers. There remains a lack of simple methods that enable the efficient and broad diversification of unactivated aliphatic C—H bonds. The subject matter described herein addresses the shortcomings in this field.

BRIEF SUMMARY

In certain embodiments, the subject matter described herein is directed to a compound of Formula I:

I

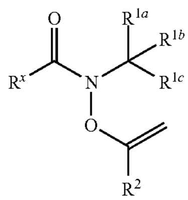

wherein, $R^x$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$; or, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$.

In certain embodiments, the subject matter described herein is directed to a compound having a structure of Formula II:

II

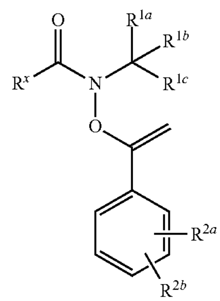

wherein, $R^{2a}$ and $R^{2b}$ are each independently selected from the group consisting of hydrogen, halo, optionally substituted linear or branched $C_{1-10}$ alkyl, —CN, $C_{1-6}$ alkoxy, —$NO_2$, —$NR^aR^b$, —(C═O)$OR^c$ and —(C═O)$R^c$, wherein, $R^a$, $R^b$ and $R^c$ are each independently selected from the group consisting of hydrogen, methyl, ethyl, propyl and butyl.

In certain embodiments, the subject matter described herein is directed to a compound having a structure of Formula III:

III

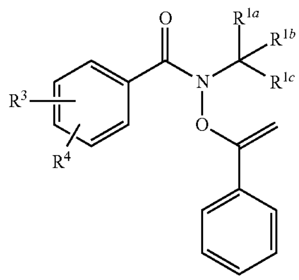

wherein, $R^3$ and $R^4$ are each independently selected from the group consisting of halo-$C_{14}$ alkyl, halo, —CN, and —$NO_2$.

In certain embodiments, the subject matter described herein is directed to a mixture comprising:

a solvent;

a compound of Formula I:

I

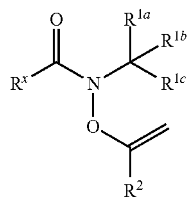

wherein, $R^x$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$; or, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$ and, at least one of the following:

i. a compound of Formula T-A:

T-A

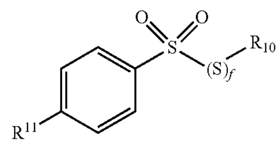

wherein, $R^{11}$ is selected from the group consisting of hydrogen, halo, halo-$C_{1-6}$ alkyl, —CN, $C_{1-6}$ alkyl and $C_{1-6}$ alkoxy;

f is 0 or 1;

$R^{10}$, when f is 1, is selected from the group consisting of halo-$C_{1-6}$ alkyl, and optionally substituted $C_{6-10}$ aryl; or $R^{10}$, when f is 0, is selected from the group consisting of —CN and —$N_3$;

or, i(a). a compound of Formula T-A1:

T-A1

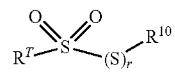

wherein, $R^T$ is selected from the group consisting of $C_{1-6}$ alkyl and $C_{6-10}$ aryl, wherein the $C_{6-10}$ aryl is optionally substituted with $R^{11}$;

$R^{11}$ is selected from the group consisting of hydrogen, phenyl, halo, —C(O)O—$C_{1-6}$ alkyl, halo-$C_{1-6}$ alkyl, —CN, $C_{14}$ alkyl and $C_{1-6}$ alkoxy;

f is 0 or 1;

$R^{10}$ is a moiety that along with —$(S)_f$— is an X moiety for transferring and binding to a carbon on a substrate;

or, ii. an external trap as shown in Table 1;

or, iii. a radical trap comprising an X moiety for transferring and binding to a carbon on a substrate.

In certain embodiments, the subject matter described herein is directed to a method of functionalizing a substrate, comprising:

i. in the presence of a radical trap comprising a transfer group X and the substrate, wherein the substrate comprises a C—H bond, allowing a compound of Formula I:

I

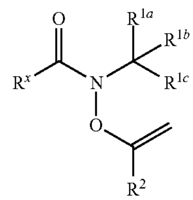

wherein, $R^x$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$; or, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

and $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$; to contact an initiator to form a nitrogen-centered radical;

ii. allowing the substrate comprising a C—H bond to contact the nitrogen-centered radical to form a substrate radical;

iii. allowing the substrate radical to contact the radical trap comprising a transfer group X, wherein, a C—H bond in the substrate is functionalized to a covalent C—X bond, wherein X is the transfer group.

Still further embodiments are as described herein.

DETAILED DESCRIPTION

The ability to selectively introduce diverse functionality to hydrocarbons is of significant value in the synthesis of both small molecules and polymers. There remains a lack of simple methods that enable the efficient and broad diversification of unactivated aliphatic C—H bonds. The subject matter described herein provides a platform and the ability to efficiently and selectively introduce a range of valuable functionality on diverse hydrocarbon substrates ranging from methane to polyolefins with >3500 carbon atoms. As described herein, the reagents employed can form reactive N-centered radicals, the kinetics of which do not compete with companion radical traps. This technology finds usefulness in enhancing capabilities in late-stage diversification, while the molecules and materials now made accessible can provide solutions to important challenges in medicinal chemistry and materials science.

In one aspect, the subject matter herein describes an approach to aliphatic C—H diversification via radical chain transfer featuring a readily prepared O-alkenylhydroxamate reagent, which upon mild heating facilitates a range of challenging or previously undeveloped aliphatic C—H functionalizations of small molecules and polyolefins. Applications ranging from the late-stage diversification of complex small molecules to the modification of the physical properties of post-consumer waste highlight the versatility and broad generality of this strategy. Also described herein are reagents that enable the broad diversification/functionalization of unactivated, aliphatic C—H bonds in compounds, such as small molecules and polymers.

Figure 1A:
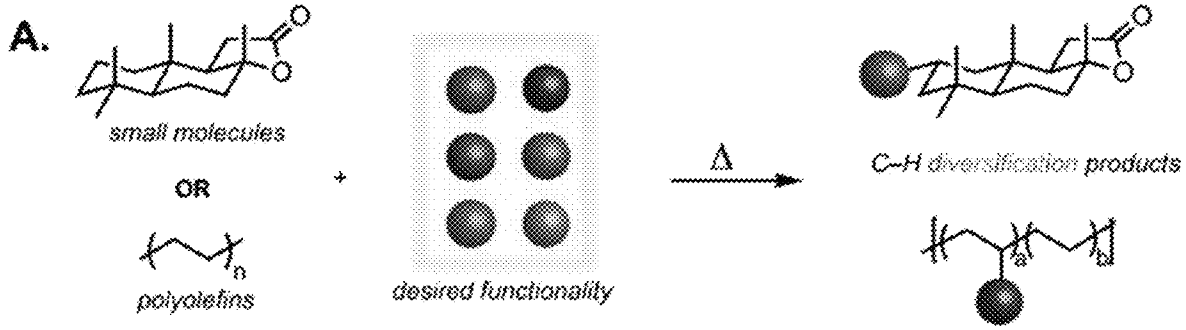
FIG. 1 depicts aliphatic C—H diversification using N-functionalized amides. (A) A universal approach to C—H functionalization would place varied functionality selectively onto small molecules and commodity polyolefins. (B) This work uses an N-functionalized amide and a diverse set of chain transfer agents to achieve C—H diversification. (C) The mechanistic hypothesis for C—H diversification using O-alkenylhydroxamates. Ar=3,5-bis(trifluoromethyl)phenyl.

The direct transformation of unreactive aliphatic C—H bonds to useful functionality can be a streamlined and sustainable approach to accessing complex molecules and materials with enhanced properties from readily available compounds (1-4). However, it is an approach that is not being utilized to its full potential at present. The concept of late-stage diversification of drug-like molecules, wherein complex substrates are modified selectively to alter their function, has emerged as a powerful strategy to access new lead compounds for medicinal chemistry and structure-activity relationship (SAR) studies without resorting to de novo synthesis (5). The broad impact of late-stage diversification extends from such small molecule contexts to the end-of-life fate of plastic waste, where an estimated 95% of the economic value of plastics is lost after a single use (6). Selective C—H functionalization of post-consumer plastic has the potential to differentiate its properties and enhance its value, thus contributing to a more sustainable plastics economy (7, 8). Currently, a number of transformations of aliphatic C—H bonds exist and are used for the late-stage diversification of drug-like molecules and commodity polymers, but the vast majority of these use either nearby directing groups to control reaction site selectivity or involve promiscuous reactive intermediates which significantly limit the scope of these approaches (9, 10). A universal strategy for aliphatic C—H functionalization, wherein a wide array of functionality can be placed site-selectively in an intermolecular transformation on both complex organic substrates and commodity polymers, remains a significant challenge (FIG. 1A) (11).

Efficient C—H functionalizations that occur under mild conditions and use substrate as the limiting reagent—an essential requirement to applications in medicinal chemistry and polymer functionalization—remain scarce. A notable exception is the use of high-valent transition metal-oxo complexes in aliphatic C—H functionalization, but this approach is limited by the scope of accessible transformations owing to the use of highly oxidizing intermediates (12, 13). Intermolecular alkylation of C—H bonds using rhodium catalysis is also well-developed, but the requirement for donor-acceptor diazo reagents significantly limits overall scope, and the use of a precious metal limits high-volume applications in polymer science (14). Furthermore, several valuable C—H transformations, such as aliphatic C—H iodination and C—H methylation, remain limited regardless of approach.

Recent studies have demonstrated the utility of heteroatom-centered radicals to facilitate site-selective, intermolecular functionalizations of unactivated aliphatic C—H bonds on a variety of small molecules and materials, constituting a complementary strategy to metal-catalyzed methods (15-20). These reactions principally harness the ability of a tuned nitrogen-centered radical to achieve facile hydrogen atom transfer (HAT) from strong, unactivated aliphatic C—H sites. A critical drawback to these previous studies is the requirement for direct group transfer of the functionality appended to nitrogen, which greatly restricts the diversity of products accessible via the HAT platform.

Figure 1B:
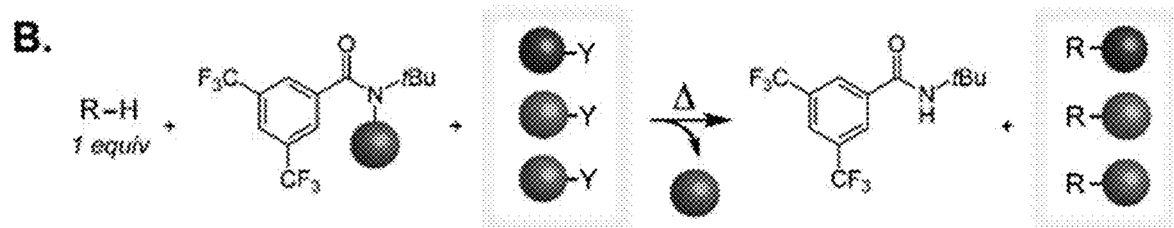
Figure 1C:
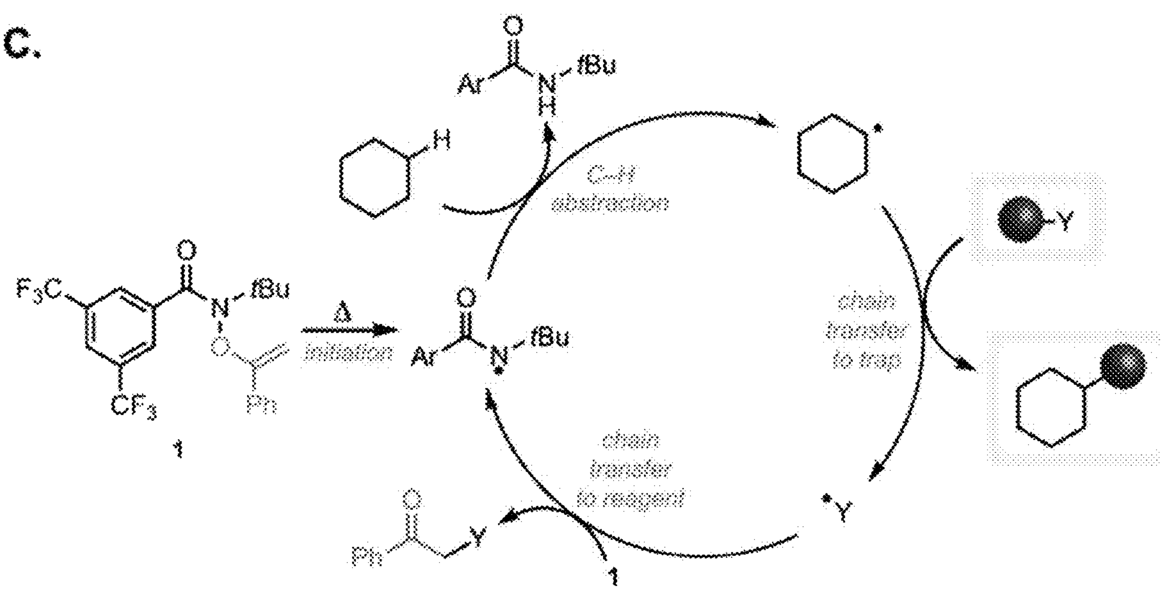

Described herein is a new approach. It involves decoupling the formation of the nitrogen-centered radical responsible for HAT from the chain transfer step to unlock a universal C—H diversification manifold applicable to a vast range of transformations (FIG. 1B). The reagents described herein, with just one example being an O-alkenylhydroxamate (1), are capable of forming reactive nitrogen-centered radicals, but whose chain transfer kinetics allows external radical traps to outcompete it for substrate functionalization (FIG. 1C). Such a versatile C—H diversification strategy would encompass many important transformations, including ones inaccessible with current synthetic technology, and extend to areas ranging from the late-stage C—H diversification of complex molecules to applications in the transformation of post-consumer plastic waste to functional polyolefins.

Described herein are reagents and method to apply the intermolecular, aliphatic C—H diversification to a range of small molecules and polyolefins (Table 1). Any polyolefin known in the art can be a useful substrate and includes those described elsewhere herein and as a non-limiting example, poly(norbornenes). The results of the studies demonstrate the versatility of easily accessed, shelf-stable O-alkenylhydroxamate 1 in these transformations. Notably, the C—H functionalizations promoted by reagent 1 proceeded simply upon mild heating (70° C.) or visible light irradiation without the need for an exogenous initiator, which is an enabling aspect of the approach. The C—H diversification of cyclooctane with substrate as limiting reagent was successful using 10 diverse trapping agents in good to excellent yield, establishing the broad scope of the platform (2-11).

This includes the first example of a practical intermolecular, aliphatic C—H iodination, which sets the stage for a range of challenging C—H transformations (vide infra) (21). While there are extant methods available for a subset of these reactions, examples using substrate as limiting reagent remain quite rare. Also, it is common that the alkane would need to be present in large relative excess (>5 equiv) and often times as reaction solvent. Furthermore, there are no platforms for aliphatic C—H functionalization that provide the synthetic scope demonstrated herein with respect to both the diversity of accessible transformations and the viable substrates ranging from small molecules to post-consumer waste. While the present data show many synthetically valuable C—H transformations, additional processes are contemplated based upon the use of alternative radical traps.

TABLE 1

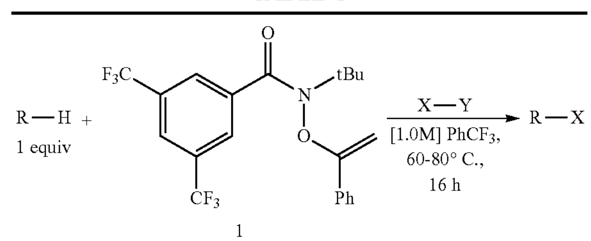

1

External Traps (X-Y):

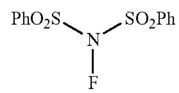

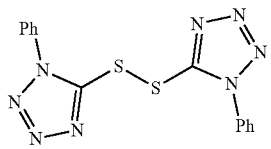 [SMILES: c1ccc(-n2nnnc2SSc2nnnn2-c2ccccc2)cc1]

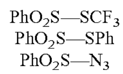

$PhO_2S—SCF_3$
$PhO_2S—SPh$
$PhO_2S—N_3$

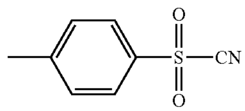

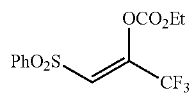

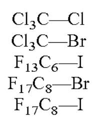

$Cl_3C—Cl$
$Cl_3C—Br$
$F_{13}C_6—I$
$F_{17}C_8—Br$
$F_{17}C_8—I$

Small Molecule Substrates

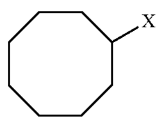

X = F (2): 77% yield
Cl (3): 63% yield
Br (4): 62% yield
I (5): 70% yield

TABLE 1-continued

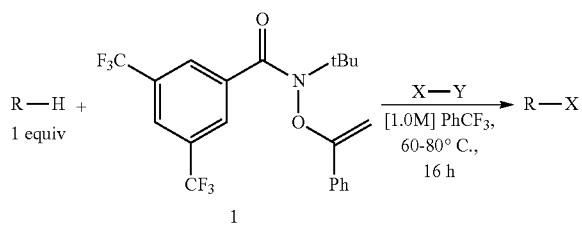

1

$SCF_3$ (7): 76% yield
SPh (8): 44% yield
$N_3$ (9): 84% yield
CN (10): >95% yield

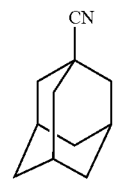 [SMILES: N#CC12CC3CC(CC(C3)C1)C2]

12
64% yield

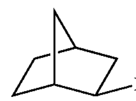

13
56% yield

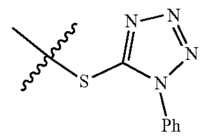 [SMILES: *Sc1nnnn1-c1ccccc1]

(6): 78% yield

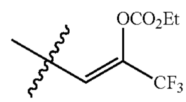

(11): 70% yield

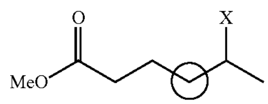

F (23): 52% yield
I (24): 49% yield

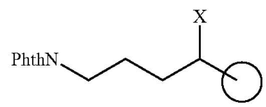

Cl (25): 66% yield
I (26): 53% yield

TABLE 1-continued
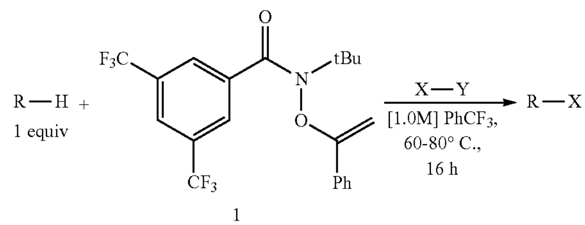
1
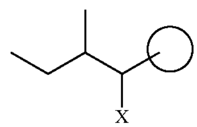
Cl (14): 64% yield
Br (15): 62% yield
I (16): 54% yield
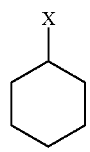
F (17): 50% yield
I (18): 63% yield
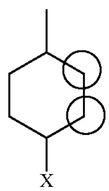
Cl (19): 56% yield
Br (20): 76% yield
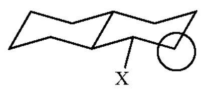
F (21): 50% yield
$N_3$ (22): 50% yield
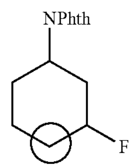
27
70% yield
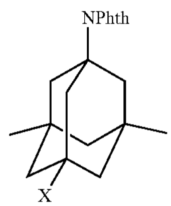
F (28): 68% yield
$SCF_3$ (29): >95% yield
TABLE 1-continued
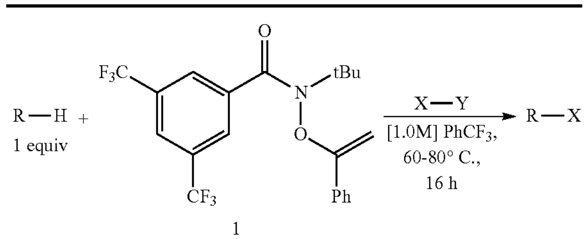
1
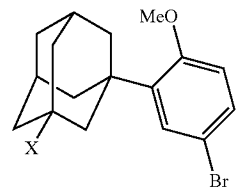
F (30): 72% yield
I (31): >95% yield
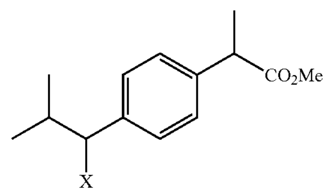
ibuprofen methyl ester
F (32): 67% yield
$SCF_3$ (33): 48% yield
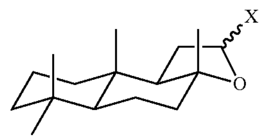
(−)-ambroxide
CN (34): 84% yield
$N_3$ (35): 56% yield
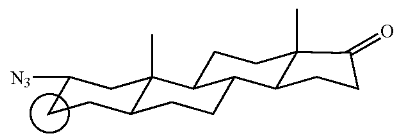
deoxyandrosterone
36
70% yield
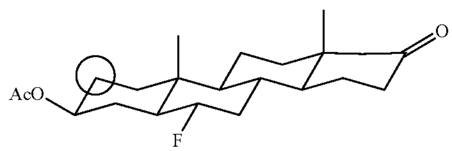
trans-androsterone acetate
37
47% yield TABLE 1-continued

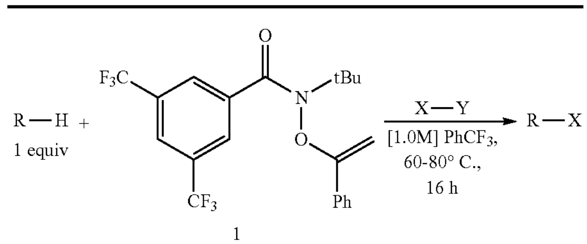

1

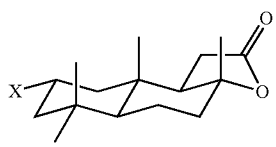

(+)-sclareolide
F (38): 74% yield
I (39): >95% yield
Cl (40): >95% yield
Br (41): 90% yield
$SCF_3$ (42): 85% yield
$N_3$ (43): 76% yield
SPT (44): 74% yield Polyolefin Substrates

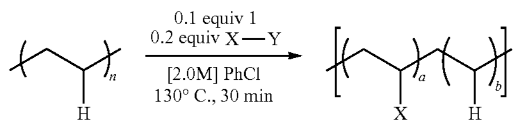

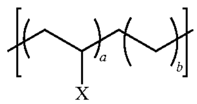

high density PE (HDPE)
X =
CN (P9): 3 mol %
I (P10): 2 mol %
SPh (P11): 8 mol %

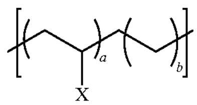

low density PE (LDPE)
X =
CN (P12): 5 mol %
I (P13): 3 mol %
SPh (P14): 6 mol %

TABLE 1-continued

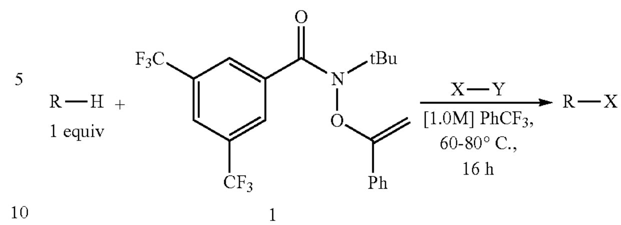

1

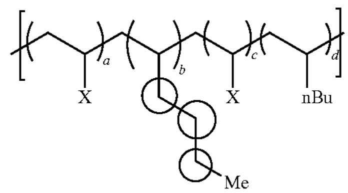

linear low density PE (LLDPE)
X =
F (P1): 5 mol %
Br (P2): 4 mol %
I (P3): 4 mol %
$SCF_3$ (P4): 3 mol %
SPh (P5): 7 mol %
$N_3$ (P6): 4 mol %
CN (P7): 6 mol %
SPT (P8): 2 mol %

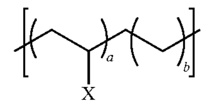

+ other polymers/additives
post-industrial PE (PIPE)
X =
CN (P15): 5 mol %
I (P16): 4 mol %
SPh (P17): 6 mol %
post-consumer PE (PCPE)
X =
CN (P18): 6 mol %
I (P19): 3 mol %
SPh (P20): 6 mol %

The C—H diversification was applied to several representative small molecule substrates. Diverse cyclic and linear hydrocarbons react efficiently using substrate as limiting reagent (12-22). The sterically-dictated site selectivities controlled by the bulky N-tBu amidyl radical favor accessible secondary C—H sites over weaker, tertiary C—H bonds which are commonly the most reactive in C—H functionalizations, unlocking new aliphatic sites for C—H diversification (14-16, 19-22). Functionalized substrates containing electron-withdrawing groups (23-27) exhibit strong polar effects in discriminating between methylene sites, with sites distal to the electron-withdrawing group preferred (22). The notable sterically- and electronically-dictated site selectivities characteristic of this platform, when combined with the breadth of accessible C—H transformations, enable a wealth of valuable late-stage diversifications of complex molecules as described below.

The data herein show the C—H functionalization of several representative natural products and drug derivatives to highlight the scope of this approach. The reactions of adamantyl substrates were highly efficient, providing products 28-31 in excellent yields. The benzylic functionalization of ibuprofen methyl ester provided fluorination and trifluoromethylthiolation products 32 and 33, respectively, as single regioisomers in contrast to previous C—H functionalizations of this substrate (23). Several terpenoid and steroid natural products were also examined, supporting the ability to selectively functionalize complex molecules with a multitude of aliphatic C—H sites. The functionalization of (−)-ambroxide favors the activated C—H site a to the ether oxygen atom (34-35). The fully saturated steroid deoxyandrosterone was azidated in good yield (70%) favoring the C2 position of the A-ring (36). With an electron-withdrawing acetate group present in the A-ring of related substrate trans-androsterone acetate, C—H fluorination proceeded in 47% combined yield, with a single diastereomer of a B-ring fluoride produced with 72% site selectivity (37). For comparison, a previous C—H fluorination of this substrate with Selectfluor yielded greater than seven alkyl fluorides, with none formed in greater than 6% yield (24). Additionally, described herein are several C—H functionalizations of the terpenoid natural product (+)-sclareolide, favoring the most reactive A-ring methylene site (38-44, for reaction optimization studies see Table S1). In each case, a single regioisomer was obtained in good to excellent yield with high (>10:1) diastereoselectivity, including the C—H iodination which delivers iodide 39 in virtually quantitative yield. Notably, the fluorination (74%) and trifluoromethylthiolation (85%) of (+)-sclareolide proceeded with similarly excellent selectivity.

Importantly, while previous studies have reported C—H functionalizations providing access to these two specific products, in all cases more than one regioisomer was observed, with multiple diastereomers formed from each site. The present platform utilizing the reagents and methods described herein thus offers a powerful tool for the late-stage introduction of fluorinated groups at unactivated aliphatic sites in complex molecules for modulating the absorption, distribution, metabolism, and excretion (ADME) properties of drug-like compounds.

Another aspect of this technology concerns its use for C—H diversification and the efficient installation of a range of functionality onto branched polyolefins, which represent >35% of polymers produced worldwide (25). Branched polyolefins typically undergo deleterious chain scission events during mechanical reprocessing or polymer functionalization (26), which degrades their thermomechanical properties and contributes to their poor recycling rate (<5% in the US) (23).

Without being bound to theory, it could be that the regioselective reactions of 1 at methyl or methylene sites would prevent polymer chain-scission by eliminating the formation of tertiary radicals during reactive processing and enable access to a range of branched polyolefins with polar functionality. Such polar polyolefins, which are inaccessible using traditional Ziegler-Natta or metallocene catalysis, enhance interfacial adhesion and provide sites for controlled polymer deconstruction (27). LLDPE (Dow DNDA-1081) was chosen as a model branched polyolefin to exemplify this method (melting temperature of 122° C.; 19 branches per 100 carbons). As a representative transformation to introduce polar functionality incompatible with early transition metal catalysts, cyanation of LLDPE with 1 under homogeneous conditions (130° C. in chlorobenzene) proceeded efficiently with selectivity for methylene sites and involved no discernable chain-scission as confirmed by size exclusion chromatography (SEC) as well as a variety of 1D and 2D NMR techniques. In contrast, an analogous cyanation using dicumyl peroxide as a radical initiator in place of 1 yielded no functionalization and a decrease in polymer molecular weight. All polymer functionalizations target a maximum of 10 mol % repeat-unit modification in order to add functionality while maintaining the beneficial semicrystalline nature of the material.

In addition to polyolefin cyanation, the installations of fluoride, bromide, iodide, trifluoromethylthiol, thiophenyl, azido, and (phenyltetrazole)thiol groups onto LLDPE exemplified the versatility of this approach. Several of these polyolefin C—H transformations are without precedent and deliver novel products inaccessible by other means (18, 19, 28, 29). To further extend the scope, C—H cyanation, thiophenylation, and iodination were successful on complementary substrates, including highly crystalline high-density PE (HDPE), highly branched LDPE (49 branches per 100 carbons), post-industrial waste PE (PIPE, 5 branches per 100 carbons) remnants from packaging forms, and post-consumer waste PE (PCPE, 4 branches per 100 carbons) obtained from PE foam packaging. Functionalization proceeded efficiently even with an undefined mix of additives in PCPE evident by IR and $^1$H NMR spectroscopy, indicating the tolerance of this method to common impurities in plastic waste.

Figure 2A:
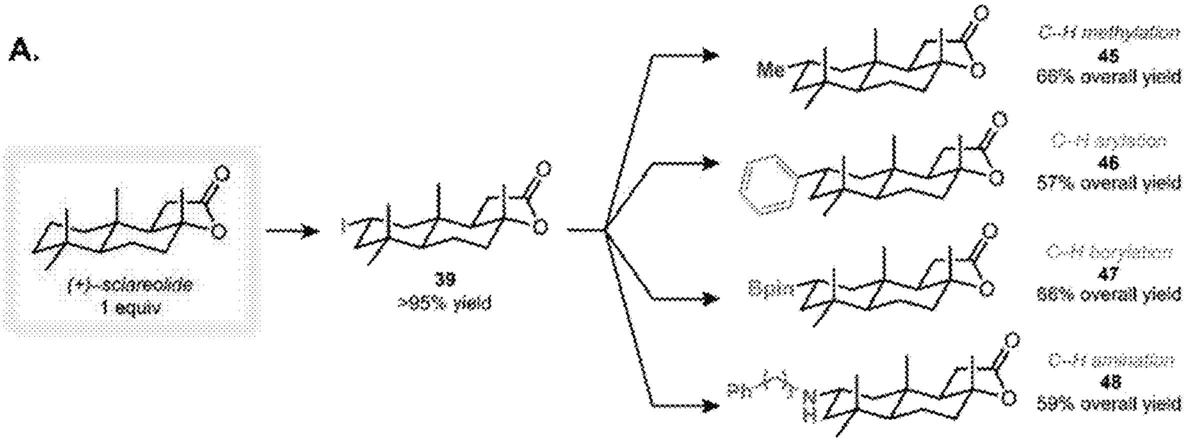
FIG. 2 depicts aliphatic C—H diversifications enabled by the platform described herein. (A) C—H transformations enabled by C—H iodination. See Supporting Information for reaction details. (B) C—H (phenyltetrazole)thiolation of methane. (C) Determination of the kinetic isotope effect of reactions involving reagent 1.

As shown herein, the synthetic capabilities of this platform unlock hydrocarbon C—H functionalizations which remain a major challenge. With respect to late-stage diversification, the broad scope enables valuable, yet rare, C—H transformations. For example, the late-stage, intermolecular methylation of unactivated aliphatic C—H bonds represents a desirable tool in medicinal chemistry owing to the significant potential for modulating biological properties via the "magic methyl" effect, yet this transformation remains limited to sites a to heteroatomic functionality (30, 31). In an aspect, what is contemplated and described herein is a simple, scalable approach to the formal methylation of unactivated aliphatic C—H bonds via a two-step protocol (FIG. 2A). Following the highly efficient iodination of sclareolide (>95% yield), reaction with $Me_2CuLi$ delivers the formal C—H methylation product 45 in good yield as a single diastereomer. Alternatively, iron-catalyzed cross-coupling of 39 with PhMgBr leads to the C—H arylation product 46; previous C—H arylation of this substrate required the use of superstoichiometric amounts of (+)-sclareolide (32). The borylation of unactivated, aliphatic C—H bonds is another transformation with very limited precedent using substrate as limiting reagent (33, 34). Facile borylation of 39 using $B_2cat_2$ followed by transesterification yielded 47 as a single product in 66% overall yield (35). Finally, the copper-catalyzed cross-coupling of 39 with a primary alkyl amine delivered C—H amination product 48 in good yield (36). This constitutes a formal dehydrogenative alkane-amine coupling and is a modular approach to C—H amination that complements catalytic systems involving metal nitrenoids. Other attractive C—H transformations are also easily envisioned capitalizing on the versatility of the phenyltetrazole sulfone group which can be easily accessed from product 44 (37).

Figure 2B:
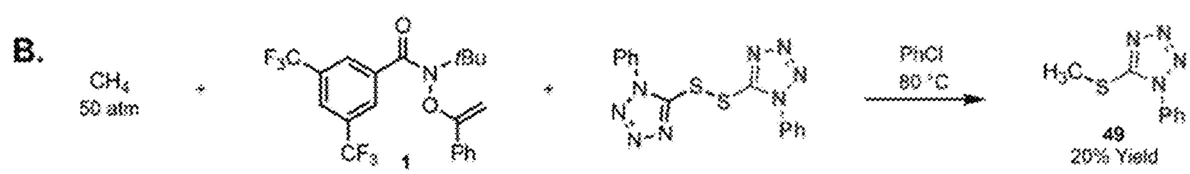
Figure 2C:
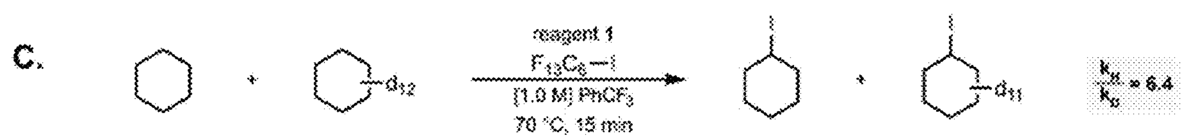

The transformation of the unreactive C—H bond of gaseous methane remains a considerable challenge for any C—H functionalization. The strong N—H bond (110.7 kcal/mol) of the parent amide of 1 suggested that methane HAT (C—H bond ~105 kcal/mol) could be viable (38). As a demonstration of the notable reactivity of the amidyl radical in HAT, we successfully performed the (phenyltetrazole)thiolation of methane under our standard conditions to deliver 49 in 20% yield with respect to 1 (FIG. 2B). In further support of an irreversible aliphatic C—H HAT in reactions involving 1, a C—H iodination competition experiment between cyclohexane and $d_{12}$-cyclohexane proceeded with a $k_H/k_D$ of 6.4 (FIG. 2C). Additionally, the C—H (phenyltetrazole)thiolation reaction produces the a-SPT acetophenone byproduct, consistent with the chain-transfer mechanism outlined in FIG. 1C.

The late-stage introduction of diverse heterocycles onto complex small molecules enables efficient access to new medicinally relevant compounds. An attractive approach to such a transformation would utilize the ubiquitous aliphatic C—H bonds of a complex substrate. Herein, we report a system that enables direct C—H heteroarylation using a stable, commercially available O-alkenylhydroxamate with heterocyclic sulfonate partners. The C—H heteroarylation proceeds efficiently in the coupling of a range of aliphatic substrates and common heterocycles and is a rare example of heteroarylation of strong C—H bonds. Importantly, the present approach is amenable to late-stage functionalization as substrate is limiting in all cases. Described herein is a practical approach to the C—H heteroarylation of unactivated aliphatic C—H bonds using easily accessed heteroaryl sulfones and a commercially available O-alkenylhydroxamate reagent. Many synthetically and medicinally relevant heteroarenes are viable coupling partners, providing a broad platform for molecular diversification. Importantly, the present subject matter describes methods that can use substrate as limiting reagent in any case, which can be essential to applications in the LSF of complex molecules. The reactions proceed with good levels of site selectivity, characteristic of the aliphatic C—H functionalization platform proceeding via the amidyl radicals.

Figure 3A:
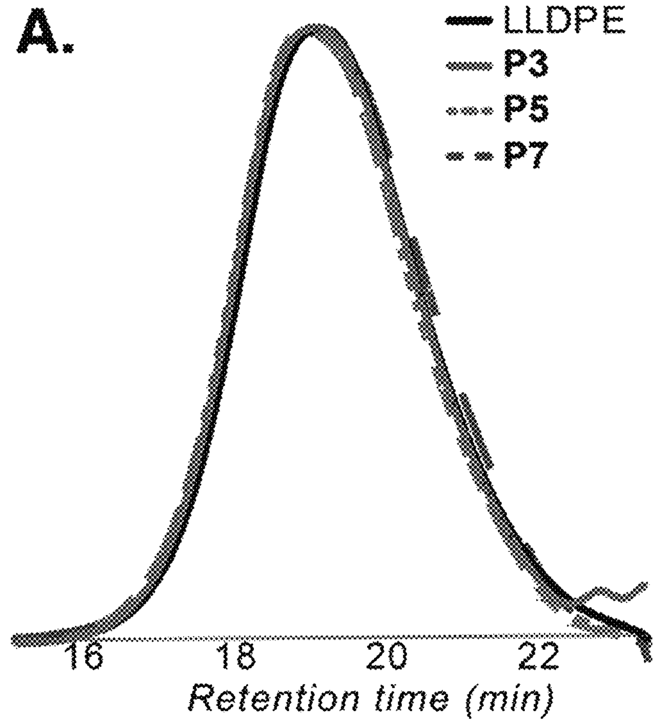
FIG. 3 depicts access to polyolefin ionomers through C—H functionalization using the reagents and processes described herein. (A) Size exclusion chromatography comparing commercial LLDPE to functionalized derivatives thereof. (B) Polyolefin C—H functionalization enabled the production of ionomers from commercial plastics in a two-step approach. (C) Tensile tests demonstrate the change in polymer properties upon functionalization. Strain rate=1.0 mm/s, average values and standard deviations reported from data collected over three experiments.
Figure 3B:
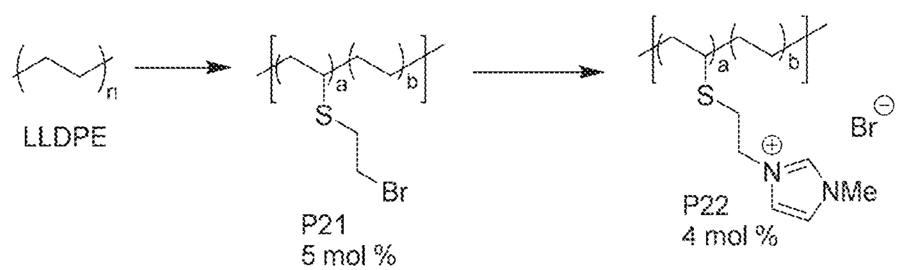
Figure 3C:
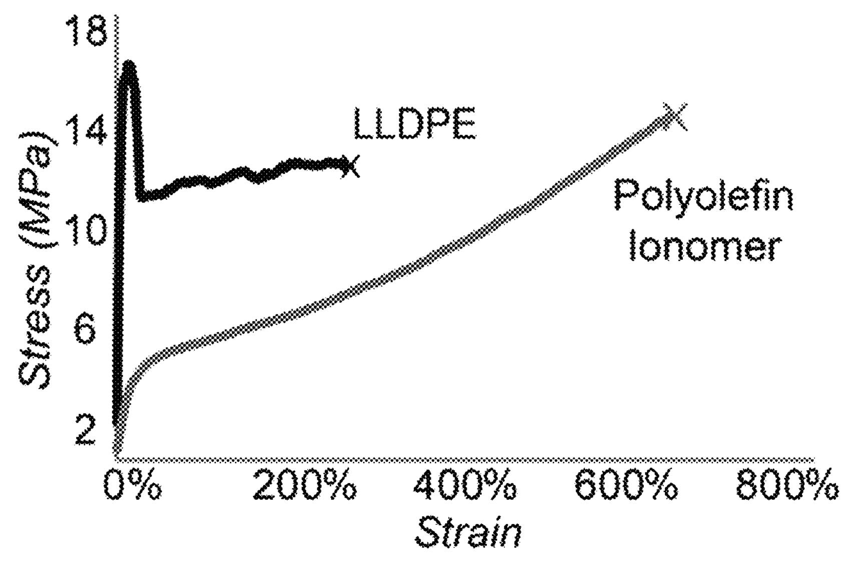
Figure 4:
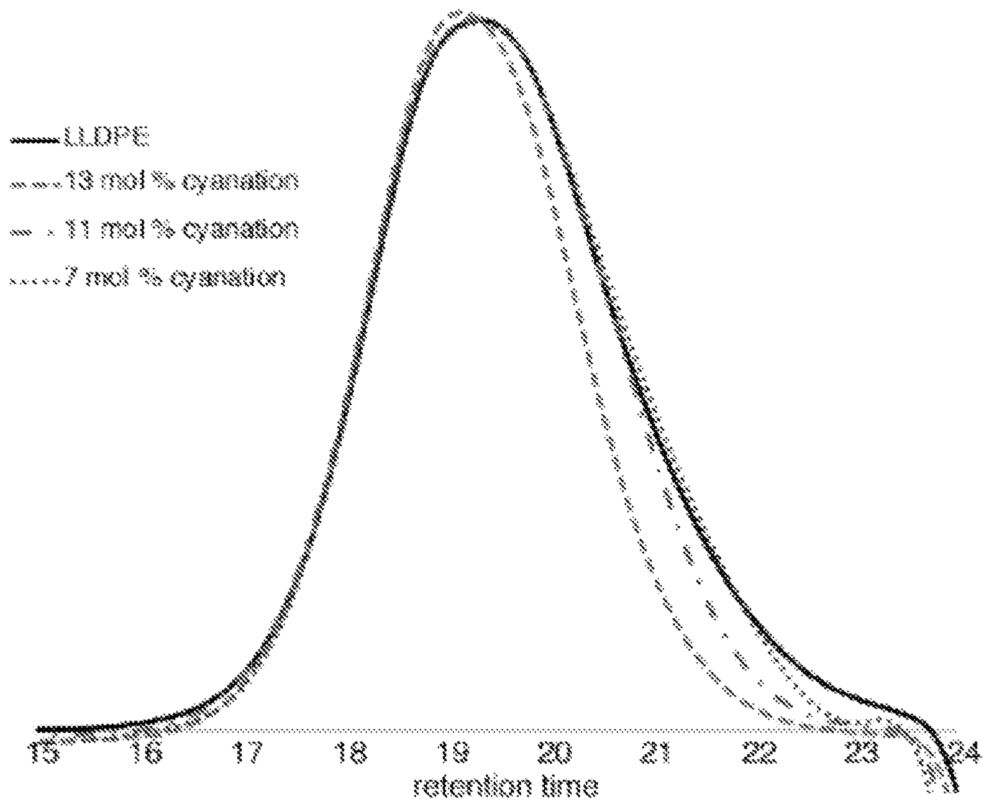
FIG. 4 is a chromatograph showing poly C—H cyanation using reagent 1 and tosyl cyanide successfully incorporated cyano groups into the polymer scaffold of LLDPE without significantly altering the molecular weight distribution according to GPC. Olefin gel permeation chromatographs (GPC) were obtained using a Tosoh EcoSEC-HT (high temperature) GPC with refractive index detection against polystyrene standards in 1 mg/mL solutions of trichlorobenzene (TCB) at 140° C.
Figure 5:
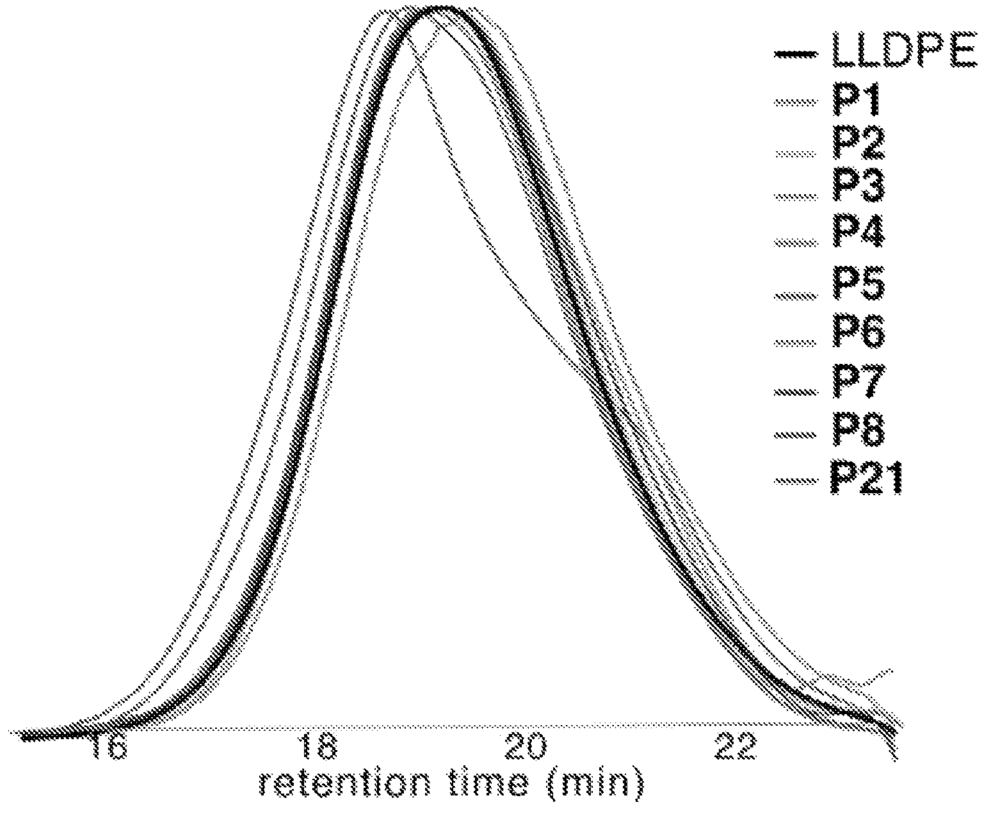
FIG. 5 is a chromatograph showing a multitude of functionalities were installed into the LLDPE microstructure using a method described herein. The GPC here demonstrates that the polyolefin C—H functionalization was successful without concurrent chain scission or chain coupling events. Two outliers exist: P1 (5 mol % fluorination) and P8 (2 mol % phenyl tetrazolation). The fluorinated LLDPE was confirmed by MALS to actually increase in molecular weight, contrary to what is observed by RI. Since P8 changed the shape of the molecular weight distribution. This radical trap may be less compatible with this chemistry as the others presented, though still useful.
Figure 6:
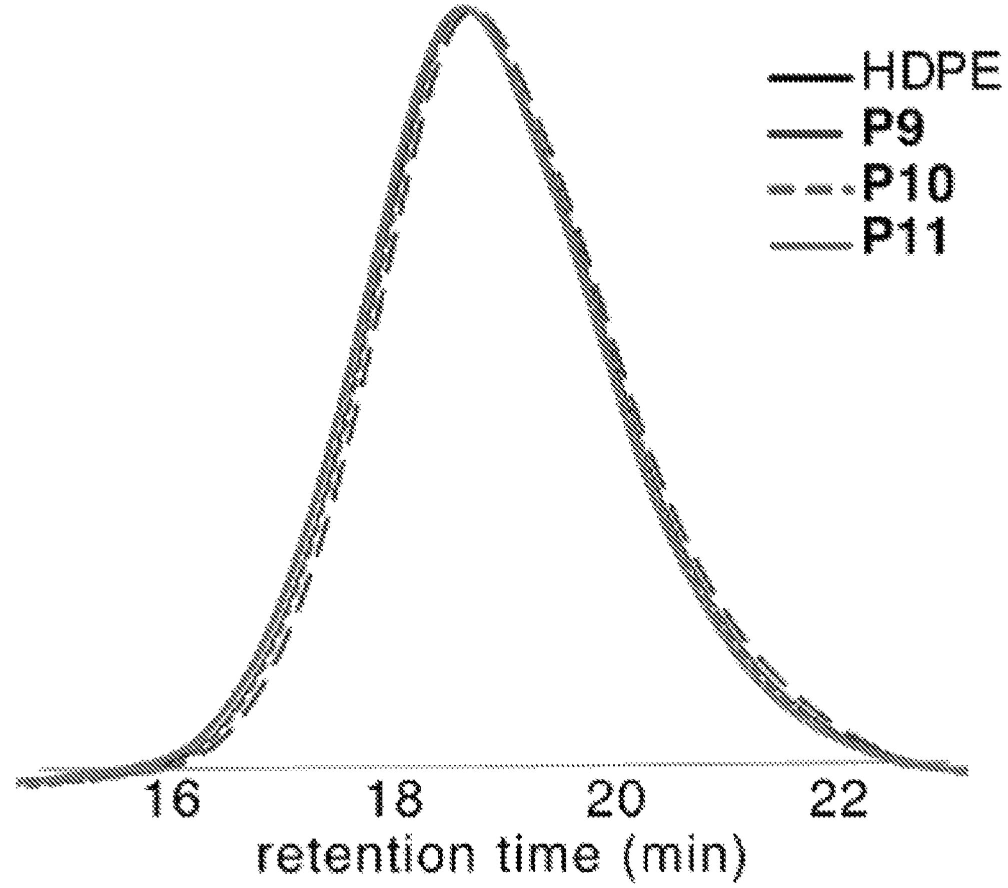
FIG. 6 is a chromatograph showing cyanation, thiophenolation, and iodination successfully C—H functionalized high-density polyethylene (HDPE) without altering the molecular weight distribution. The molecular weight and dispersity are almost identical pre- and post-functionalization.
Figure 7:
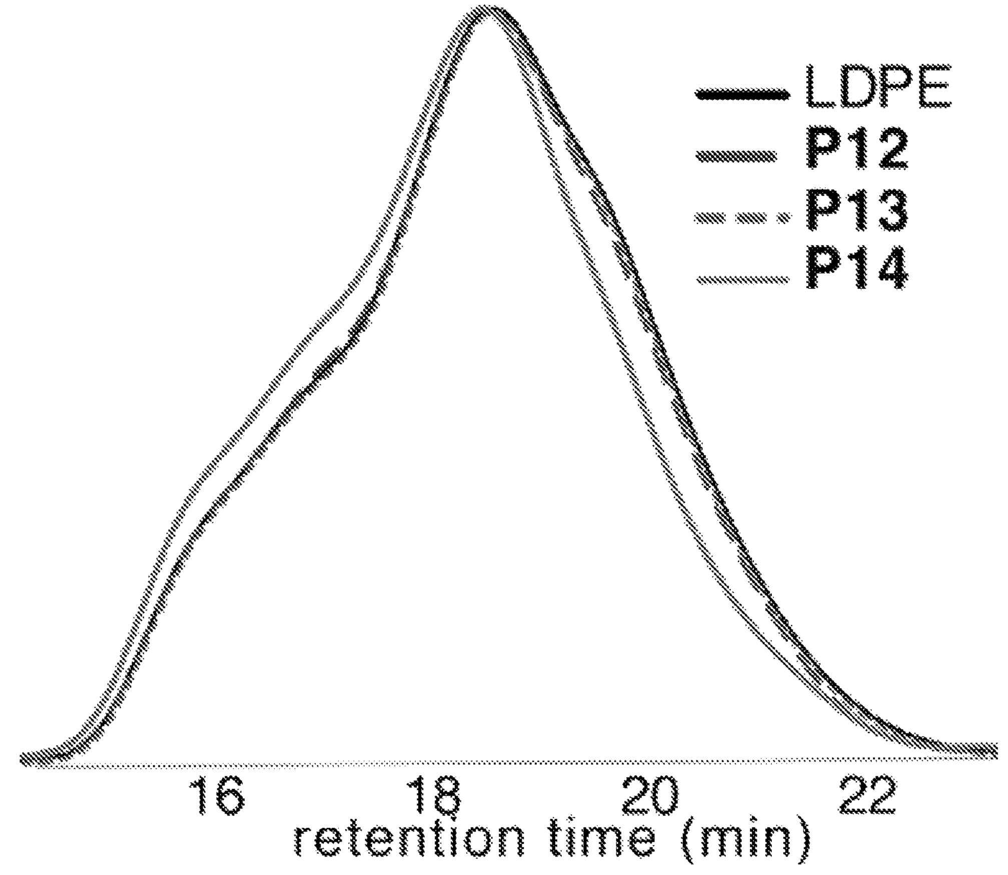
FIG. 7 is a chromatograph showing low-density polyethylene (LDPE) was functionalized with nitrile, iodo, and thiophenol moieties. According to the HT GPC, there was essentially no change to the molecular weight distribution.
Figure 8:
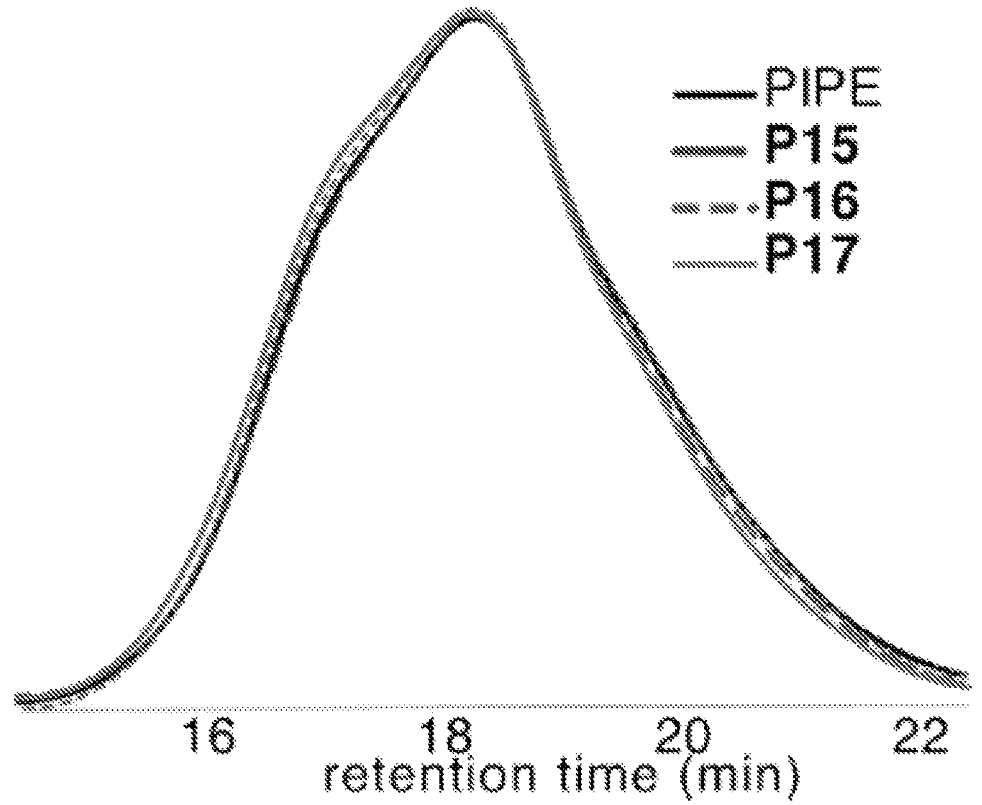
FIG. 8 is a chromatograph showing cyanated, iodination, and thiophenolated post-industrial polyethylene (PIPE) mimicked the molecular weight distribution of the virgin polymer. This demonstrates that the chemistry is chemoselective for C—H functionalization, even in the presence of additives and dyes.
Figure 9:
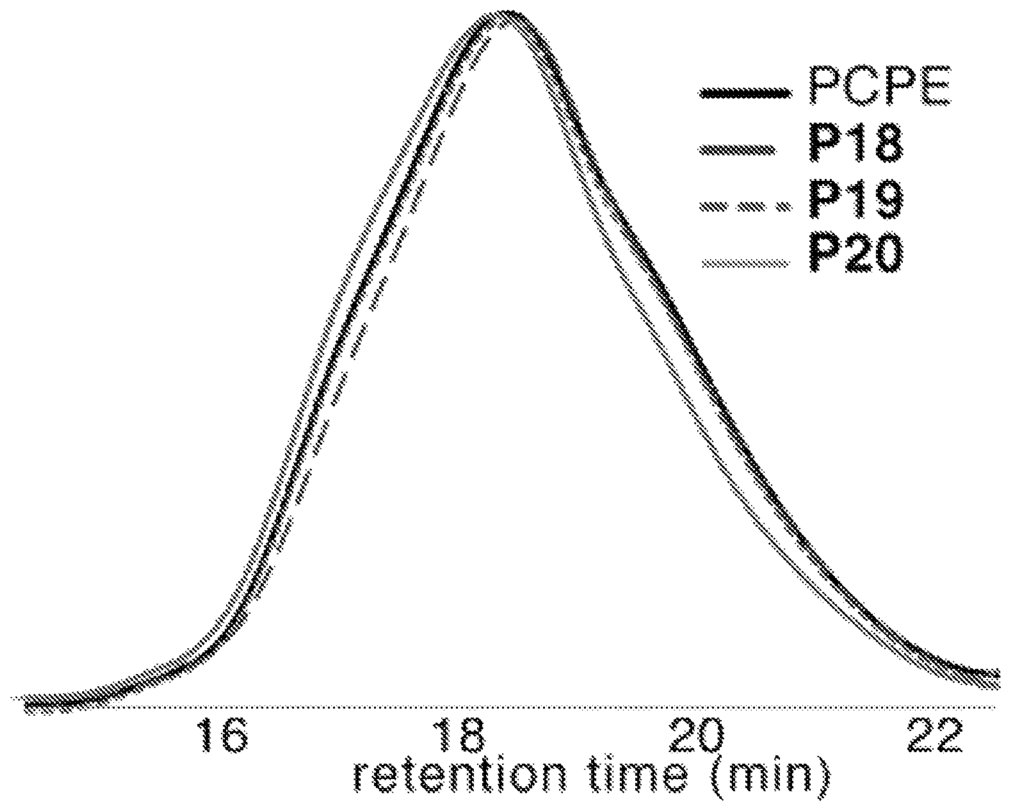
FIG. 9 is a chromatograph showing post-consumer polyethylene (PCPE) was reacted with 1 in the presence of tosyl cyanide, perfluorooctyl iodide, and S-phenyl benzenesulfonothioate to functionalize the polymer. Upon functionalization, the molecular weight distribution did not change according to HT GPC.
Figure 10:
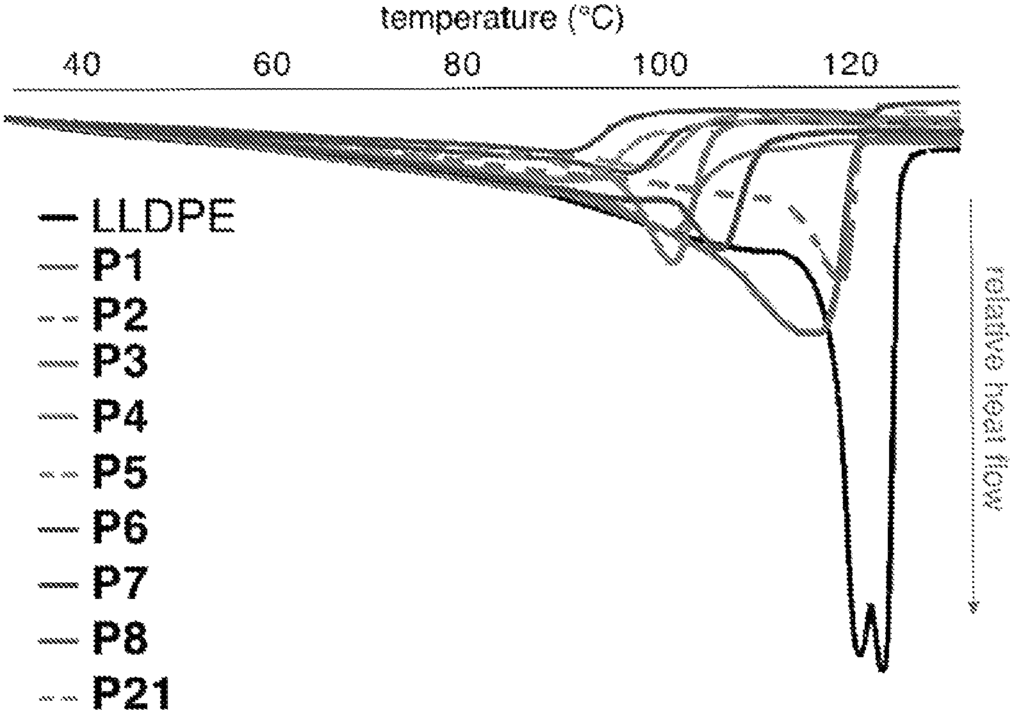
FIG. 10 is a DSC taken from the $2^{nd}$ heating cycle, the melting temperature and enthalphy of LLDPE and functionalized LLDPEs were analyzed. In all functionalizations, the semicrystallinity decreased, so observed through a decrease in enthalphy. The relative heat flow is normalized with respect to the sample mass.
Figure 11:
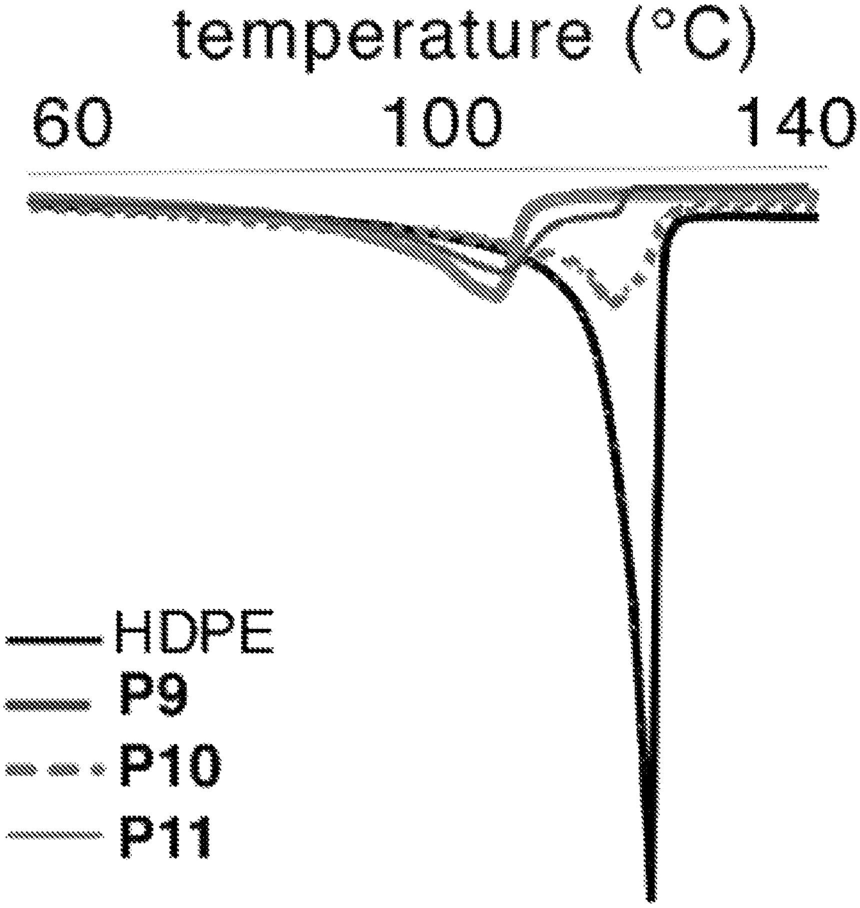
FIG. 11 is a DSC taken from the $2^{nd}$ heating cycle, the melting temperature and enthalphy of HDPE and functionalized HDPEs were analyzed. In all functionalizations, the semicrystallinity decreased, so observed through a decrease in enthalphy. The melting temperature of iodo-functional HDPE was most similar to the virgin polymer, but all functionalized HDPEs exhibited melting temperatures above 100° C.
Figure 12:
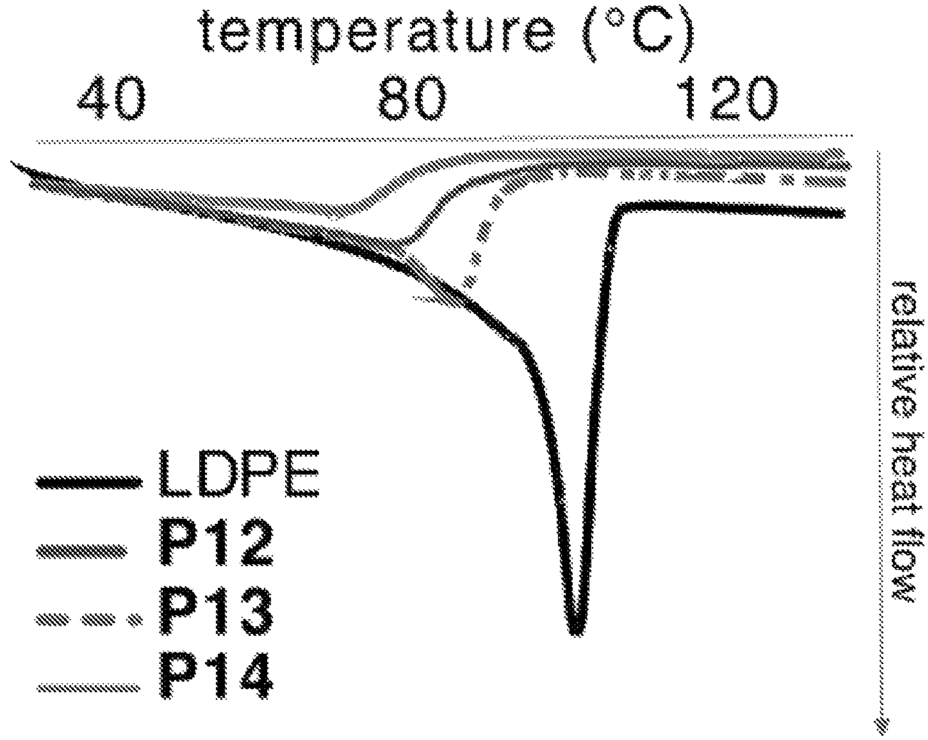
FIG. 12 is a DSC taken from the $2^{nd}$ heating cycle, the melting temperature and enthalphy of LDPE and functionalized LDPEs were analyzed. In all functionalizations, the semicrystallinity decreased as observed through a decrease in enthalphy. The melting temperature of iodo-functional LDPE was most similar to the virgin polymer, but all functionalized HDPEs exhibited melting temperatures above 60° C.
Figure 13:
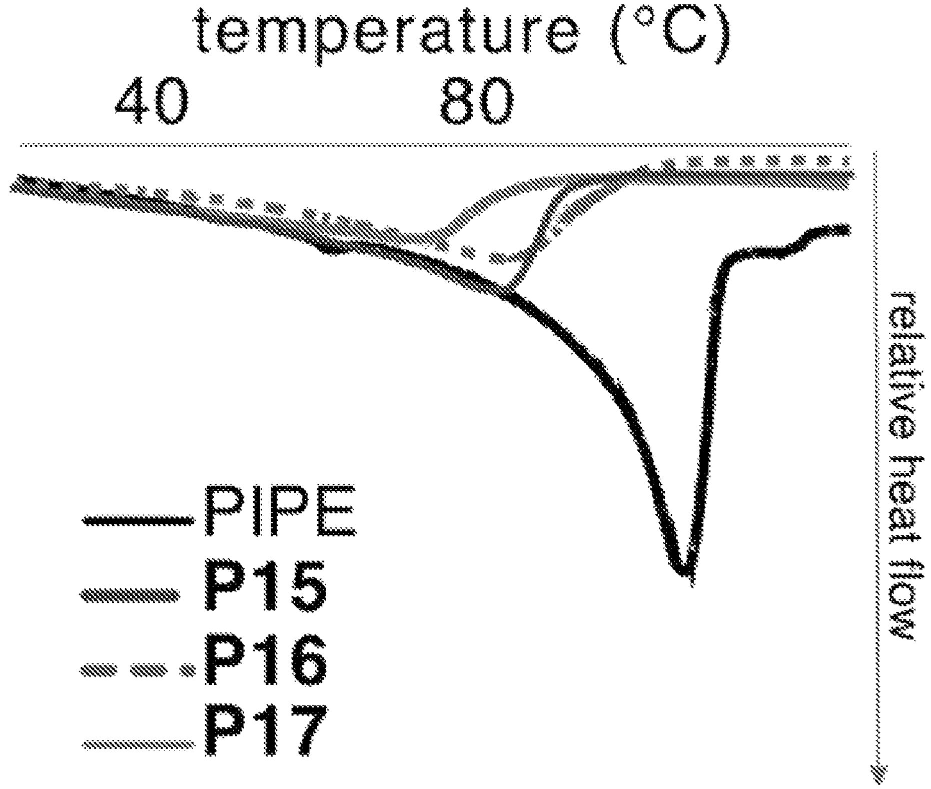
FIG. 13 is a DSC taken from the $2^{nd}$ heating cycle, the melting temperature and enthalphy of PIPE and functionalized PIPE were analyzed. In all functionalizations, the semicrystallinity decreased, so observed through a decrease in enthalphy. All functionalized PIPEs exhibited melting temperatures above 60° C., with a decrease in semicrystallinity with higher degrees of functionalization.
Figure 14:
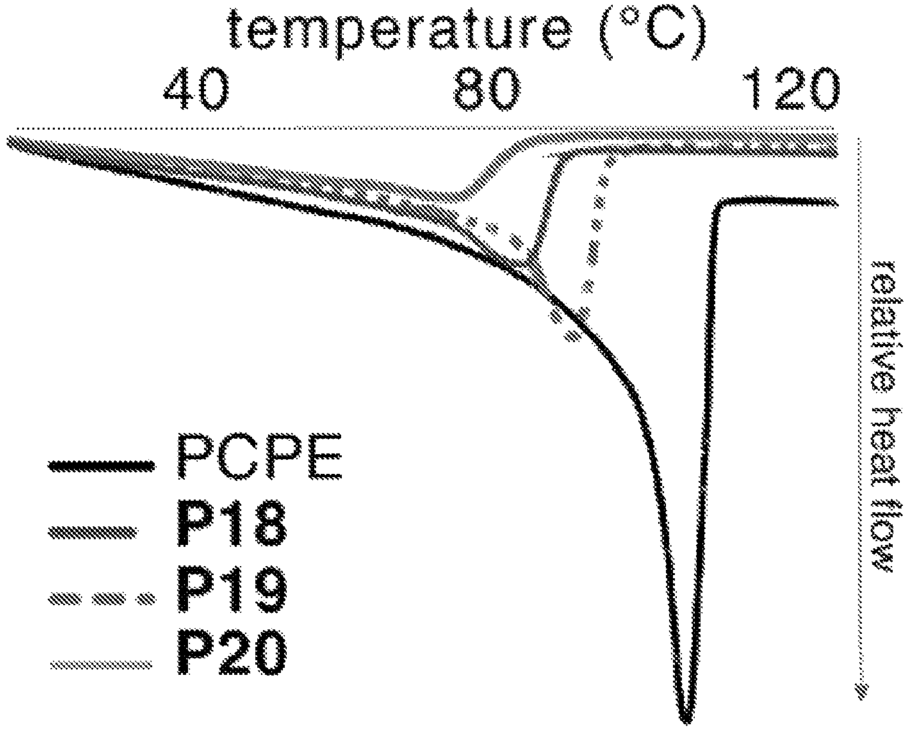
FIG. 14 is a DSC taken from the $2^{nd}$ heating cycle, the melting temperature and enthalphy of PCPE and functionalized PCPEs were analyzed. In all functionalizations, the semicrystallinity decreased as observed through a decrease in enthalphy. The iodo-functional PIPE most resembles the virgin PIPE melting temperature. All functionalized PIPEs exhibited melting temperatures above 60° C., with a decrease in semicrystallinity with higher degrees of functionalization.

In yet another advantage of the reagents and methods described herein, is the ability to place diverse functionality onto polyolefins through this universal approach. This approach provides an opportunity to substitute current high-value plastics, and create new ones, using post-consumer waste as a starting material. Polyolefin ionomers such as Surlyn™ and Nucrel™ are a high-value class of thermoplastics toughened by ionic crosslinks, with applications ranging from structural adhesives to ion-conducting membranes (39). However, polyolefin ionomers are synthesized through radical copolymerization of acrylic acid and ethylene, which limits polymer architecture to a highly branched microstructure, precludes use of a-olefins as comonomers, and limits functional group identity to a carboxylate. These limitations compromise the potential strength, toughness, and transport properties of the materials. There are currently no viable strategies to prepare polyolefin ionomers that enable access to ionic functionality on materials made through Ziegler-Natta or related catalytic approaches (i.e., LLDPE or HDPE). Given the structural fidelity and lack of long-chain branching of our polyolefin functionalization approach-evident from the high-temperature SECs post functionalization (FIG. 3A, S1-S6) we envisioned creating ionomers from polyolefins through late-stage functionalization. The generality of the C—H functionalization mediated by 1 enabled the development of a 2-bromoethyl thiosulfonate radical trapping reagent that installed a primary bromide onto the polyolefin (P21). Displacement of the bromide by methyl imidazole yielded imidazolium-functionalized LLDPE (P22), which represents a formal copolymerization of a-olefins with an ion-containing vinyl monomer. The ionomer had distinct properties from the parent LLDPE, including solubility in polar aprotic solvents, a decreased melting temperature, and enhanced clarity (FIG. S16). Introduction of the imidazolium to only 4 mol % of the repeat units dramatically changed the material from a thermoplastic to a tough elastomer (FIG. 3C). While yield stress and Young's modulus (E) of P22 decreased compared to the parent LLDPE, the strain at break (eB) more than doubled, leading to an increase in the tensile toughness (UT) of 180% while maintaining a similar stress at break (sB).

Collectively, the ability to produce an ionomer from a post-consumer waste stream with functional equivalence to the thermomechanical properties of Surlyn™ make this material an environmentally sustainable substitute for polyolefin ionomers (40), and the previous demonstration of polyolefin functionalization in an extruder using this class of reagents indicates the potential for scalability (20). While further reagent development is required to make this material an economically sustainable substitute, this platform does enables access to a library of unprecedented polyolefin ionomers that can systematically assess the impact of ion identity, ion content, and polymer branching.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, $—C(O)NH_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±50%. In certain other embodiments, the term "about" includes the indicated amount ±20%. In certain other embodiments, the term "about" includes the indicated amount #10%. In other embodiments, the term "about" includes the indicated amount ±5%. In certain other embodiments, the term "about" includes the indicated amount ±1%. In certain other embodiments, the term "about" includes the indicated amount ±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds.

"Alkyl" refers to an unbranched or branched saturated hydrocarbon chain. As used herein, alkyl has 1 to 20 carbon atoms (i.e., $C_1$-$C_{20}$ alkyl), 1 to 12 carbon atoms (i.e., $C_1$-$C_{12}$ alkyl), 1 to 8 carbon atoms (i.e., $C_1$-$C_8$ alkyl), 1 to 6 carbon atoms (i.e., $C_1$-$C_6$ alkyl), 1 to 4 carbon atoms (i.e., $C_1$-$C_4$ alkyl), or 1 to 3 carbon atoms (i.e., $C_1$-$C_3$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)$ 3); and "propyl" includes n-propyl (i.e., $—(CH_2)_2CH_3$) and isopropyl (i.e., $—CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl) or 2 to 4 carbon atoms (i.e., $C_2$-$C_4$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_2$-$C_{20}$ alkynyl), 2 to 8 carbon atoms (i.e., $C_2$-$C_8$ alkynyl), 2 to 6 carbon atoms (i.e., $C_2$-$C_6$ alkynyl) or 2 to 4 carbon atoms (i.e., $C_2$-$C_4$ alkynyl). The term "alkynyl" also includes those groups having one triple bond and one double bond.

The term "alkylene" by itself or as part of another substituent means a divalent radical derived from an alkane, such as, methylene $—CH_2—$, ethylene $—CH_2CH_2—$, and the like. As an example, a "hydroxy-methylene" refers to $HO—CH_2—*$, where * is the attachment point to the molecule.

"Alkoxy" refers to the group "alkyl-O—" (e.g., $C_1$-$C_3$ alkoxy or $C_1$-$C_6$ alkoxy). Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkoxy-alkyl" refers to the group "-alkyl-alkoxy" and the like. The term "$C_1$-$C_3$ alkoxy-$C_1$-$C_3$ alkyl" refers to a one to three carbon alkyl chain where one hydrogen on any carbon is replaced by an alkoxy group having one to three carbons, in particular, one hydrogen on one carbon of the alkyl chain is replaced by an alkoxy group having one to three carbons. The term, "$C_1$-$C_6$ alkoxy-$C_1$-$C_3$ alkyl" refers to a one to three carbon alkyl chain where one hydrogen on any carbon is replaced by an alkoxy group having one to six carbons, in particular, one hydrogen on one carbon of the alkyl chain is replaced by an alkoxy group having one to six carbons. Non-limiting examples of alkoxy-alkyl are $—CH_2OCH_3$, $—CH_2OC(CH_3)_3$, and $—C(CH_3)_2CH_2OCH_3$.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

The term "phenyl" or "Ph" refers to an aryl ring of the formula of $C_6H_5$ where the point of attachment to another group or moiety is one of the carbons. The phenyl may be substituted on the aromatic ring. In one embodiment, 0, 1, 2, 3, 4, or 5 atoms of the aryl group may be substituted by a substituent.

"Arylalkyl" or "Aralkyl" refers to the group "aryl-alkyl-" and the like, such as ($C_6$-$C_{10}$ aryl)-$C_1$-$C_3$ alkyl-. As used herein, "($C_6$-$C_{10}$ aryl)-$C_1$-$C_3$ alkyl" refers to a one to three carbon alkyl chain where one of the hydrogen atoms on any carbon is replaced by an aryl group having six to ten carbon atoms, in particular, one hydrogen on one carbon of the alkyl chain is replaced by an aryl group having six to ten carbon atoms. A non-limiting example of arylalkyl is benzyl.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), 3 to 7 ring carbon atoms (i.e., $C_3$-$C_7$ cycloalkyl), or 3 to 6 ring carbon atoms (i.e., $C_3$-$C_6$ cycloalkyl). Monocyclic groups include, for example, cyclopropyl, cyclobutyl, cyclopentyl, cyclohexyl, cycloheptyl and cyclooctyl. Polycyclic groups include, for example, bridged and/or fused rings, such as bicyclo[2.2.1]heptanyl, bicyclo[2.2.2]octanyl, bicyclo[1.1.1]pentan-1-yl, adamantyl, norbornyl, decalinyl, 7,7-dimethyl-bicyclo[2.2.1]heptanyl and the like. Further, the term cycloalkyl is intended to encompass any ring or ring system comprising a non-aromatic alkyl ring which may be fused to an aryl ring, regardless of the attachment to the remainder of the molecule. Further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-" and the like, such as ($C_3$-$C_6$ cycloalkyl)-$C_1$-$C_3$ alkyl. As used herein, "($C_3$-$C_6$ cycloalkyl)-$C_1$-$C_3$ alkyl" refers to a one to three carbon alkyl chain where one of the hydrogen atoms on any carbon is replaced by a cycloalkyl group having three to six carbon atoms, in particular, one hydrogen on one carbon of the chain is replaced by a cycloalkyl group having three to six carbon atoms.

"Halogen" or "halo" refers to atoms occupying group VIIA of the periodic table, such as fluoro (fluorine), chloro (chlorine), bromo (bromine) or iodo (iodine). "Haloalkyl" refers to an unbranched or branched alkyl group as defined above that is a substituted alkyl, wherein one or more (e.g., 1 to 6, or 1 to 3) hydrogen atoms are replaced by a halogen. For example, halo-$C_1$-$C_3$ alkyl refers to an alkyl group of 1 to 3 carbons wherein at least one hydrogen atom is replaced by a halogen. Where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Hydroxyalkyl" refers to an alkyl group as defined above that is a substituted alkyl, wherein one or more (e.g., 1 to 6, or 1 to 3) hydrogen atoms are replaced by a hydroxy group (e.g., hydroxy-$C_1$-$C_3$-alkyl, hydroxy-$C_1$-$C_6$-alkyl). The term "hydroxy-$C_1$-$C_3$ alkyl" refers to a one to three carbon alkyl chain where one or more hydrogens on any carbon is replaced by a hydroxy group, in particular, one hydrogen on one carbon of the chain is replaced by a hydroxy group. The term "hydroxy-$C_1$-$C_6$ alkyl" refers to a one to six carbon alkyl chain where one or more hydrogens on any carbon is replaced by a hydroxy group, in particular, one hydrogen on one carbon of the chain is replaced by a hydroxy group. Non-limiting examples of hydroxyalkyl include-$CH_2OH$, —$CH_2CH_2OH$, and —$C(CH_3)_2CH_2OH$.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. In certain embodiments, the heteroalkyl can have 1 to 3 carbon atoms (e.g., $C_1$-$C_3$ heteroalkyl) or 1 to 6 carbon atoms (e.g., $C_1$-$C_6$ heteroalkyl), and one or more (e.g., 1, 2, or 3) heteroatoms or heteroatomic groups. The term "heteroalkyl" includes unbranched or branched saturated chain having carbon and heteroatoms. By way of example, 1, 2 or 3 carbon atoms of the alkyl group in the "heteroalkyl" may be independently replaced with the same or different heteroatomic group. Heteroatomic groups include, but are not limited to, —$NR^y$—, —O—, —S—, —S(O)—, —$S(O)_2$—, and the like, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)$ $OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2O$ $CH_3$, etc.) and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yC$ $H_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). In certain embodiments, heteroalkyl can have 1 to 20 carbon atoms, 1 to 15 carbon atoms, 1 to 12 carbon atoms, 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_1$-$C_{20}$ heteroaryl), 3 to 12 ring carbon atoms (i.e., $C_3$-$C_{12}$ heteroaryl), or 3 to 8 carbon ring atoms (i.e., $C_3$-$C_8$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems (i.e., 9-10 membered heteroaryl), 5-10 membered ring systems (i.e., 5-10 membered heteroaryl), 5-7 membered ring systems (i.e., 5-7 membered heteroaryl), 5-6 membered ring systems (i.e., 5-6 membered heteroaryl), or 4-6 membered ring systems (i.e., 4-6 membered heteroaryl), each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl.

Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring or ring system, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-", such as (5- to 10-membered monocyclic heteroaryl)-$C_1$-$C_3$ alkyl. As used, herein, "(5- to 10-membered monocyclic heteroaryl)-$C_1$-$C_3$ alkyl" refers to a one to three carbon alkyl chain where one or more hydrogens on any carbon is replaced by a monocyclic heteroaryl group having 5- to 10-members, in particular, one hydrogen on one carbon of the chain is replaced by a (5- to 10-membered monocyclic heteroaryl group.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro. Any non-aromatic ring containing at least one heteroatom is considered a heterocyclyl, regardless of the attachment (i.e., can be bound through a carbon atom or a heteroatom). Further, the term heterocyclyl is intended to encompass a ring or ring system comprising any non-aromatic ring containing at least one heteroatom, which ring may be fused to an aryl or heteroaryl ring, regardless of the attachment to the remainder of the molecule. The term heterocyclyl is also intended to encompass a ring system comprising a cycloalkyl ring which is fused to a heteroaryl ring, regardless of the attachment to the remainder of the molecule. Additionally, the term heterocyclyl is intended to encompass a ring system comprising a cycloalkyl ring which is fused to a heterocyclyl ring, regardless of the attachment to the remainder of the molecule. As used herein, heterocyclyl has 2 to 20 ring carbon atoms (i.e., $C_2$-$C_{20}$ heterocyclyl), 2 to 12 ring carbon atoms (i.e., $C_2$-$C_{12}$ heterocyclyl), 2 to 10 ring carbon atoms (i.e., $C_2$-$C_{10}$ heterocyclyl), 2 to 8 ring carbon atoms (i.e., $C_2$-$C_8$ heterocyclyl), 3 to 12 ring carbon atoms (i.e., $C_3$-$C_{12}$ heterocyclyl), 3 to 8 ring carbon atoms (i.e., $C_3$-$C_8$ heterocyclyl), or 3 to 6 ring carbon atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. When the heterocyclyl ring contains 4- to 6-ring atoms, it is also referred to herein as a 4- to 6-membered heterocyclyl. Also disclosed herein are 5- or 6-membered heterocyclyls, having 5 or 6 ring atoms, respectively, and 5- to 10-membered heterocyclyls, having 5 to 10 ring atoms. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. In certain embodiments, the term "heterocyclyl" can include "spiroheterocyclyl" when there are two positions for substitution on the same carbon atom. Examples of the spiroheterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, 1 to 4, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5, 1 to 4, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, $-NHNH_2$, $=NNH_2$, imino, imido, hydroxy, oxo, oxime, nitro, sulfonyl, sulfinyl, alkylsulfonyl, alkylsulfinyl, thiocyanate, $-S(O)OH$, $-S(O)_2OH$, sulfonamido, thiol, thioxo, N-oxide or $-Si(R^y)_3$, wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, 1 to 4, or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, $-NR^gR^h$, $-NR^gC(=O)R^h$, $-NR^gC(=O)NR^gR^h$, $-NR^gC(=O)OR^h$, $-NR^gS(=O)_{1-2}R^h$, $-C(=O)R^g$, $-C(=O)OR^g$, $-OC(=O)OR^g$, $-OC(=O)R^g$, $-C(=O)NR^gR^h$, $-OC(=O)NR^gR^h$, $-OR^g$, $-SR^g$, $-S(=O)R^g$, $-S(=O)_2R^g$, $-OS(=O)_{1-2}R^g$, $-S(=O)_{1-2}OR^g$, $-NR^gS(=O)_{1-2}NR^gR^h$, $=NSO_2R^g$, $=NOR^g$, $-S(=O)_{1-2}NR^gR^h$, $-SF_5$, $-SCF_3$ or $-OCF_3$. In certain embodiments, "substituted" also means any of the above groups in which one or more (e.g., 1 to 5, 1 to 4, or 1 to 3) hydrogen atoms are replaced with $-C(=O)R^g$, $-C(=O)OR^g$, $-C(=O)NR^gR^h$, $-CH_2SO_2R^g$, or $-CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl.

In certain embodiments, "substituted" also means any of the above groups, in particular a substituted alkyl, cycloalkyl, aryl, heteroaryl, or heterocyclyl, in which one or more (e.g., 1 to 5, 1 to 4, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl, or alkoxy. In certain embodiments, "substituted" also means any of the above groups, in particular a substituted alkyl, cycloalkyl, aryl, heteroaryl, or heterocyclyl, in which one or more (e.g., 1 to 5, 1 to 4, or 1 to 3) hydrogen atoms are replaced by a bond to an amino, cyano, hydroxyl, nitro, halo, alkoxy, alkylamino, cycloalkyl, heterocyclyl, aryl or heteroaryl. In certain embodiments, "substituted" also means any of the above groups, in particular a substituted alkyl, cycloalkyl, aryl, heteroaryl, or heterocyclyl, in which one or more (e.g., 1 to 5, 1 to 4, or 1 to 3) hydrogen atoms are replaced by a bond to an amino, cyano, hydroxyl, nitro, halo, alkoxy, or alkylamino.

Structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

As used herein, the term "initiator" refers to a chemical or form of energy that can produce a radical species and promote radical reactions. Forms of energy useful as a free radical initiators are heat and light. This can include visible light or mild heat. In certain embodiments, an initiator other than visible light or mild heat is not used. However, examples of chemicals used as initiators are halogen molecules, azo compounds, and organic and inorganic peroxides. Specific non-limiting examples are di-tert-butyl peroxide, dilauroyl peroxide (DLP), 2,5-dimethyl-2,5-di-tertiary-butyl-peroxyhexane, dicumyl peroxide; alkyl peroxides such as tertiary-butyl hydroperoxide, tertiary-octyl hydroperoxide, cumene hydroperoxide; aroyl peroxides such as benzoyl peroxide (BPO); peroxy esters such as tertiary-butyl peroxypivalate, tertiary-butyl perbenzoate; and azo compounds such as azo-bis-isobutyronitrile (AIBN). Non-limiting examples of light sources used as free radical initiators are light emitting diodes (LED) and compact fluorescent lamps (CFL).

As used herein, the term "external trap" is a molecule containing a transfer group X that interacts with one or both of a reagent and a substrate, whereby the transfer group X is covalently bound to the substrate.

The term "substrate radical" refers to an intermediate in the processes described herein whereby the substrate, e.g. a PI or PC feedstock, is converted to a reactive species.

As used herein, the term "post-industrial" or "PI" refers to a stream of polyolefin-based polymer feedstock for the processes described herein. In certain embodiments, the post-industrial polymer is obtained from production waste. As used herein, the term "post-consumer" or "PC" refers to a stream of polyolefin-based polymer feedstock for the process described herein. In certain embodiments, the post-consumer polymer is obtained from post-consumer products. Regardless of the feedstock, the polymer can be in a form produced by regrinding. The feedstocks can contain primarily polypropyle (PP), polyethylene (PE) and mixed polyolefins (MPO). However, feedstocks can include any PC or PI polymers that include, but are not limited to, polyethylene (PE), low-density polyethylene (LPDE), linear low density (LLDPE), high density (HDPE), polypropylene, polyvinylchloride, polystyrene, and polyethylene terephthalate. The term "substrate" refers to any of the feedstock materials.

As used herein, the "contacting" refers to reagents in close proximity so that a reaction may occur. As used herein, the term "modified" refers to covalently transforming the starting material, whereby the resulting product has a measurable change in a chemical or physical property.

As used herein, the term "solvent" refers to any solvent that does not contain an extractable hydrogen, such as common aromatic solvents. Non-limiting examples include benzene and halogenated benzenes, such as chlorobenzene and trifluoromethyltoluene. Other non-limiting examples include MeCN and dichloroethane.

Additional definitions may be set forth below.

II. Compounds and Methods

In certain embodiments, the subject matter described herein is directed to a compound of Formula I-A:

I-A

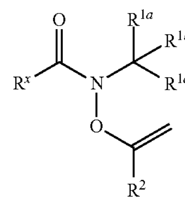

wherein,

- $R^x$ is an optionally substituted linear or branched $C_{1-10}$ alkyl or optionally substituted $C_{6-10}$ aryl;
- $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$,
  - wherein, Q is O or is absent;
  - $R^{10a}$ is hydrogen or $C_{1-6}$ alkyl; and
  - wherein, the cycloalkyl, aryl, heteroaryl, heterocyclyl and alkyl can each be independently optionally substituted;

and,

- $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$.

In certain embodiments, in Formula I-A, only one or two of $R^{1a}$, $R^{1b}$ and $R^{1c}$ can be hydrogen. In certain embodiments, only one of $R^{1a}$, $R^{1b}$ and $R^{1c}$ can be hydrogen. In certain embodiments, only two of $R^{1a}$, $R^{1b}$ and $R^{1c}$ can be hydrogen. In certain embodiments, $R^{1a}$ is hydrogen, $R^{1b}$ is methyl and $R^{1c}$ is methyl.

In certain embodiments, the subject matter described herein is directed to a compound of Formula I:

I

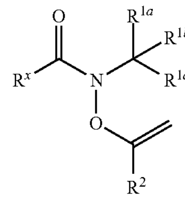

wherein,

- $R^x$ is an optionally substituted linear or branched $C_{1-10}$ alkyl or optionally substituted $C_{6-10}$ aryl;
- $R^{1a}$, $R^{1b}$ and $R^{1c}$ are each independently selected from the group consisting of $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$; or, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$.

In certain embodiments, in Formula I, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$, wherein, Q is O or is absent; only one or two of $R^{1a}$, $R^{1b}$ and $R^{1c}$ can be hydrogen. In certain embodiments, only one of $R^{1a}$, $R^{1b}$ and $R^{1c}$ can be hydrogen. In certain embodiments, only two of $R^{1a}$, $R^{1b}$ and $R^{1c}$ can be hydrogen. In certain embodiments, $R^{1a}$ is hydrogen, $R^{1b}$ is methyl and $R^{1c}$ is methyl.

In certain embodiments, $R^{1a}$, $R^{1b}$ and $R^{1c}$ are each independently selected from the group consisting of $C_{3-8}$ cycloalkyl, $C_{2-8}$ heterocyclyl, linear or branched $C_{1-6}$ alkyl, —CN, and —C(═O)-Q-$R^{10}$.

In certain embodiments, at least one of $R^{1a}$, $R^{1b}$ and $R^{1c}$ is a linear or branched $C_{1-6}$ alkyl.

In certain embodiments, each of $R^{1a}$, $R^{1b}$ and $R^{1c}$ is methyl.

In certain embodiments, the subject matter described herein is directed to a compound having a structure of Formula II:

II

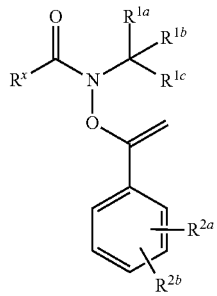

wherein, $R^{2a}$ and $R^{2b}$ are each independently selected from the group consisting of hydrogen, halo, optionally substituted linear or branched $C_{1-10}$ alkyl, —CN, $C_{1-6}$ alkoxy, —$NO_2$, —$NR^aR^b$, —(C═O)$OR^c$ and —(C═O)$R^c$, wherein, $R^a$, $R^b$ and $R^c$ are each independently selected from the group consisting of hydrogen, methyl, ethyl, propyl and butyl.

In certain embodiments, $R^{2a}$ and $R^{2b}$ are each hydrogen.

In certain embodiments, $R^x$ is selected from the group consisting of —$CF_3$, methyl, t-butyl and optionally substituted phenyl.

In certain embodiments, $R^x$ is an optionally substituted phenyl.

In certain embodiments, the optionally substituted phenyl has the structure:

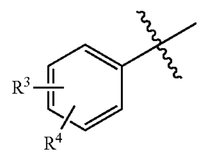

wherein, $R^3$ and $R^4$ are each independently selected from the group consisting of halo-$C_{1-6}$ alkyl, halo, —CN, and —$NO_2$.

In certain embodiments, at least one of $R^3$ and $R^4$ is halo-$C_{1-6}$ alkyl.

In certain embodiments, $R^3$ is selected from the group consisting of F, Cl, —$CF_3$, —$CHF_2$ and $CH_2F$.

In certain embodiments, $R^4$ is selected from the group consisting of F, Cl, —$CF_3$, —$CHF_2$ and $CH_2F$.

In certain embodiments, the halo-$C_{1-6}$ alkyl is $CF_3$.

In certain embodiments, in Formula II, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$, wherein, Q is O or is absent; only one or two of $R^{1a}$, $R^{1b}$ and $R^{1c}$ can be hydrogen. In certain embodiments, only one of $R^{1a}$, $R^{1b}$ and $R^{1c}$ can be hydrogen. In certain embodiments, only two of $R^{1a}$, $R^{1b}$ and $R^{1c}$ can be hydrogen. In certain embodiments, $R^{1a}$ is hydrogen, $R^{1b}$ is methyl and $R^{1c}$ is methyl.

In certain embodiments, the subject matter described herein is directed to a compound having a structure of Formula III:

III

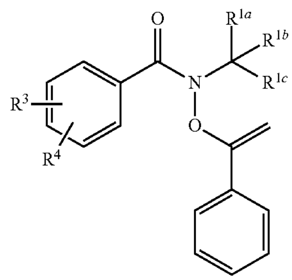

wherein, $R^3$ and $R^4$ are each independently selected from the group consisting of halo-$C_{1-6}$ alkyl, halo, —CN, and —$NO_2$.

In certain embodiments, in Formula I, $R^{1a}$, $R^{1b}$ and Rie are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$, wherein, Q is O or is absent; only one or two of $R^{1a}$, $R^{1b}$ and $R^{1c}$ can be hydrogen. In certain embodiments, only one of $R^{1a}$, $R^{1b}$ and $R^{1c}$ can be hydrogen. In certain embodiments, only two of $R^{1a}$, $R^{1b}$ and $R^{1c}$ can be hydrogen. In certain embodiments, $R^{1a}$ is hydrogen, $R^{1b}$ is methyl and $R^{1c}$ is methyl.

In certain embodiments, each of $R^{1a}$, $R^{1b}$ and $R^{1c}$ is methyl.

In certain embodiments, at least one of $R^3$ and $R^4$ is halo-$C_{16}$ alkyl.

In certain embodiments, $R^3$ is selected from the group consisting of F, Cl, —$CF_3$, —$CHF_2$ and $CH_2F$.

In certain embodiments, $R^4$ is selected from the group consisting of F, Cl, —$CF_3$, —$CHF_2$ and $CH_2F$.

In certain embodiments, at least one halo-$C_{1-6}$ alkyl is $CF_3$.

In certain embodiments, the compound has the structure:

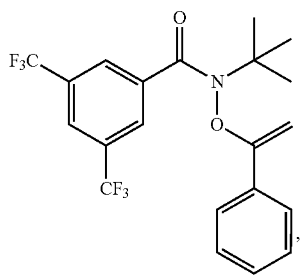 [SMILES: C=C(ON(C(=O)c1cc(C(F)(F)F)cc(C(F)(F)F)c1)C(C)(C)C)c1ccccc1]

In certain embodiments, the subject matter described herein is directed to a mixture comprising:

a solvent;

a compound of Formula I:

I

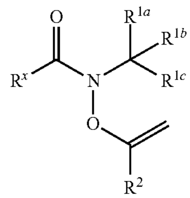

wherein, $R^x$ is an optionally substituted linear or branched $C_{1-10}$ alkyl or optionally substituted $C_{6-10}$ aryl;

$R^1$, $R^{1b}$ and $R^{1c}$ are each independently selected from the group consisting of $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-3}$ heterocyclyl, linear or branched $C_{1-6}$ alkyl, hydroxy-$C_1$-$C_6$-alkyl —CN, and —C(═O)-Q-$R^{10}$; or, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$ and, at least one of the following:

i. a compound of Formula T-A:

T-A

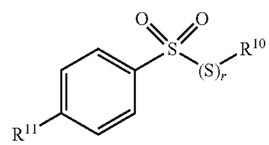

wherein, $R^{11}$ is selected from the group consisting of hydrogen, halo, halo-$C_{1-6}$ alkyl, —CN, $C_{1-6}$ alkyl and $C_{1-6}$ alkoxy;

f is 0 or 1;

$R^{10}$, when f is 1, is selected from the group consisting of halo-$C_{1-6}$ alkyl, and optionally substituted $C_{6-10}$ aryl; or $R^{10}$, when f is 0, is selected from the group consisting of —CN and —$N_3$;

or, i(a). a compound of Formula T-A1:

T-A1

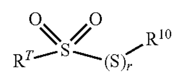

wherein, $R^T$ is selected from the group consisting of $C_{1-6}$ alkyl and $C_{6-10}$ aryl, wherein the $C_{6-10}$ aryl is optionally substituted with $R^{11}$;

$R^{11}$ is selected from the group consisting of hydrogen, phenyl, halo, —C(O)O—$C_{1-6}$ alkyl, halo-$C_{1-6}$ alkyl, —CN, $C_{1-6}$ alkyl and $C_{1-6}$ alkoxy;

f is 0 or 1;

$R^{10}$ is a moiety that along with —$(S)_f$— is an X moiety for transferring and binding to a carbon on a substrate;

or, ii. an external trap as shown in Table 1;

or, iii. a radical trap comprising an X moiety for transferring and binding to a carbon on a substrate.

In certain embodiments, $R^{10}$ is optionally substituted $C_{3-8}$ heteroaryl halo-$C_{16}$ alkyl, and optionally substituted $C_{6-10}$ aryl.

In certain embodiments, $R^{10}$ is haloethyl.

In certain embodiments, $R^{10}$ is

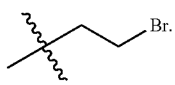 [SMILES: *CCBr]

In certain embodiments, the molar ratio of the compound of Formula I and the compound of Formula T-A or Formula T-A1 is from about 0.1:1 to about 1:0.1.

In certain embodiments, the molar ratio of the compound of Formula I and the compound of Formula T-A or Formula T-A1 is about 1:5, or about 1:2, or about 1:1, or about 2:1, or about 5:1.

In certain embodiments, the mixture further comprises a substrate. In certain embodiments, the substrate is a small molecule or a polymer, wherein the small molecule and polymer contains a C—H bond.

In Formula T-A1 and Formula T-A, the X moiety for transferring and binding to a carbon on a substrate is represented by:

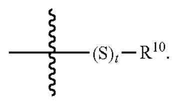

In Formula T-A1 and Formula T-A and in the radical trap, an X moiety for transferring and binding to a carbon on a substrate (also referred to herein as a transfer group X and the like) is any chemical group known in the art for being capable of covalently binding to a carbon. In certain embodiments, in Formula T-A1, an X moiety for transferring and binding to a carbon on a substrate is selected from the group consisting of halo-$C_{16}$ alkyl, optionally substituted $C_{6-10}$ aryl, optionally substituted $C_{3-8}$ heteroaryl, —S—$C_{3-8}$ heteroaryl which can be optionally substituted, —CN and —$N_3$. In certain embodiments in Formula T-A1, $R^{10}$, when f is 1, is selected from the group consisting of halo-$C_{1-6}$ alkyl, optionally substituted $C_{3-8}$ heteroaryl, and optionally substituted $C_{6-10}$ aryl. In certain embodiments in Formula T-A1, $R^{10}$, when f is 0, is selected from the group consisting of optionally substituted $C_{3-8}$ heteroaryl, —S—$C_{3-8}$ heteroaryl which can be optionally substituted —CN and —$N_3$. When optionally substituted, the substituent can be selected from the group consisting of halo, nitro, —C(O)O—$C_{1-6}$ alkyl, halo-$C_{1-6}$ alkyl, —CN, $C_{1-6}$ alkyl and $C_{1-6}$ alkoxy.

As described herein, the methods form a covalent bond between a carbon (—C—H) on a substrate and a transferred moiety depicted in the box:

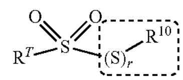

where f is 1 or 0.

In certain embodiments, $R^T$ in Formula T-A1 is $C_{1-6}$ alkyl. In certain embodiments, $R^T$ in Formula T-A1 is methyl.

In certain embodiments, Formula T-A1 compounds include, but are not limited to:

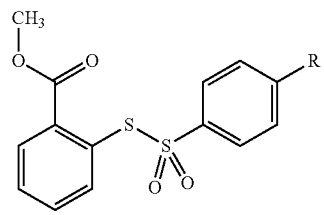

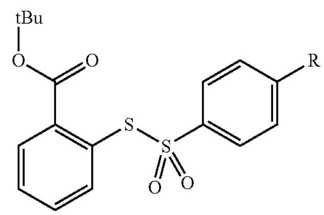

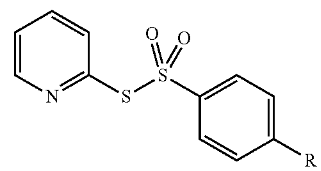

R = H, Me, $CF_3$

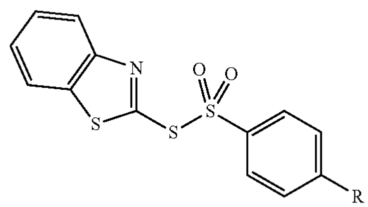

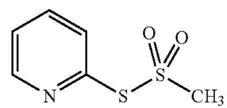

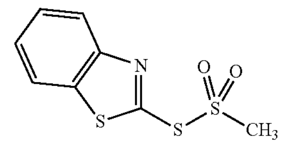

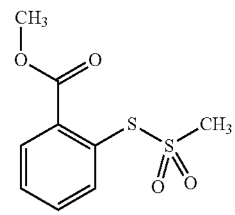

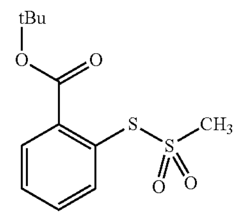

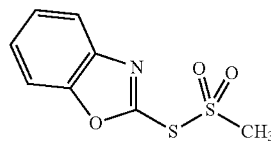

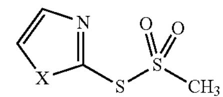

-continued

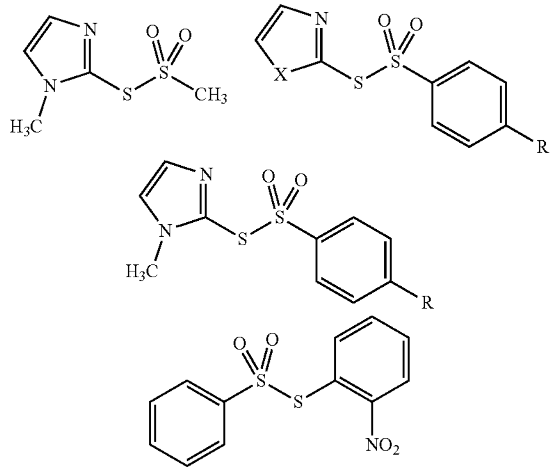

A proposed, non-limiting mechanism including a reaction of an exemplary radical trap is depicted below:

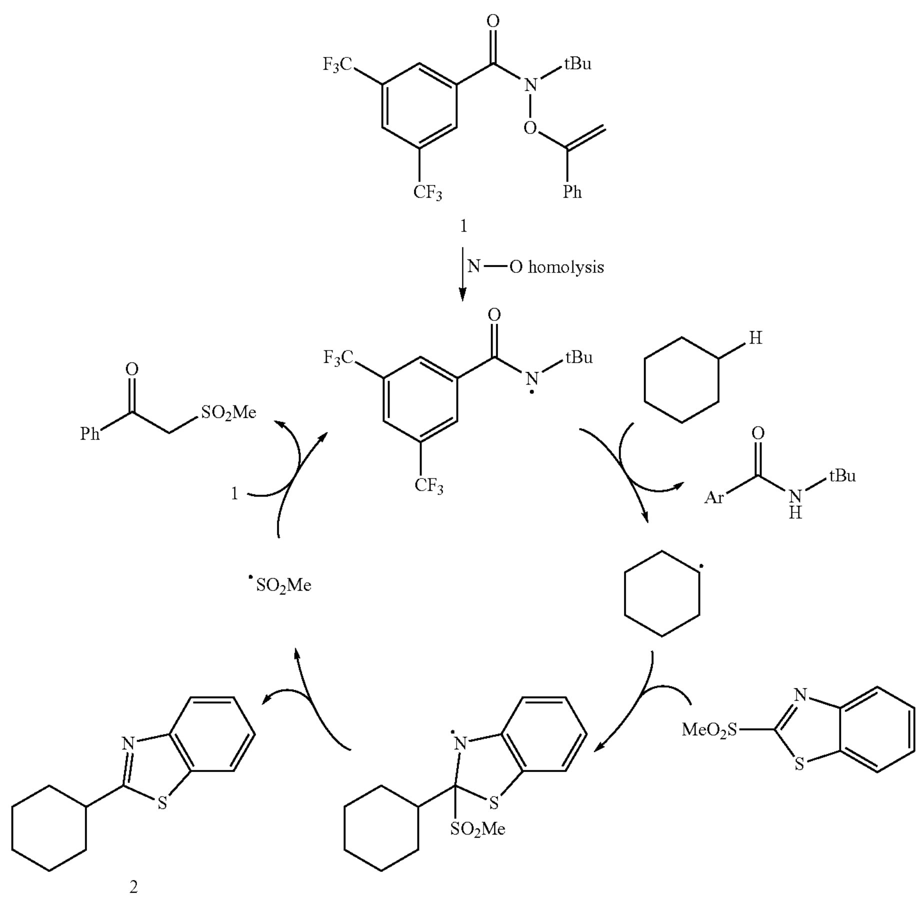

In certain embodiments, the subject matter described herein is directed to a method of functionalizing a substrate, comprising:

i. in the presence of a radical trap comprising a transfer group X and the substrate, wherein the substrate comprises a C—H bond, allowing a compound of Formula I:

I

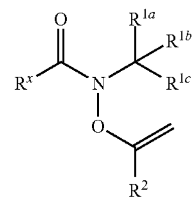

wherein, $R^x$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$; or, $R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

and $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$;

to contact an initiator to form a nitrogen-centered radical;

ii. allowing the substrate comprising a C—H bond to contact the nitrogen-centered radical to form a substrate radical;

iii. allowing the substrate radical to contact the radical trap comprising a transfer group X, wherein, a C—H bond in the substrate is functionalized to a covalent C—X bond, wherein X is the transfer group.

In certain embodiments, the initiator is heat or light. In certain embodiments, the initiator is light in the visible spectrum. In certain embodiments, the light has a wavelength from about 380 nm to about 750 nm. In certain embodiments, wherein the initiator is heat. In certain embodiments, the heat is a temperature of about 60° C. to about 80° C.

In certain embodiments of the methods, $R^{1a}$, $R^{1b}$ and $R^{1c}$ are each independently selected from the group consisting of $C_{3-8}$ cycloalkyl, $C_{2-8}$ heterocyclyl, linear or branched $C_{1-6}$ alkyl, —CN, and —C(═O)-Q-$R^{10}$.

In certain embodiments of the methods, at least one of $R^{1a}$, $R^{1b}$ and $R^{1c}$ is a linear or branched $C_{1-6}$ alkyl.

In certain embodiments of the methods, each of $R^{1a}$, $R^{1b}$ and $R^{1c}$ is methyl.

In certain embodiments of the methods, the compound is a structure of Formula II:

II

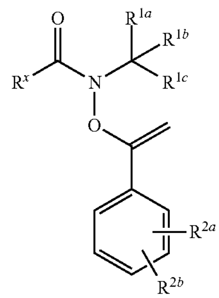

wherein, $R^{2a}$ and $R^{2b}$ are each independently selected from the group consisting of hydrogen, halo, optionally substituted linear or branched $C_{1-10}$ alkyl, —CN, $C_{1-6}$ alkoxy, —$NO_2$, —$NR^aR^b$, —(C═O)$OR^c$ and —(C═O)$R^c$, wherein, $R^a$, $R^b$ and $R^c$ are each independently selected from the group consisting of hydrogen, methyl, ethyl, propyl and butyl.

In certain embodiments of the methods, in Formula II, $R^{2a}$ and $R^{2b}$ are each hydrogen.

In certain embodiments of the methods, in Formula II, $R^x$ is selected from the group consisting of —$CF_3$, methyl, t-butyl and optionally substituted phenyl. In certain embodiments of the methods, in Formula II, $R^x$ is an optionally substituted phenyl.

In certain embodiments of the methods, in Formula II, the optionally substituted phenyl has the structure:

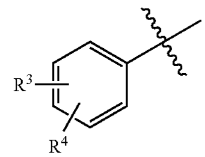

wherein, $R^3$ and $R^4$ are each independently selected from the group consisting of halo-$C_{1-6}$ alkyl, halo, —CN, and —$NO_2$.

In certain embodiments of the methods, in Formula II, at least one of $R^3$ and $R^4$ is halo-$C_{1-6}$ alkyl.

In certain embodiments of the methods, in Formula II, $R^3$ is selected from the group consisting of F, Cl, —$CF_3$, —$CHF_2$ and $CH_2F$.

In certain embodiments of the methods, in Formula II, $R^4$ is selected from the group consisting of F, Cl, —$CF_3$, —$CHF_2$ and $CH_2F$.

In certain embodiments of the methods, in Formula II, the halo-$C_{1-6}$ alkyl is $CF_3$.

In certain embodiments of the methods, the compound is a structure of Formula III:

III

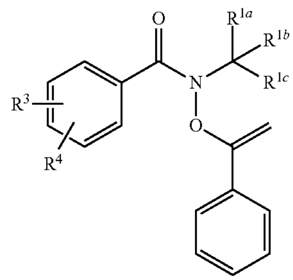

wherein, $R^3$ and $R^4$ are each independently selected from the group consisting of halo-$C_{1-6}$ alkyl, halo, —CN, and —$NO_2$.

In certain embodiments of the methods, in Formula III, each of $R^{1a}$, $R^{1b}$ and $R^{1c}$ is methyl.

In certain embodiments of the methods, in Formula III, at least one of $R^3$ and $R^4$ is halo-$C_{1-6}$ alkyl.

In certain embodiments of the methods, in Formula III, $R^3$ is selected from the group consisting of F, Cl, —$CF_3$, —$CHF_2$ and $CH_2F$.

In certain embodiments of the methods, in Formula III, $R^4$ is selected from the group consisting of F, Cl, —$CF_3$, —$CHF_2$ and $CH_2F$.

In certain embodiments of the methods, in Formula III, the halo-$C_{1-6}$ alkyl is $CF_3$.

In certain embodiments of the methods, in Formula III, the compound has the structure:

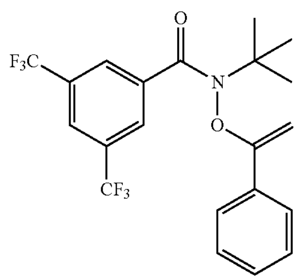

In certain embodiments of the methods, the trap comprises a transfer group X is selected from the group consisting of:

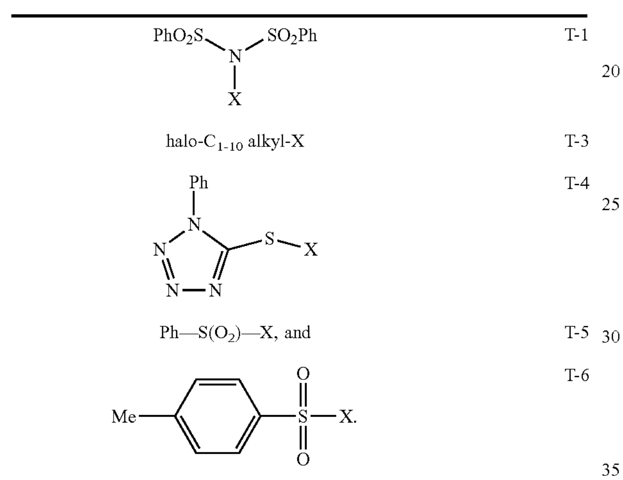

| | |
|---|---|
| | T-1 |
| halo-$C_{1-10}$ alkyl-X | T-3 |
| | T-4 |
| Ph—$S(O_2)$—X, and | T-5 |
| | T-6 |

In certain embodiments of the methods, in the trap, X is selected from the group consisting of halogen, —S—$C_{3-8}$ heteroaryl which can be optionally substituted, —$C_{3-8}$ heteroaryl which can be optionally substituted, —S-(halo-$C_{1-6}$ alkyl), —S-Ph, —$NO_2$, —CN, and

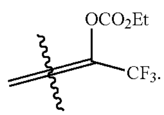

In certain embodiments of the methods, in the trap, the halo-$C_{1-10}$ alkyl-X is selected from the group consisting of $F_{13}C_6$—X, $F_{17}C_8$—X and $Cl_3C$—X.

In certain embodiments of the methods, in the trap, X is selected from $C_1$, Br and I.

In certain embodiments of the methods, the polymer comprises post-industrial or post-consumer polymers.

In certain embodiments of the methods, the polymer is a polyethylene.

In certain embodiments of the methods, a property of the substrate is modified.

In certain embodiments of the methods, the modified property is one or more properties selected from the group consisting of solubility, glass transition temperature, crystallinity, viscosity, adhesion, melting temperature, clarity, chemical stability, degradation rate, phase behavior, storage modulus, flexural modulus, yield stress, impact strength, Young's modulus, strain at break and tensile toughness. Each of these properties is known in the art and can be measured using standard techniques.

In certain embodiments, the subject matter described herein is directed to a modified substrate prepared by the method of claim 26.

In certain embodiments, the yield is above 20%, or above 30%, or above 40%, or above 50%, or above 60%, or above 70%, or above 80%, or above 90%, or above 96%, or from about 20% to about 90% or from about 40% to about 80%, or from about 60% to about 70%.

Scheme A depicts a general synthetic approach to certain embodiments of C—H functionalization described fully herein:

Scheme A

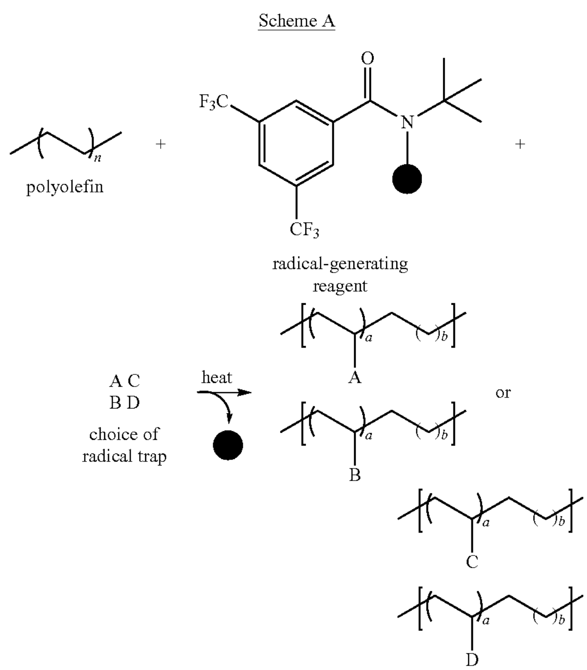

Scheme B depicts synthetic approaches specifically for heteroarylation of unactivated aliphatic C—H bonds. C—H heteroarylation of diverse substrates using 2-(methylsulfonyl)benzothiazole as coupling partner. All yields are of isolated product. Regio- and diastereoselectivities were determined by $^1H$ NMR spectroscopy of crude reaction mixture. Percent functionalization values are provided in examples containing regioisomeric mixtures.

Scheme B

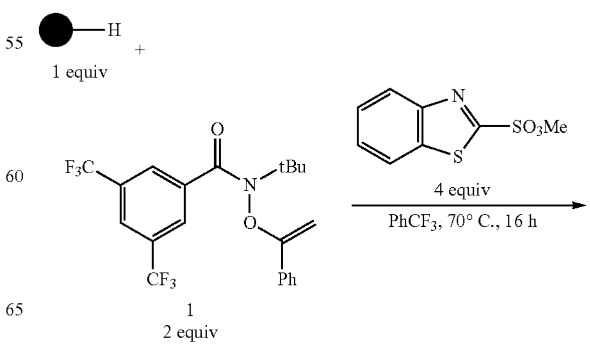

-continued
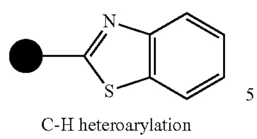
C-H heteroarylation
Simple Substrates
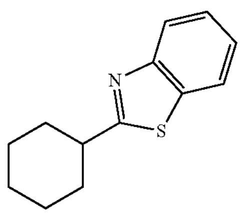
2
75% yield
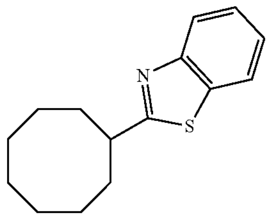
3
61% yield
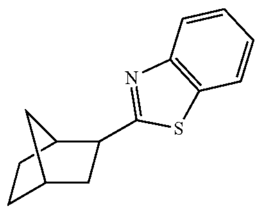
4
58% yield
>20:1 dr
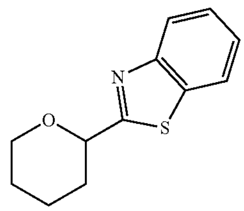
7
47% yield
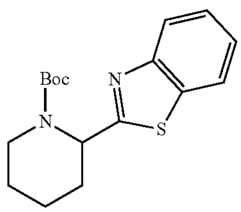
8
91% yield
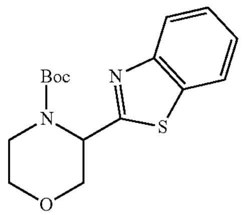
9
86% yield
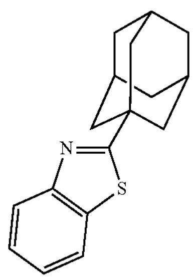
5
62% yield
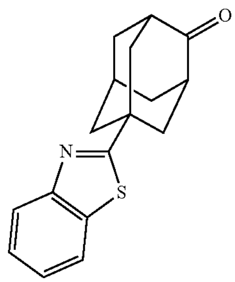
6
34% yield
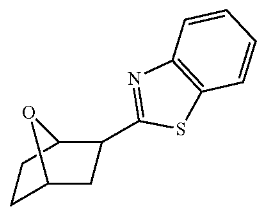
10
39% yield
>20:1 dr
-continued
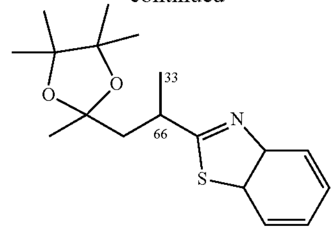
11
45% yield[a]
LSF of Complex Substrates
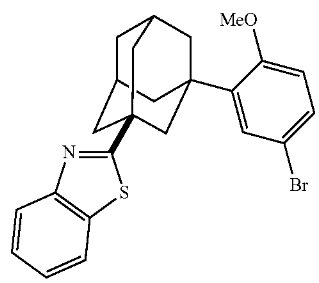
12
54% yield[a]
from differin precursor
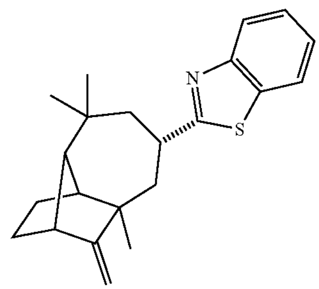
13
37% yield
>20:1 dr
from (+)-longifolene precursor
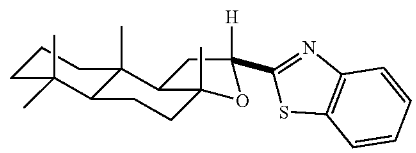
14
45% yield
>20:1 dr
from (-)-ambroxide precursor
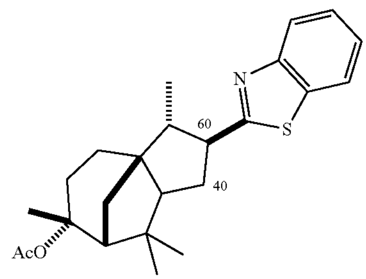
15
55% yield
>20:1 dr
from cedryl acetate -continued

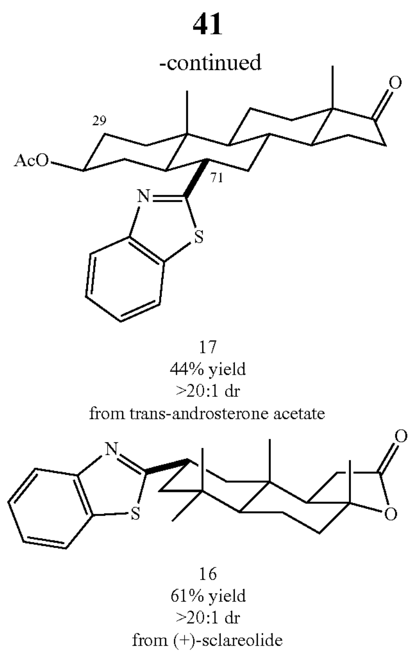

17
44% yield
>20:1 dr
from trans-androsterone acetate 16
61% yield
>20:1 dr
from (+)-sclareolide Despite many impressive achievements in the field, there are important C—H transformations which remain inaccessible. A clear example is the direct, site-selective $C(sp^3)$-heteroarylation of unactivated, aliphatic C—H bonds. Such a process would offer a remarkably concise way to introduce synthetically and medicinally relevant heterocycles onto small molecule substrates, while obviating the preparation of functionalized aliphatic coupling partners commonly used in metal-catalyzed processes to deliver $C(sp^3)$-$C(sp^2)$ cross-coupled products. (75) In contrast to the heteroarylation of weaker C—H bonds (FIG. 1), functionalization of strong aliphatic C—H bonds has been a challenge. MacMillan and co-workers reported the first examples of such a transformation via nickel-polyoxometalate dual catalysis and aryl halide coupling partners. (76) While impressively broad in scope, excess C—H substrate was required in all cases-suboptimal in late-stage contexts where the starting material is precious. Several other approaches to aliphatic C—H heteroarylation have been reported, including cross-dehydrogenative couplings (77), Minisci-type additions (78), and homolytic aromatic substitutions. (79) These transformations also require the use of excess substrate and feature non-selective HAT reagents. In addition, Minisci-type C—H heteroarylations can suffer from poor regio- and chemoselectivity in the radical addition, leading to mixtures of products. (80)

As disclosed herein, several sulfonyl functionalization reagents were used which generated the sulfonyl radical to facilitate chain transfer and afford the desired product. We hypothesized that using readily accessed heteroaromatic sulfones as radical traps could lead to a direct heteroarylation of aliphatic C—H bonds via homolytic aromatic substitution. Herein, we report the successful development of such a process, enabling the direct heteroarylation of a range of aliphatic substrates-used as limiting reagent in all cases and thus ideal for the late-stage functionalization of complex molecules.

Compounds disclosed herein may be synthesized by synthetic routes that include processes analogous to those well-known in the chemical arts, particularly in light of the description contained herein. Starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie,* 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

The General Procedures and Examples provide exemplary methods for preparing compounds. Those skilled in the art will appreciate that other synthetic routes may be used to synthesize the compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds described herein, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, phthalimide (Phth), t-butoxycarbonyl (Boc), benzyloxycarbonyl (Cbz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

The following examples are offered by way of illustration and not by way of limitation.

EXAMPLES

General Methods and Materials: Proton, carbon, and fluorine magnetic resonance spectra ($^1H$ NMR, $^{13}C$ NMR, and $^{19}F$ NMR) were recorded on a Bruker model DRX 400 MHz, Bruker 500 MHz, or Bruker AVANCE III 600 MHz CryoProbe spectrometer with solvent resonance as the internal standard ($^1H$ NMR: CDCl3 at 7.26 ppm; $^{13}C$ NMR: CDCl3 at 77.16 ppm). $^1H$ NMR data are reported as follows: chemical shift, multiplicity (s=singlet, d=doublet, t=triplet, q=quartet, m=multiplet, dd=doublet of doublets, dt=doublet of triplets, bs=broad singlet), coupling constants (Hz), and integration.

High temperature NMR (HT NMR) was recorded on a Bruker 500 MHz spectrometer at 110° C. with solvent resonance as the internal standard ($^1H$ NMR: C2D2Cl4 at 6.00 ppm; $^{13}C$ NMR: C2D2Cl4 at 73.78 ppm). In all experiments, an ethylene glycol standard confirmed the temperature of the NMR, roughly 116° C. in all cases, and the delay time was set to 5 sec (d1=5). 1H NMR data are reported as follows: chemical shift, multiplicity (s=singlet, d=doublet, t=triplet, q=quartet, dd=doublet of doublets, ddd=doublet of doublet of doublets, td=triplet of doublets, tdd=triplet of doublet of doublets, qd=quartet of doublets, m=multiplet), coupling constants (Hz), and integration.

GC spectra were obtained using a Shimadzu GC-2010 gas chromatograph with a Shimadzu AOC-20s Autosampler, and Shimadzu SHRXI-5 MS GC column. Four different GC methods are used. Method 1: Initial temperature of 30.0° C., ramping at 2.0° C./min until 75.0° C., holding for 1.0 min, then ramping at 30.0° C./min until 250.0° C., and holding for 2.0 min. Method 2: Initial temperature of 55.0° C., ramping at 2.0° C./min until 95.0° C., then ramping at 30.0° C./min until 250.0° C., and holding for 2.0 min. Method 3: Initial temperature of 55.0° C., ramping at 3.0° C./min until 120.0° C., then ramping at 30.0° C./min until 250.0° C., and holding for 2.0 min. Method 4: Initial temperature of 55.0° C., ramping at 15.0° C./min until 200.0° C., then ramping at 3.0° C./min until 250.0° C., and holding for 2.0 min. The results of the kinetic isotope study were analyzed using an Agilent Gas Chromatograph-Mass Spectrometer with a 7820A series GC system and a 5977E Mass Selective Detector.

Infrared (IR) spectra were obtained using PerkinElmer Frontier FT-IR spectrometer. Thin layer chromatography (TLC) was performed on SiliaPlate 250 μm thick silica gel plates provided by Silicycle. Visualization was accomplished with short wave UV light (254 nm), iodine, aqueous basic potassium permanganate solution, or aqueous acidic ceric ammonium molybdate solution followed by heating. Flash chromatography was performed using SiliaFlash P60 silica gel (40-63 μm) purchased from Silicycle, or using a Biotage™ Isolera auto-column with silica gel purchased from Biotage. Tetrahydrofuran, diethyl ether, and dichloromethane were dried by passage through a column of neutral alumina under nitrogen prior to use. Irradiation of reactions was performed using two Kessil KSH150B Blue 34W LED Grow Lights with fan cooling. UV light experiments were performed in a Luzchem LZC-ORG photoreactor containing UVA lamps. All other reagents were obtained from commercial sources and used without further purification unless otherwise noted. In addition, all reactions were carried out under an atmosphere of argon in flame or oven-dried glassware with magnetic stirring unless otherwise noted.

Mass spectra were obtained via one of 3 methods: with a Q Exactive HF-X (ThermoFisher, Bremen, Germany) mass spectrometer with samples introduced via a heated electrospray source (HESI) or via an atmospheric pressure chemical ionization (APCI) source at a flow rate of 20 μL/min, or with a ThermoFisher GC Exactive with an Electron Ionization (EI) source.

All post-polymerization modifications were performed under inert atmosphere using standard glove box and Schlenk-line techniques. Commercial polyolefins were obtained from their respective companies and purified prior to use by precipitation into methanol or acetone. The company and lot number are named in the individual procedures. 1,2-Dichlorobenzene was degassed with argon through multiple freeze-pump-thaw cycles. Chlorobenzene was distilled over calcium hydride, degassed through three freeze-pump-thaw cycles, and stored in a glove box. Reagents, unless otherwise specified, were purchased and used without further purification.

High temperature gel permeation chromatography (HT GPC) spectra were obtained using a Tosoh EcoSEC-HT GPC using TSKgel GMHHR-M columns. Trichlorobenzene (TCB) with 200 ppm dibutylhydroxytoluene (BHT) was the mobile phase and the flow rate was set to 1 mL/min. The instrument was calibrated using polystyrene standards in the range of 580 to 5,480,000 Da. A calibration curve was created using refractive index detection against the polystyrene standards in 2 mg/mL solutions of trichlorobenzene (TCB) at 140° C. for polyethylenes and polypropylenes. A tandem multi-angle light scattering (MALS) detector could also be employed on the HT GPC via a Wyatt DAWN 8 heated flow cell instrument.

Differential scanning calorimetry (DSC) was used to determine the thermal characteristics of the polyolefins using a TA Instruments DSC (Discovery Series). The DSC measurements were performed on 1-10 mg of polymer samples at a temperature ramp rate of 10° C./min. Data was taken from the second thermal scanning cycle. Thermal gravimetric analysis (TGA) was obtained using a TA Instruments TGA (Discovery Series) in the temperature range of 40-600° C. at temperature ramp rate of 10° C./min. The temperature of decomposition (Td) was defined by the temperature at which 10% of total mass was lost.

Example 1: Alkenylhydroxyamide Synthesis

Scheme 1

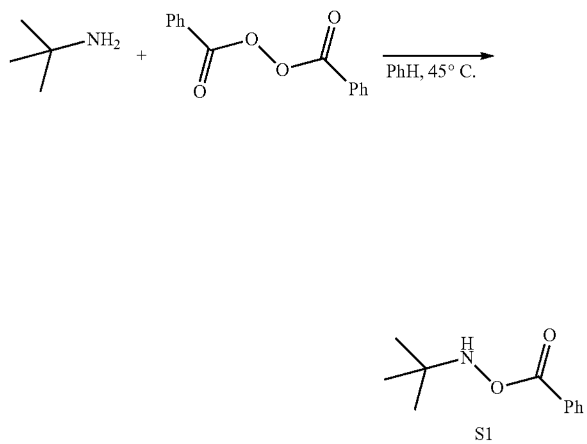

S1

N-(tert-butyl)-O-benzoylhydroxylamine (S1): Compound similar to previously reported procedure. To a flame dried round bottom flask with stir bar was added benzoyl peroxide (10.0 g, 41.3 mmol), dissolved in benzene (58 mL). Reaction scaled and placed under $N_2$. Roughly 60% of total volume of tert-butylamine (10.5 mL) added through septum, reaction heated at 45° C. for 1 hour, noting color change from cloudy white color to cloudy Carolina blue. After 1 h, remaining amount of tert-butylamine (6.9 mL, to total of 17.4 mL, 165 mmol) added through septum; reaction let heat overnight. At end, reaction let cool to room temperature, reaction diluted with diethyl ether, solid amine salt filtered off. Filtrate mixed with acidic aqueous $FeSO_4$ in ~1M $H_2SO_4$, stirred 10 minutes. Reaction transferred to separatory funnel, organic layer separated, washed saturated sodium bicarbonate solution (3×50 mL), water (1×50 mL), dried over $MgSO_4$, filtered and concentrated to afford product S1 as yellow oil (8.0 g, quantitative yield) in accordance with reported spectral data; compound used directly without purification.

Scheme 2

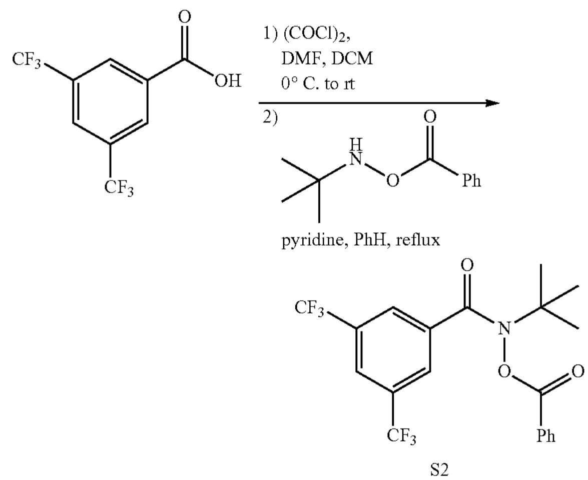

S2

N-(tert-butyl)-O-benzoyl-(3,5-bis-trifluoromethyl)-hydryoxyamide (S2): To a flame dried round bottom flask with stir bar was added (3,5-bis-trifluoromethyl)-benzoic acid (8.52 g, 33.0 mmol), dissolved in dichloromethane (55 mL). Dimethylformamide added (13 μL), reaction sealed, taped, equipped with $N_2$ line, brought to 0° C. Oxalyl chloride added dropwise via syringe (5.6 mL, 66.0 mmol), reaction stirred at 0° C. 15 minutes, then let come to room temp. Reaction let stir until cloudy white solution completely dissolved, forming a clear yellow solution, and bubbling completely subsided (~3 hours). At end, reaction carefully concentrated in vacuo to remove all volatiles. Yellow oil taken up in benzene (60 mL), benzoylhydroxylamine (S1) added (7.02 g, 36.3 mmol) in minimal amount of benzene. Pyridine added (5.61 mL, 69.3 mmol), flask equipped with condenser, brought to reflux overnight. At end of reaction, mixture allowed to cool to room temperature, diluted with diethyl ether, pyridinium salt filtered off. Filtrate was transferred to separatory funnel, washed with 1 M hydrochloric acid (2×100 mL), water, dried over $MgSO_4$, filtered and concentrated to afford product S2 as amber-colored solid (14.2 g, 99% yield). Used directly in next step.

$^1$H NMR (600 MHz, $CDCl_3$) δ 8.03 (s, 1H), 7.82 (d, 2H), 7.76 (s, 1H), 7.59 (t, 1H), 7.41 (t, 2H), 1.62 (s, 9H), $^{13}$C NMR (151 MHz, $CDCl_3$) δ 167.5, 165.2, 137.5, 134.6, 131.3 (q), 129.6, 128.8, 127.89, 125.7, 123.6, 121.9, 63.8, 27.5

$^{19}$F NMR (376 MHz, $CDCl_3$) δ −63.0

HRMS (HESI) Exact mass calcd for $C_{20}H_{17}F_6NO_3H$ $[M+H]^+$, 434.1191. Found 434.1180.

Scheme 3

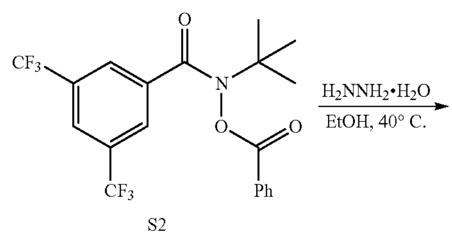

S2

-continued

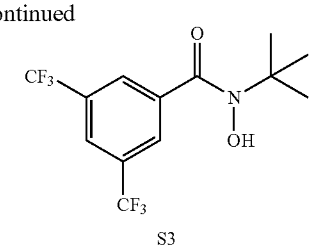

S3

N-(tert-butyl)-(3,5-bis-trifluoromethyl)-hydroxyamide (S3): To a large round bottom flask with magnetic stir bar was added O-benzoylhydroxyamide S2 (14.25 g, 32.88 mmol), dissolved in ethanol (106 mL), reaction capped and sealed with Teflon tape, equipped with $N_2$ line. Hydrazine monohydrate (11.96 mL, 246.6 mmol) added dropwise, reaction heated to 40° C. for 1.5 hours. At end of reaction, mixture let cool to room temp, then brought to 0° C. Ice water added to mixture (~1.5× volume of ethanol used), inducing precipitation of white solid from yellow solution. Reaction kept at 0° C. 5 minutes, then solid collected by filtration, washed with water then pentanes, dried thoroughly on hi-vac overnight to afford hydroxyamide product S3 (9.90 g, 91% yield). Used directly in next step.

$^1$H NMR (600 MHz, $CDCl_3$) δ 8.00 (s, 2H), 7.96 (s, 1H), 6.68 (br s, 1H), 1.49 (s, 9H), $^{13}$C NMR (151 MHz, $CDCl_3$) δ 167.6, 138.5, 131.6, 131.3, 128.1, 123.8, 123.6, 122.0, 62.2, 27.8

$^{19}$F NMR (376 MHz, $CDCl_3$) δ −62.9

HRMS (HESI) Exact mass calcd for $C_{13}H_{13}F_6NO_2H$ $[M+H]^+$, 330.0929. Found 330.0918.

Scheme 4

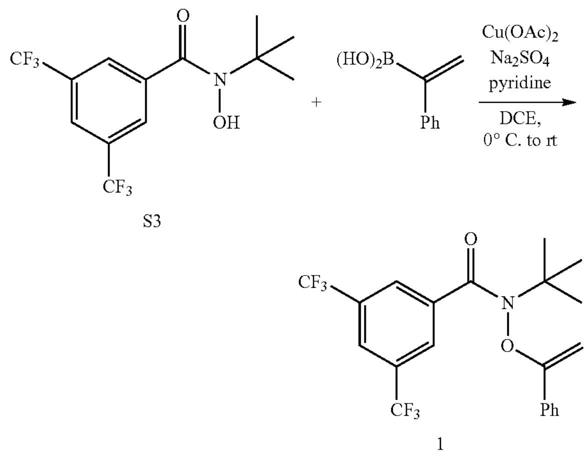

S3

1

N-(tert-butyl)-O-(1-phenylvinyl)-(3,5-bis-trifluoromethyl)-hydryoxyamide (1): Procedure adapted from report by Rovis and coworkers.[42] To a large, dry round bottom flask with stir bar was added copper acetate (2.76 g, 15.2 mmol), sodium sulfate (8.63 g, 60.7 mmol), hydroxamic acid S3 (5.00 g, 15.2 mmol). Mixture left open to ambient atmosphere; 1,2-dichloroethane added (200 mL) to make a slurry, mixture cooled to 0° C. Flask covered with aluminum foil, hood lights turned off. Pyridine added (3.70 mL, 45.6 mmol), mixture let come to room temperature overnight. Next morning, 1,1-phenylvinylboronic acid (4.49 g, 15.2 mmol) added, reaction let stir at room temperature under ambient atmosphere, monitored by TLC until no more product being formed (~4 days). At end of reaction, mixture filtered through short plug of silica gel with dichloromethane to remove solid sodium sulfate and copper acetate. Filtrate concentrated in vacuo, purified by silica gel column chromatography with 2% diethyl ether/hexanes ($R_f$~0.5 in 5% $Et_2O$/hexanes) to give product 1 as yellow solid (3.90 g, 59% yield). Stored in freezer in the dark, but could be weighed out in the light on the benchtop for future use. Note: when boronic acid added at beginning, reaction proceeded but a large amount of boronic-acid derived homodimer seen; pre-mixing and adding in boronic acid later reduced this byproduct and increased product yield.

$^1H$ NMR (600 MHz, $CDCl_3$) δ 8.06 (s, 2H), 7.82 (s, 1H), 7.33 (m, 1H), 7.27 (m, 4H), 4.83 (d, 1H), 4.76 (d, 1H), 1.69 (s, 9H)

$^{13}C$ NMR (151 MHz, $CDCl_3$) 169.4, 160.6, 138.2, 132.0, 131.3-130.6 (q, $CF_3$), 129.4, 128.3, 127.3

(d), 125.6-120.2 (q), 125.1, 123.3 (p), 87.3, 64.2, 27.5

$^{19}F$ NMR (376 MHz, $CDCl_3$) δ −63.0

HRMS (HESI) Exact mass calcd for $C_{21}H_{19}F_6NO_2H$ $[M+H]^+$, 432.1398. Found 432.1387.

Scheme 5

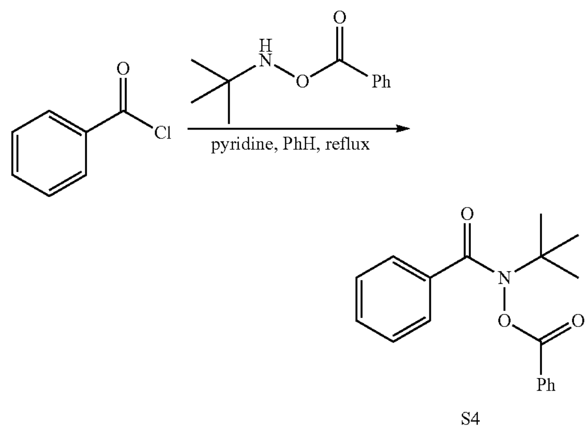

S4

N-(tert-butyl)-O-benzoyl-phenyl-hydroxyamide (S4): To a flame dried round bottom flask with stir bar was added benzoyl chloride (0.82 mL, 7.1 mmol), dissolved in benzene (20 mL), benzoylhydroxylamine (S1) added (1.5 g, 7.8 mmol). Pyridine added (1.4 mL, 17 mmol), flask equipped with condenser, brought to reflux overnight. At end of reaction, mixture allowed to cool to room temperature, diluted with diethyl ether, pyridinium salt filtered off. Filtrate was transferred to separatory funnel, washed with 1 M hydrochloric acid (2×100 mL), water, dried over $MgSO_4$, filtered and concentrated to afford product S4 as white solid (2.1 g, 99% yield). Used directly in next step.

$^1H$ NMR (600 MHz, $CDCl_3$) δ 7.81 (dm, 2H), 7.56 (m, 3H), 7.40 (m, 2H), 7.26 (m, 3H), 1.62 (s, 9H)

$^{13}C$ NMR (151 MHz, $CDCl_3$) δ 171.6, 165.5, 136.1, 133.9, 129.9, 129.6, 128.6, 127.8, 127.1, 126.8, 63.0, 27.6

HRMS (HESI) Exact mass calcd for $C_{18}H_{19}NO_3H$ $[M+H]^+$, 298.1443. Found 298.1433.

Scheme 6

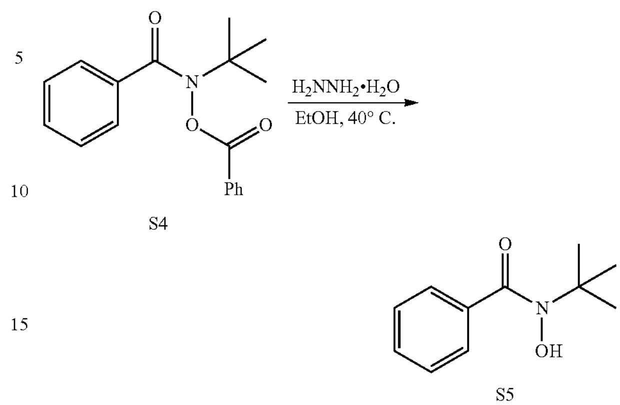

S4

S5

N-(tert-butyl)-phenyl-hydryoxyamide (S5): To a large round bottom flask with magnetic stir bar was added O-benzoylhydroxyamide S4 (2.11 g, 7.10 mmol), dissolved in ethanol (18 mL), reaction capped and sealed with Teflon tape, equipped with $N_2$ line. Hydrazine monohydrate (2.58 mL, 53.2 mmol) added dropwise, reaction heated to 40° C. for 1.5 hours. At end of reaction, mixture let cool to room temp, reaction concentrated in vacuo, purified by silica gel column chromatography (15% EtOAc/hexanes, $R_f$=0.10) to afford hydroxyamide product S5 (0.90 g, 66% yield). Used directly in next step.

$^1H$ NMR (600 MHz, $CDCl_3$) δ 8.73 (br s, 1H), 7.38 (m, 3H), 7.28 (m, 2H), 1.37 (s, 9H)

$^{13}C$ NMR (151 MHz, $CDCl_3$) δ 170.5, 136.3, 129.8, 127.8, 127.6, 61.6, 28.0

HRMS (HESI) Exact mass calcd for $C_{11}H_{15}NO_2H$ $[M+H]^+$, 194.1181. Found 194.1174.

Scheme 7

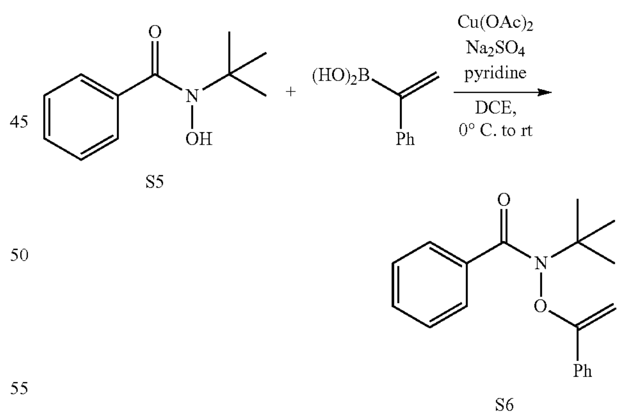

S5

S6

N-(tert-butyl)-O-(1-phenylvinyl)-phenyl-hydryoxyamide (S6): Procedure adapted from report by Rovis and coworkers.[42] To a large, dry round bottom flask with stir bar was added copper acetate (848 mg, 4.67 mmol), sodium sulfate (2.65 g, 18.7 mmol), hydroxamic acid S5 (0.902 g, 4.67 mmol). Mixture left open to ambient atmosphere; 1,2-dichloroethane added (80 mL) to make a slurry, mixture cooled to 0° C. Flask covered with aluminum foil, hood lights turned off. Pyridine added (1.10 mL, 14.0 mmol), mixture let come to room temperature overnight. Next morning, 1,1-phenylvinylboronic acid (1.38 g, 9.34 mmol) added, reaction let stir at room temperature under ambient atmosphere, monitored by TLC until no more product being formed (~4 days). At end of reaction, mixture filtered through short plug of silica gel with dichloromethane to remove solid sodium sulfate and copper acetate. Filtrate concentrated in vacuo, purified by silica gel column chromatography with 2% diethyl ether/hexanes ($R_f$ 0.15 in 5% $Et_2O$/hexanes) to give product S6 as yellow solid (0.70 g, 51% yield). Stored in freezer in the dark, but could be weighed out in the light on the benchtop for future use. Note: when boronic acid added at beginning, reaction proceeded but a large amount of boronic-acid derived homodimer seen; pre-mixing and adding in boronic acid later reduced this byproduct and increased product yield $^1H$ NMR (600 MHz, $CDCl_3$) δ 7.57 (d, 2H), 7.28 (m, 8H), 4.78 (d, 1H), 4.74 (d, 1H), 1.66 (s, 9H)

$^{13}C$ NMR (151 MHz, $CDCl_3$) δ 173.4, 160.9, 136.8, 133.1, 129.5, 129.0, 128.1, 127.5, 126.6, 125.6, 87.1, 63.5, 27.8

HRMS (HESI) Exact mass calcd for $C_{19}H_{21}NO_2H$ $[M+H]^+$, 296.1651. Found 296.1651.

Scheme 9

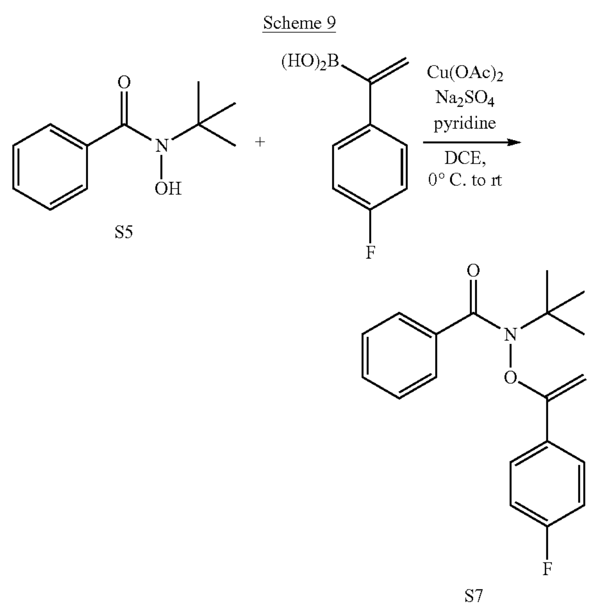

S5

S7

N-(tert-butyl)-O-(1-p-fluorophenylvinyl)-phenyl-hydryoxyamide (S7): Boronic acid synthesized by procedure described by Rovis and coworkers.[42] Then, to a large, dry round bottom flask with stir bar was added copper acetate (640 mg, 3.52 mmol), sodium sulfate (2.00 g, 14.1 mmol), hydroxamic acid S5 (0.681 g, 3.52 mmol). Mixture left open to ambient atmosphere; 1,2-dichloroethane added (35 mL) to make a slurry, mixture cooled to 0° C. Flask covered with aluminum foil, hood lights turned off. Pyridine added (0.85 mL, 10.6 mmol), mixture let come to room temperature overnight. Next morning, 1,1-p-fluorophenylvinylboronic acid (1.17 g, 7.05 mmol) added, reaction let stir at room temperature under ambient atmosphere, monitored by TLC until no more product being formed (~4 days). At end of reaction, mixture filtered through short plug of silica gel with dichloromethane to remove solid sodium sulfate and copper acetate. Filtrate concentrated in vacuo, purified by silica gel column chromatography with 4% diethyl ether/hexanes to give product S7 as yellow semisolid (0.28 g, 25% yield). Stored in freezer in the dark, but could be weighed out in the light on the benchtop for future use.

$^1H$ NMR (600 MHz, $CDCl_3$) δ 7.54 (d, 2H), 7.31 (m, 3H), 7.17 (dd, 2H), 6.94 (t, 2H), 4.77 (d, 1H), 4.68 (d, 1H), 1.65 (s, 9H)

$^{13}C$ NMR (151 MHz, $CDCl_3$) δ 173.5, 163.9, 162.2, 160.1, 136.8, 129.5, 129.2, 129.2, 127.5 (q), 115.1 (d), 87.0 (d), 63.5, 27.7

$^{19}F$ NMR (376 MHz, $CDCl_3$) δ −112.12

HRMS (HESI) Exact mass calcd for $C_{19}H_{21}FNO_2H$ $[M+H]^+$, 314.1556. Found 314.1548.

Scheme 9

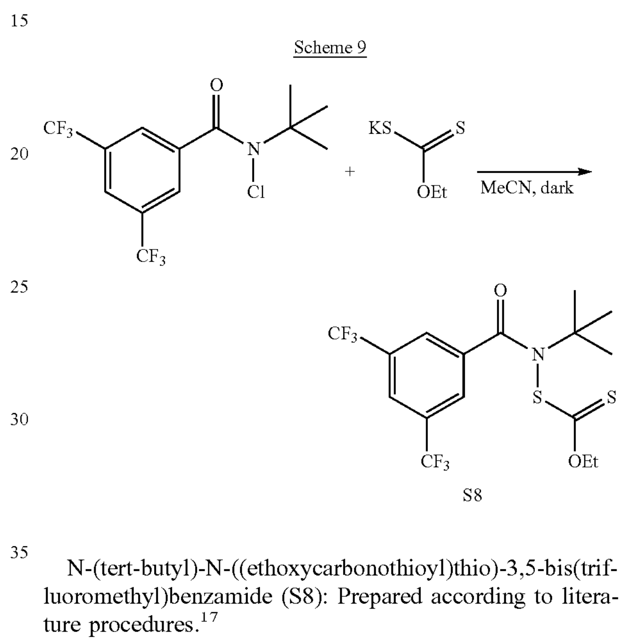

S8

N-(tert-butyl)-N-((ethoxycarbonothioyl)thio)-3,5-bis(trifluoromethyl)benzamide (S8): Prepared according to literature procedures.[17]

Scheme 10

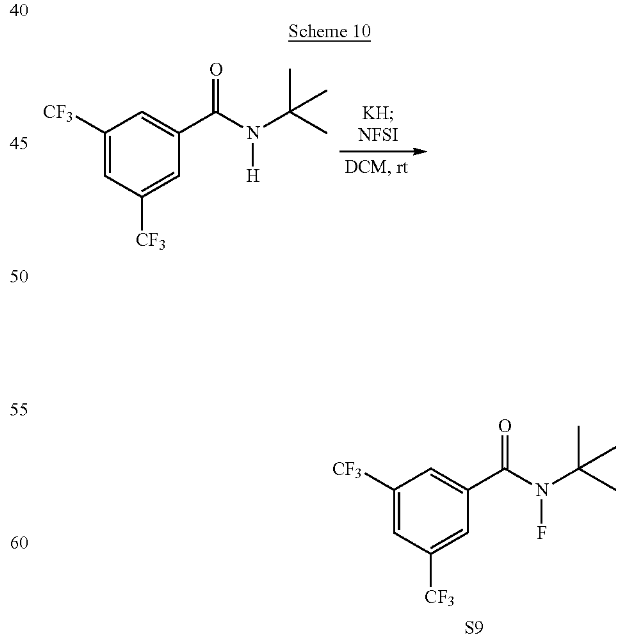

S9

N-(tert-butyl)-N-fluoro-3,5-bis(trifluoromethyl)benzamide (S9): Prepared according to literature procedures.[43]

Example 2: Reaction Conditions of C—H Fluorination
-continued
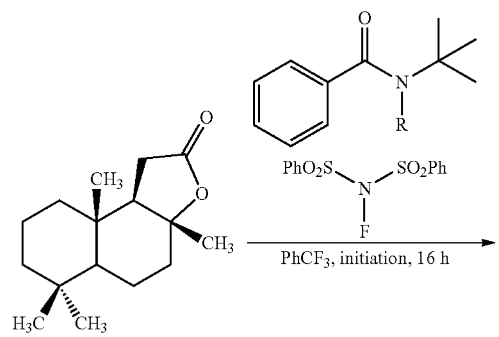
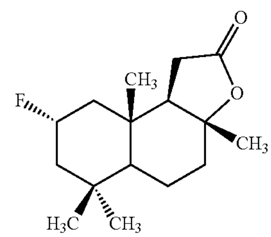
TABLE 2
| Entry | R group or reagent (equiv) | Equiv NFSI | Initiation | Conc. (M) | Yield (combined yield) (%)[a] |
|---|---|---|---|---|---|
| 1 | 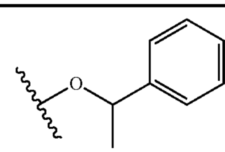 (1) | 2 | 440 nm BLED | 1 | 22 |
| 2 | 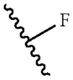 (1) | 2 | 440 nm BLED | 1 | 0 |
| 3 | 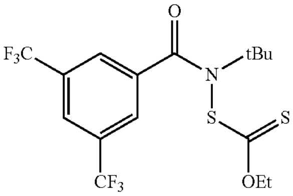 [SMILES: CCOC(=S)SN(C(=O)c1cc(C(F)(F)F)cc(C(F)(F)F)c1)C(C)(C)C] (1) | 2 | 440 nm BLED | 1 | 0 |
| 4 | 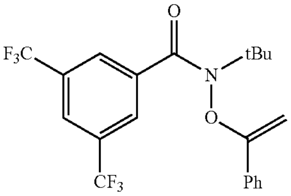 [SMILES: C=C(ON(C(=O)c1cc(C(F)(F)F)cc(C(F)(F)F)c1)C(C)(C)C)c1ccccc1] (1) | 2 | 440 nm BLED | 1 | 65 |
| 5 | 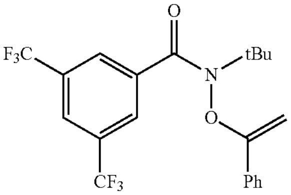 (2) | 2 | 440 nm BLED | 1 | 64 |

TABLE 2-continued
| Entry | R group or reagent (equiv) | Equiv NFSI | Initiation | Conc. (M) | Yield (combined yield) (%)[a] |
|---|---|---|---|---|---|
| 6 | 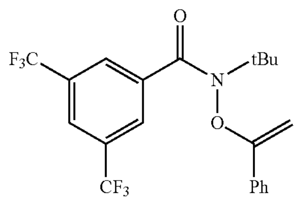 [SMILES: C=C(ON(C(=O)c1cc(C(F)(F)F)cc(C(F)(F)F)c1)C(C)(C)C)c1ccccc1] (2) | 4 | 440 nm BLED | 1 | 67 |
| 7 | 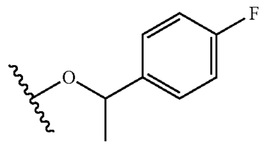 [SMILES: *OC(C)c1ccc(F)cc1] (1) | 2 | 440 nm BLED | 1 | 22 |
| 8 | 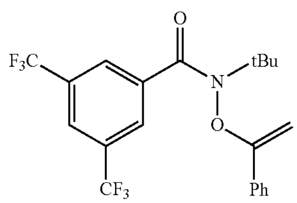 [SMILES: C=C(ON(C(=O)c1cc(C(F)(F)F)cc(C(F)(F)F)c1)C(C)(C)C)c1ccccc1] (2) | 2 | 427 nm BLED | 1 | 30 |
| 9 | 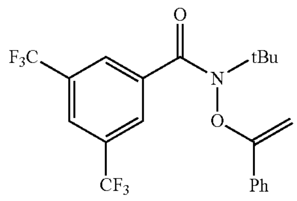 [SMILES: C=C(ON(C(=O)c1cc(C(F)(F)F)cc(C(F)(F)F)c1)C(C)(C)C)c1ccccc1] (2) | 2 | 60° C. | 1 | 67 |
| 10 | 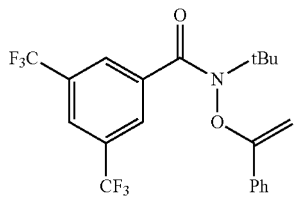 (2) | 2 | 70° C. | 1 | 74 |
| 11 | 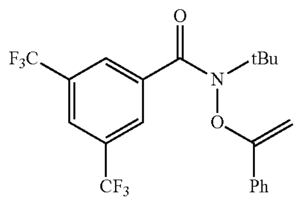 [SMILES: C=C(ON(C(=O)c1cc(C(F)(F)F)cc(C(F)(F)F)c1)C(C)(C)C)c1ccccc1] (2) | 2 | 80° C. | 1 | 58 |

TABLE 2-continued

| Entry | R group or reagent (equiv) | Equiv NFSI | Initiation | Conc. (M) | Yield (combined yield) (%)[a] |
|---|---|---|---|---|---|
| 12 | 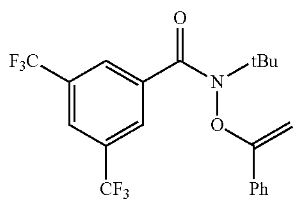 [SMILES: C=C(ON(C(=O)c1cc(C(F)(F)F)cc(C(F)(F)F)c1)C(C)(C)C)c1ccccc1] (2) | 2 | 70° C. | 0.5 | 57 |
| 13 | 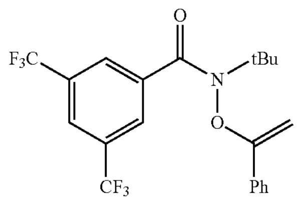 (2) | 2 | 70° C. | 1 | 56 |

[a]NMR yield versus hexamethyldisiloxane (HMDS) $^1$H NMR internal standard

[b]1 mmol reaction scale

Example 3: Syntheses of Substrate/Trap

Substrate traps were commercially available and used without further purification unless otherwise specified.

Scheme 11

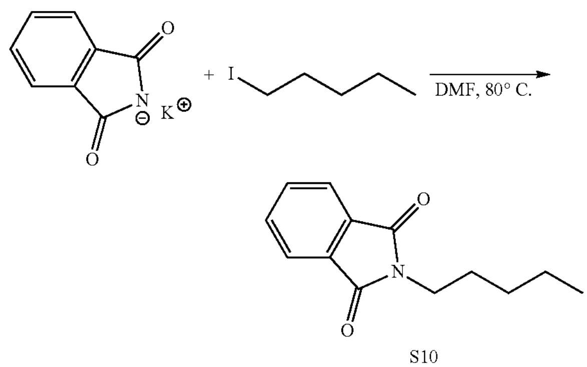

S10

N-Pentyl Phthalimide (S10): Prepared in accordance to literature procedure, giving product in accordance with literature values.[15]

Scheme 12

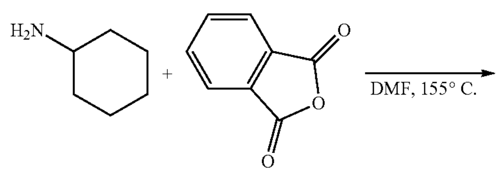

-continued

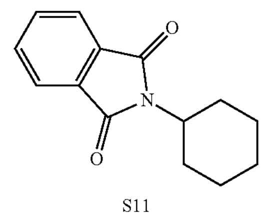

S11

N-Cyclohexyl Phthalimide (S11): Prepared in accordance to literature procedure, giving product in accordance with literature values.[15]

Scheme 13

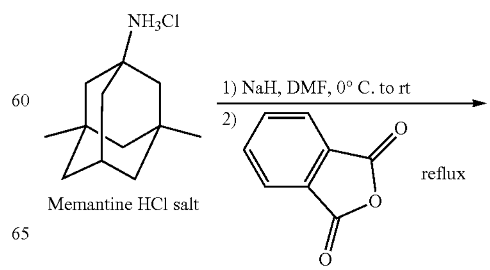

Memantine HCl salt

-continued

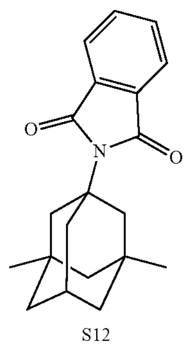

S12

N-Phthalimidyl Memantine (S12): Prepared in accordance to literature procedure, giving product in accordance with literature values.[15]

Scheme 14

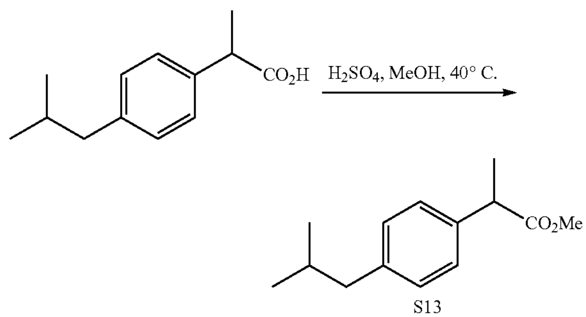

S13

Ibuprofen Methyl Ester (S13): Prepared in accordance to literature procedure, giving product in accordance with literature values.[44]

Scheme 15

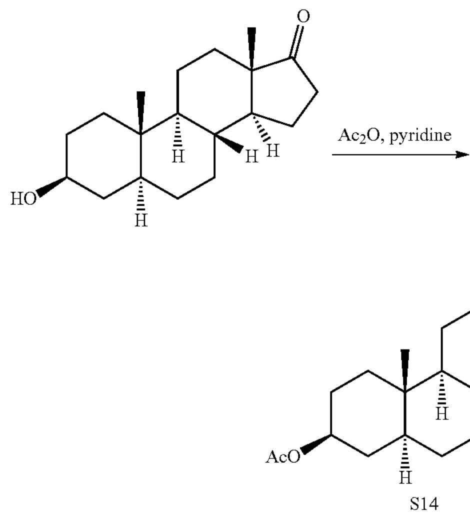

S14

Trans-androsterone Acetate (S15): Prepared in accordance to literature procedure, giving product in accordance with literature values.[45]

Scheme 16

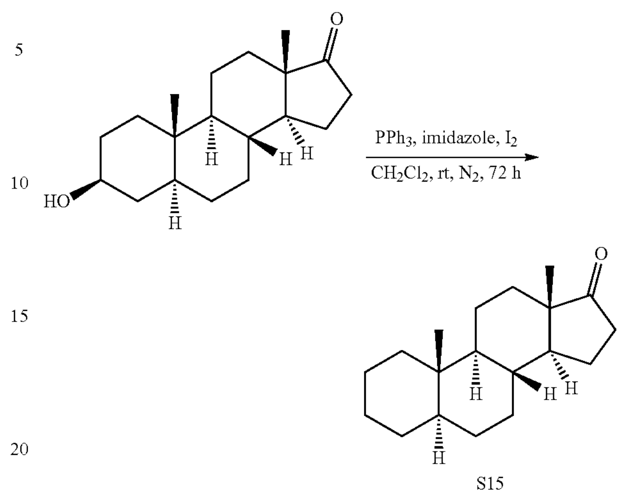

S15

Androstan-17-one (S15): Prepared in accordance to literature procedure, giving product in accordance with literature values.[46]

Scheme 17

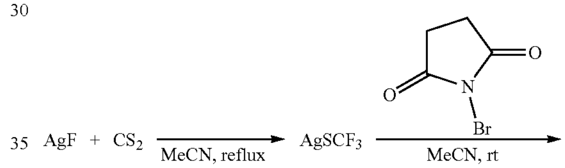

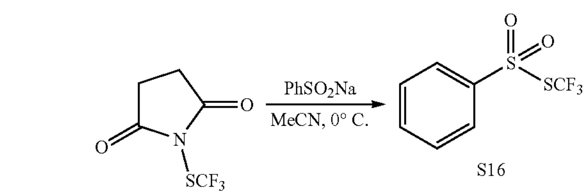

S16

(S)-trifluoromethyl benzenesulfonothionate (S16): Prepared in accordance to literature procedure, giving product in accordance with literature values.[47]

Scheme 18

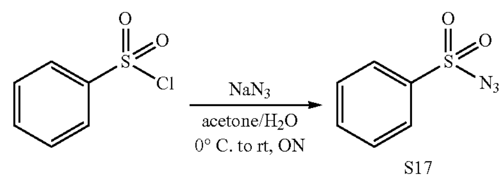

S17

Benzenesulfonyl azide (S17): Prepared in accordance to literature procedure, giving product in accordance with literature values.[48]

Scheme 19

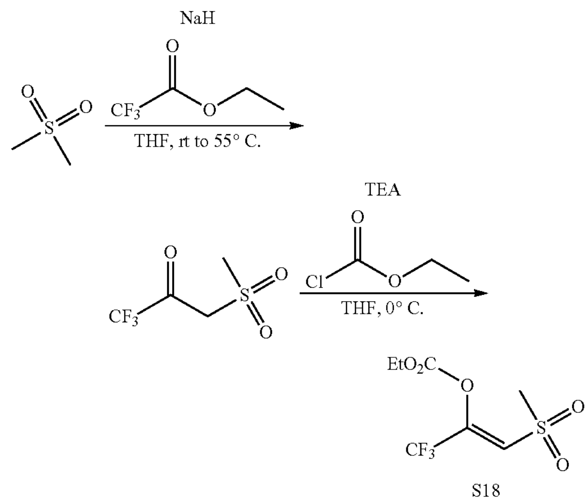

S18

Ethyl (3,3,3-trifluoro-1-(methylsulfonyl)prop-1-en-2-yl) carbonate (S18): Prepared in accordance to literature procedure, giving product in accordance with literature values.[49]

Scheme 20

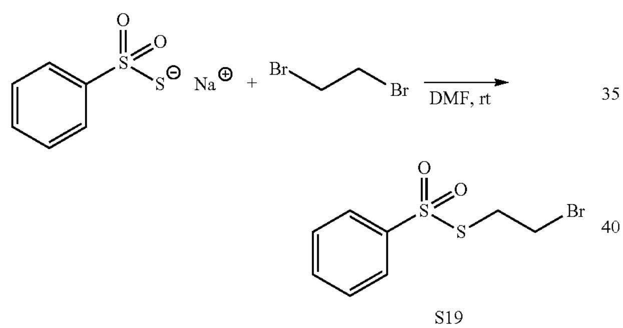

S19

S-(2-bromoethyl)benzenesulfonothioate (S20): To a flame-dried round bottom flask was added benzenethionosulfonic acid sodium salt (3.0 g, 15 mmol). Dry DMF (130 mL) was added to solubilize the salt. Once the thiosulfonate salt completely was dissolved via stirring, dibromoethane was added (3.3 mL, 38 mmol). The reaction was stirred at room temperature and was monitored by TLC. After 24 hours, more dibromoethane was added to the reaction (3.3 mL). After 2 days, the reaction was quenched with deionized water. The aqueous mixture was extracted with diethyl ether three times. The organic layer was washed with aqueous sodium bicarbonate and dried with magnesium sulfate. The product was concentrated in vacuo to yield the white flaky product (1.1 g, 26% yield).

$^{1}H$ NMR (400 MHz, $CDCl_3$) δ 7.95 (m, 2H), 7.67 (m, 1H), 7.60 (m, 2H), 3.53 (m, 2H), 3.39 (m, 2H).

$^{13}C$ NMR (151 MHz, $CDCl_3$) δ 144.4, 134.1, 129.6, 127.0, 37.2, 28.8.

HRMS (APCI) Exact mass calcd for $C_8H_9BrO_2S_2H$ $[M+H]^+$ 280.9306. Found, 280.9300.

Scheme 21

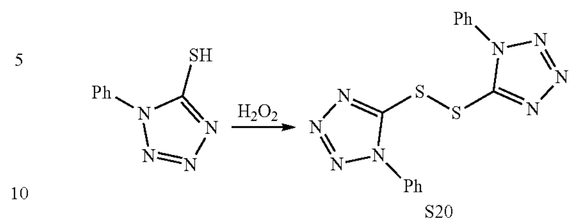

S20

1,2-bis(1-phenyl-1H-tetrazol-5-yl)disulfane (S20): Compound prepared according to a previously reported procedure.[50] To a round bottom flask equipped with a stir bar was added 1-phenyl-1H-tetrazole-5-thiol (17.8 g, 100 mmol), which was dissolved in EtOH (500 mL). The reaction was sealed and placed under $N_2$ atmosphere. 30% aqueous $H_2O_2$ (37.0 g, 33.3 ml, 3.26 eq.) was added. After 1 h, the formation of a white precipitate was observed and the reaction was allowed to run overnight for 16 h. At end, reaction was cooled to 0° C., and the white precipitate was collected via filtration with washing by cold diethyl ether. The disulfide was purified via recrystallization from a $CHCl_3$/EtOH mixture (2:3, ~500 ml). The pure product was filtered and obtained as a crystalline white-yellow solid (12.5 g, 70.4% yield) in accordance with reported spectral data; compound used directly without purification.

$^{1}H$ NMR (600 MHz, $CDCl_3$) δ 7.60 (m, 6H), 7.57 (m, 4H)

$^{13}C$ NMR (151 MHz, $CDCl_3$) 151.28, 132.99, 131.09, 130.11, 124.45

HRMS (APCI) Exact mass calcd for $C_{14}H_{10}N_8S_2$ $[M+H]^+$ 355.0548, Found, 355.0539.

Example 4: Independent Syntheses of Standards

Scheme 22

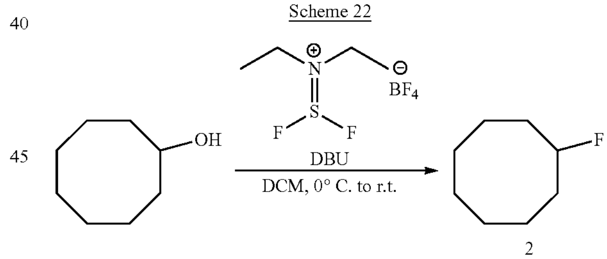

2

Cyclooctyl fluoride (2): To a solution of cyclooctanol (0.658 mL, 5.0 mmol) and DBU (1.14 g, 7.5 mmol) in 15 mL DCM at 0° C. was added XtalFluor-E (1.72 g, 7.5 mmol). Mixture stirred 30 minutes at 0° C., then warmed to room temperature and let stir until the disappearance of cyclooctanol was seen by TLC (visualized with CAM stain; note extended reaction times resulted in elimination of fluoride to cyclooctene). At the end of reaction, mixture quenched with 5% $NaHCO_3$ aqueous solution, let stir 15 minutes. The resulting mixture was extracted 2× with DCM, organic phases were combined, dried over $MgSO_4$, filtered over a pad of silica, and carefully concentrated. Reaction was then purified via column chromatography using a gradient of 0-10% $Et_2O$/pentanes to afford product 2 as a clear oil, in accordance with literature values.[51]

$^{1}H$ NMR (600 MHz, $CDCl_3$) δ 4.75 (dm, 1H), 1.95 (m, 4H), 1.76 (m, 2H), 1.60 (m, 8H)

$^{13}C$ NMR (151 MHz, $CDCl_3$) δ 95.4, 94.3, 32.2, 32.1, 27.2, 25.1, 22.1, 22.0

Scheme 23

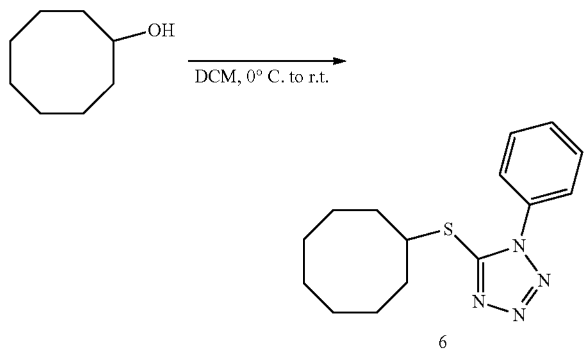

6

5-(cyclooctylthio)-1-phenyl-1H-tetrazole (6): Adapted from a literature procedure.[X] To a flame dried round bottom flask with stir bar was added cyclooctanol (641 mg, 0.658 ml, 5.00 mmol), triphenylphosphine (1.44 g, 5.50 mmol, 1.1 eq), and 5-mercapto-1-phenyltetrazole (980 mg, 5.50 mmol, 1.1 eq). THF (25 ml) were added and the solution was cooled to 0° C. DIAD (1.11 g, 1.07 ml, 5.50 mmol, 1.1 eq) was added dropwise to the mixture and the reaction was allowed to warm to room temperature and stir for 12 hrs. Upon completion of the reaction, the reaction mixture was concentrated and dry loaded onto silica and purified by column chromatography (2 to 5% Ether/Pentanes) to afford the pure thioether (531 mg, 1.84 mmol, 36.8% yield).

$^{1}H$ NMR (600 MHz, $CDCl_3$) δ 7.55 (m, 5H), 4.22 (m, 1H), 2.16 (m, 2H), 1.87 (m, 2H), 1.75 (m, 2H), 1.63 (m, 5H), 1.53 (m, 3H)

$^{13}C$ NMR (151 MHz, $CDCl_3$) δ 154.5, 133.9, 130.1, 129.8, 124.0, 49.2, 32.3, 27.0, 25.7, 25.0

HRMS (APCI) Exact mass cacld for $C_{15}H_{20}N_4S$ $[M+H]^+$ 289.1487. Found, 289.1478

Scheme 24

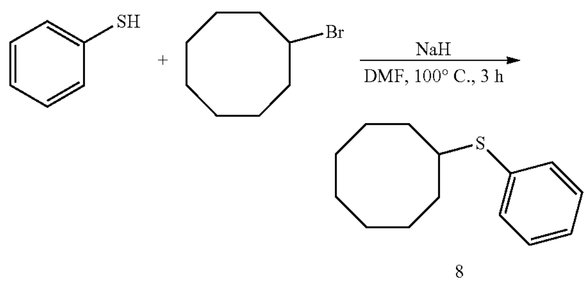

8

Cyclooctyl phenyl thioether (8): Prepared according to literature procedure, purified by silica gel chromatography with a gradient of 0% to 10% EtOAc in hexanes. Spectral data in accordance with literature values.[52]

$^{1}H$ NMR (600 MHz, $CDCl_3$) δ 7.40 (d, 2H), 7.31 (t, 2H), 7.22 (t, 1H), 3.42 (m, 1H), 1.99 (m, 2H), 1.78 (m, 2H), 1.70 (m, 2H), 1.56 (m, 8H)

$^{13}C$ NMR (151 MHz, $CDCl_3$) δ 136.1, 131.3, 128.8, 126.4, 47.6, 31.9, 27.1, 25.8, 25.1

Scheme 25

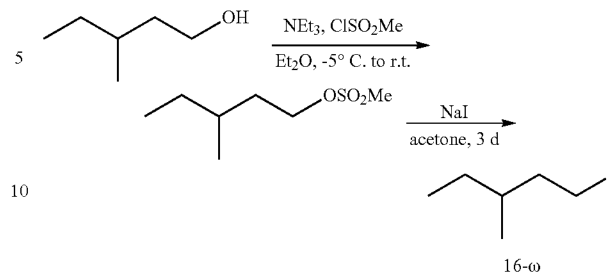

16-ω

3-methyl-1-iodo-pentane (16-ω): To a solution of 3-methyl-1-pentanol (0.704 mL, 5.68 mmol) and triethylamine (1.58 mL, 11.4 mmol) in 25 mL diethyl ether at −5° C. was added mesyl chloride dropwise (0.531 mL, 6.81 mmol). Mixture warmed to room temperature, let stir one hour. At end of reaction, mixture quenched with saturated $NaHCO_3$ solution, layers separated. Aqueous layer was extracted 2× with diethyl ether. Combined organics were washed with 1M HCl, water, brine, and dried over $MgSO_4$, filtered and concentrated to afford product as a clear, colorless oil. Product (1.02 g, 5.68 mmol) was then dissolved in 20 mL acetone, sodium iodide added (2.95 g, 19.7 mmol), let stir 3 days at room temperature. At end of the reaction, solvent mostly removed in vacuo, residue was taken up in water and extracted 3× with pentanes. Organics were washed with dilute $Na_2S_2O_3$ aqueous solution, brine, dried over $MgSO_4$, filtered and concentrated. Product was purified by Kuglerohr distillation if necessary to afford product 16 as clear, colorless oil with spectral data matching literature values.[53]

$^{1}H$ NMR (600 MHz, $CDCl_3$) δ 3.28 (m, 1H), 3.19 (m, 1H), 1.90 (m, 1H), 1.67 (m, 1H), 1.50 (m, 1H), 1.39 (m, 1H), 1.20 (m, 1H), 0.90 (m, 6H)

$^{13}C$ NMR (151 MHz, $CDCl_3$) δ 40.5, 35.4, 28.7, 18.2, 11.1, 5.4

Scheme 26

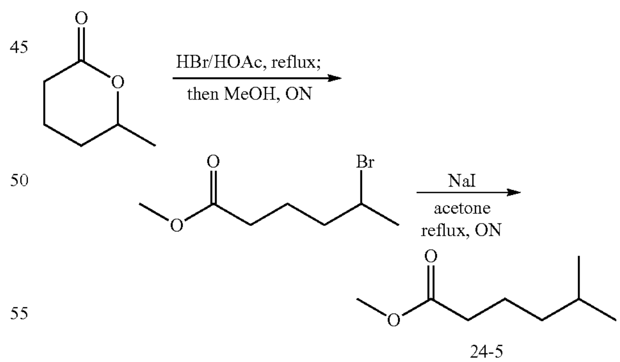

24-5

Methyl 5-Iodo-hexanoate (24-5): Adapted from literature precedent.[54] To a round bottom flask equipped with a condenser was added delta-hexalactone (2.00 g, 17.5 mmol), hydrobromic acid (1.66 mL), acetic acid (3.33 mL). Mixture heated to 70° C. for 4 hours, then let come to room temperature, methanol added (8 mL), let stir at room temperature overnight. At end of reaction, mixture was partially concentrated in vacuo, taken up in ethyl acetate, washed 3× with saturated aqueous sodium bicarbonate, brine, dried over $MgSO_4$, filtered and concentrated. Purified by column chromatography (5% EtOAc in hexanes), yielding alkyl bromide (0.86 g, 4.1 mmol). Product of step 1 (0.86 g, 4.1 mmol) was added to a flame dried round bottom flask with a stir bar, dissolved in 10 mL acetone, and charged with sodium iodide (2.16 g, 14.4 mmol), heated to reflux overnight. At the end of this reaction, mixture was partially concentrated in vacuo, residue was taken up in ethyl acetate, washed with saturated aqueous $Na_2S_2O_3$ solution, brine, dried over $MgSO_4$, filtered and concentrated. Purified via column chromatograph with 5% EtOAc in hexanes to yield methyl 5-iodo-hexanoate 24 (0.470 g, 1.84 mmol).

$^1H$ NMR (600 MHz, $CDCl_3$) δ 4.19 (m, 1H), 3.70 (s, 3H), 2.37 (td, 2H), 1.95 (d, 3H), 1.87 (m, 2H), 1.72 (m, 2H)

$^{13}C$ NMR (151 MHz, $CDCl_3$) δ 173.6, 51.6, 42.0, 33.0, 29.1, 28.8, 25.1

HRMS (HESI) Exact mass calcd for $C_7H_{13}IO_2H$ $[M+H]^+$, 257.0038. Found 257.0029.

Scheme 27

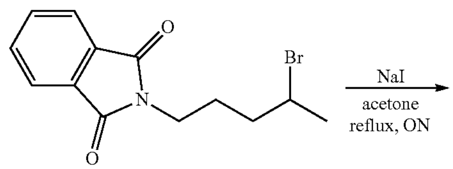

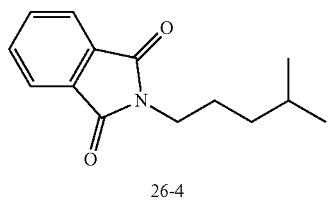

26-4

N-4-iodopentyl phthalimide (26-4): Bromide prepared according to literature precedent.[15] Substitution adapted from literature precedent.[54] Flame dried round bottom flask with stir bar was charged with bromide (0.500 g, 1.69 mmol), dissolved in 7 mL acetone, charged with sodium iodide (886 mg, 5.91 mmol), equipped with condenser. Mixture brought to reflux overnight. At the end of this reaction, mixture was partially concentrated in vacuo, residue was taken up in ethyl acetate, washed with saturated aqueous $Na_2S_2O_3$ solution, brine, dried over $MgSO_4$, filtered and concentrated. Purified via column chromatograph with a gradient of 5% to 20% EtOAc in hexanes to yield N-4-iodopentyl phthalimide (0.340 g, 0.99 mmol, 59% yield).

$^1H$ NMR (600 MHz, $CDCl_3$) δ 7.86 (m, 2H), 7.74 (m, 2H), 4.22 (m, 1H), 3.74 (t, 2H), 1.93 (d, 3H), 1.95-1.85 (m, 2H), 1.81 (m, 1H), 1.68 (m, 1H)

$^{13}C$ NMR (151 MHz, $CDCl_3$) δ 168.3, 134.0, 132.0, 123.3, 123.2, 39.7, 36.9, 28.9, 28.9, 28.7

HRMS (HESI) Exact mass calcd for $C_{13}H_{14}INO_2H$ $[M+H]^+$, 344.0147. Found 344.0137.

Scheme 28

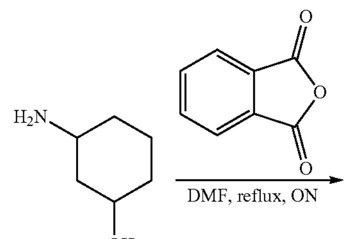

mixture of cis/trans

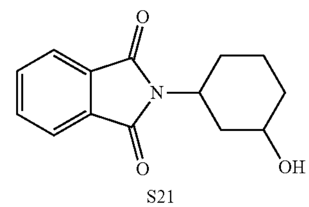

S21

1,3-oxycyclohexyl phthalimide (S21): To a dried round bottom flask was added aminoalcohol, DMF, phthalic anhydride. Equipped with a condenser and heated to reflux overnight. At the end of the reaction, mixture was cooled to room temp, diluted with ethyl acetate, and washed 2× with 1M HCl. Aqueous layer extracted with ethyl acetate, combined organics were dried over $MgSO_4$, filtered and concentrated. Further purification and separation of cis/trans isomers by silica gel chromatography (from 3:1:1 hexanes: DCM:EtOAc to 50% EtOAc in hexanes). Separate isomers then recrystallized from ethyl acetate to provide product S22 as a white solid, with spectral data in accordance to literature values.[55]

Scheme 29

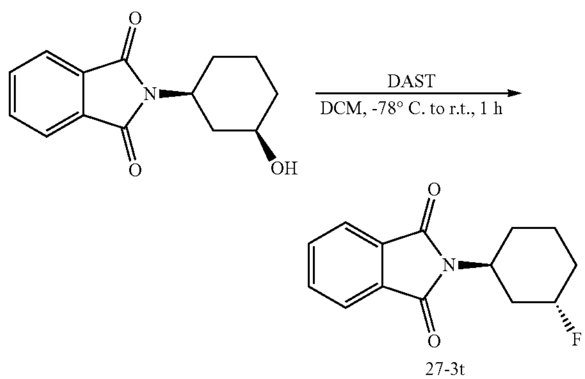

27-3t 1,3-trans fluorocyclohexyl phthalimide (27-3t): To a flame dried round bottom flask with stir bar was added aminoalcohol, DCM, cooled to −78° C. DAST (diethylaminosulfur trifluoride) was added dropwise, cooling bath removed and reaction let stir at room temperature for 1 hour (monitored by TLC for disappearance of alcohol). At end of reaction, quenched by addition of reaction mixture to a dilute, cold solution of aqueous potassium hydroxide. This was then diluted with diethyl ether, layers separated, aqueous layer extracted 1× with ether, organics dried over $MgSO_4$, filtered and concentrated. Reaction gave one fluoride product as major product, which is assigned to be the trans product by an invertive $S_N2$ mechanism (note: reaction of the trans alcohol under the same reaction conditions gave a mixture of cis and trans fluoride, likely by a competing $S_N1$ mechanism). Product was further purified by silica gel column chromatography.

$^1H$ NMR (600 MHz, $CDCl_3$) δ 7.85 (m, 2H), 7.73 (m, 2H), 5.07 (dm, 1H), 4.58 (tt, 1H), 2.55 (dtd, 1H), 2.23 (qd, 1H), 2.10 (m, 2H), 1.81 (m, 3H), 1.55 (m, 1H)

$^{13}C$ NMR (151 MHz, $CDCl_3$) δ 168.3, 133.9, 131.9, 123.1, 89.5 (d), 45.3, 33.9 (d), 29.5 (d), 29.1, 19.7

$^{19}F$ NMR (376 MHz, $CDCl_3$) δ −185.4 HRMS (HESI) Exact mass calcd for $C_{14}H_{14}FNO_2Na$ $[M+Na]^+$, 270.0906. Found 270.0896.

Example 5: Exemplary C—H Functionalized Products

General Procedure for Small Molecule C—H Diversification:

Procedure A: To a dried 1-dram screw cap vial with stir bar was added substrate (0.200 mmol) vinylhydroxyamide reagent S4 (172.6 mg, 0.400 mmol), NFSI (0.400 mmol). In glovebox was added trifluorotoluene solvent (0.20 mL), vial capped and sealed with Teflon tape. Reaction heated to 70° C. overnight. At the end of the reaction, mixture was passed through a short pad of silica, concentrated, and crude analyzed by NMR. Products further purified by silica gel column chromatography.

Procedure B: To a dried 1-dram screw cap vial with stir bar was added substrate (0.200 mmol) vinylhydroxyamide reagent S4 (172.6 mg, 0.400 mmol), benzenesulfonyl azide (0.800 mmol). In glovebox was added trifluorotoluene solvent (0.20 mL), vial capped and sealed with Teflon tape. Reaction heated to 70° C. overnight. At the end of the reaction, mixture was passed through a short pad of silica, concentrated, and crude analyzed by NMR. Products further purified by silica gel column chromatography. Note: in some cases reaction yields were observed to be higher when reaction was run in the absence of solvent.

Procedure C: To a dried 1-dram screw cap vial with stir bar was added substrate (0.200 mmol) vinylhydroxyamide reagent S4 (172.6 mg, 0.400 mmol). In glovebox was added trifluorotoluene solvent (0.20 mL), vial capped and sealed with Teflon tape. Radical trap (0.800 mmoL) was added through the septum outside of the glovebox. Reaction heated to 70° C. overnight. At the end of the reaction, mixture was passed through a short pad of silica, concentrated, and crude analyzed by NMR. Products further purified by silica gel column chromatography.

Procedure D: To a dried 1-dram screw cap vial with stir bar was added substrate (0.200 mmol) vinylhydroxyamide reagent S4 (172.6 mg, 0.400 mmol), trap (0.800 mmol). In glovebox was added trifluorotoluene solvent (0.20 mL), vial capped and sealed with Teflon tape. Reaction heated to 70° C. overnight. At the end of the reaction, mixture was passed through a short pad of silica, concentrated, and crude analyzed by NMR. Products further purified by silica gel column chromatography.

Procedure E: To a dried 1-dram screw cap vial with stir bar was added substrate (0.200 mmol) vinylhydroxyamide reagent S4 (172.6 mg, 0.200 mmol), trap (0.400 mmol). In glovebox was added trifluorotoluene solvent (0.20 mL), vial capped and sealed with Teflon tape. Reaction heated to 70° C. overnight. At the end of the reaction, mixture was passed through a short pad of silica, concentrated, and crude analyzed by NMR. Products further purified by silica gel column chromatography.

Procedure F: To a dried 1-dram screw cap vial with stir bar was added substrate (0.200 mmol) vinylhydroxyamide reagent S4 (172.6 mg, 0.200 mmol), trap (0.400 mmol). In glovebox was added trifluorotoluene solvent (0.20 mL), vial capped and sealed with Teflon tape. Reaction heated to 70° C. overnight. At the end of the reaction, mixture was passed through a short pad of silica, concentrated, and crude analyzed by NMR. Products further purified by silica gel column chromatography.

Procedure G: To a dried 1-dram screw cap vial with stir bar was added substrate (0.200 mmol) vinylhydroxyamide reagent S4 (172.6 mg, 0.200 mmol), NFSI (0.400 mmol). In glovebox was added trifluorotoluene solvent (0.20 mL), vial capped and sealed with Teflon tape. Reaction heated to 60° C. overnight. At the end of the reaction, mixture was passed through a short pad of silica, concentrated, and crude analyzed by NMR. Products further purified by silica gel column chromatography.

Procedure H: To a dried 1-dram screw cap vial with stir bar was added substrate (0.200 mmol) vinylhydroxyamide reagent S4 (172.6 mg, 0.200 mmol), NFSI (0.400 mmol). In glovebox was added trifluorotoluene solvent (0.20 mL), vial capped and sealed with Teflon tape. Reaction heated to 60° C. overnight. At the end of the reaction, mixture was passed through a short pad of silica, concentrated, and crude analyzed by NMR. Products further purified by silica gel column chromatography.

Procedure I: To a dried 1-dram screw cap vial with stir bar was added substrate (0.200 mmol) vinylhydroxyamide reagent S4 (172.6 mg, 0.400 mmol). In glovebox was added trifluorotoluene solvent (0.20 mL), vial capped and sealed with Teflon tape. Radical trap (0.800 mL) was added through the septum outside of the glovebox. Reaction heated to 60° C. overnight. At the end of the reaction, mixture was passed through a short pad of silica, concentrated, and crude analyzed by NMR. Products further purified by silica gel column chromatography.

Procedure J: To a dried 1-dram screw cap vial with stir bar was added substrate (0.200 mmol) vinylhydroxyamide reagent S4 (172.6 mg, 0.200 mmol), trap (0.400 mmol). In glovebox was added trifluorotoluene solvent (0.20 mL), vial capped and sealed with Teflon tape. Reaction heated to 60° C. overnight. At the end of the reaction, mixture was passed through a short pad of silica, concentrated, and crude analyzed by NMR. Products further purified by silica gel column chromatography.

Characterization of C—H Diversification Products

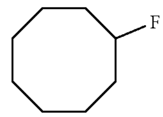

2

Cyclooctyl fluoride (2): Prepared according to General Procedure G on 0.200 mmol scale with NFSI trap giving 77% GC yield. GC data obtained using Method 2, supported by comparison with independently synthesized product.

TABLE 3

| Compound | Ret Time (min) | Percent area (%) |
|---|---|---|
| Fluorocyclooctane | 5.975 | 81.648 |
| Dodecane standard | 15.595 | 18.352 |

3

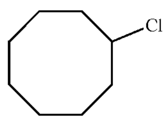

Cyclooctyl chloride (3): Prepared according to General Procedure C on 0.200 mmol scale with CCH trap giving 63% GC yield. GC data obtained using Method 2, supported by comparison with work previously done in our lab.[16]

TABLE 4

| Compound | Ret Time (min) | Percent area (%) |
|---|---|---|
| Chlorocyclooctane | 12.513 | 80.855 |
| Dodecane standard | 15.595 | 19.145 |

4

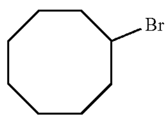

Cyclooctyl bromide (4): Prepared according to General Procedure F on 0.200 mmol scale with $BrCCl_3$ trap giving 62% GC yield. GC data obtained using Method 3, supported by comparison to commercially available product.

TABLE 5

| Compound | Ret Time (min) | Percent area (%) |
|---|---|---|
| Dodecane standard | 12.707 | 22.359 |
| Bromocyclooctane | 13.893 | 77.641 |

5

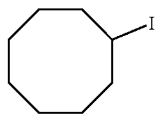

Cyclooctyl iodide (5): Prepared according to General Procedure C on 0.200 mmol scale with perfluorohexyl iodide trap giving 70% yield by $^1H$ NMR. Spectral data is consistent literature values.[56]

6

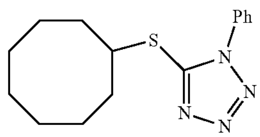

5-(cyclooctylthio)-1-phenyl-1H-tetrazole (6): Prepared via a modified general procedure: to a flame dried 1-dram screw cap vial equipped with a stir bar was reagent 1 (176 mg, 0.400 mmol), and disulfide S21 (283 mg, 0.800 mmol). In glovebox was added cyclooctane (26.9 μL, 0.200 mmol), chlorobenzene solvent (0.20 mL), vial was capped and taped. The reaction was heated to 80° C. and stirred overnight. Prepared according to general procedure K on a 0.200 mmol scale using cyclooctane, vinylhydroxyamide reagent 1 (2 equiv), and disulfane trap S21 (4 equiv), giving 78% NMR yield, in accordance with independently synthesized product. The crude residue was purified using flash column chromatography on silica (1-5% $Et_2O$ in Hexanes) to afford pure 6 as a white solid, isolated with a minor inseparable impurity.

7

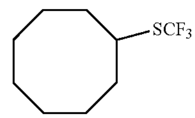

Cyclooctyl(trifluoromethyl) sulfane (7): Prepared via a slightly modified procedure: to a dried 1-dram screw cap vial with stir bar was added substrate (0.200 mmol) vinylhydroxyamide reagent 1 (172.6 mg, 0.200 mmol), $PhSO_2SCF_3$ trap (0.200 mmol). In glovebox was added trifluorotoluene solvent (0.20 mL), vial capped and sealed with Teflon tape. Reaction heated to 70° C. overnight. At the end of the reaction, mixture was purified away from byproducts overlapping in NMR via silica gel chromatography using 2% ethyl acetate in pentanes, analyzed to give 76% yield by $^1H$ NMR. Spectral data is consistent literature values.[57]

8

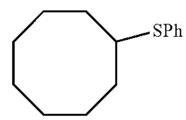

Cyclooctyl phenyl sulfide (8): Prepared according to General Procedure E on 0.200 mmol scale with $PhSO_2SPh$ trap giving 44% GC yield. GC data obtained using Method 4, supported by comparison to independently synthesized product.

TABLE 6

| Compound | Ret Time (min) | Percent area (%) |
|---|---|---|
| Dodecane standard | 5.024 | 15.704 |
| Cyclooctyl Phenyl Thioether | 10.629 | 85.296 |

9

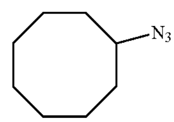

Cyclooctyl azide (9): Prepared according to General Procedure B on 0.200 mmol scale with $PhSO_2N_3$ trap giving 84% yield by $^1H$ NMR. Spectral data is consistent literature values.[58]

10

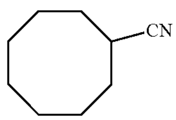

Cyclooctanecarbonitrile (10): Prepared according to General Procedure D on 0.200 mmol scale with p-toluenesulfonyl cyanide trap giving >95% yield by $^{1}$H NMR. Spectral data is consistent literature values.[59]

11a

11b

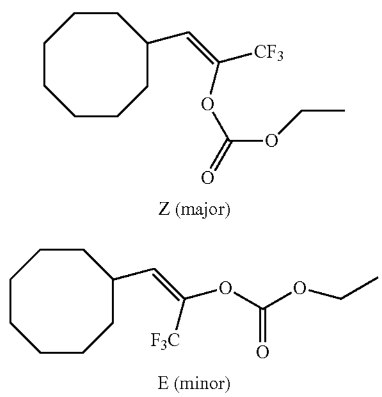

Z (major)

E (minor)

1-cyclooctyl-3,3,3-trifluoroprop-1-en-2-yl ethyl carbonate (11): Prepared according to General Procedure D on 0.200 mmol scale with vinyl trap giving 70% yield by $^{1}$H NMR as 6:1 mixture of E: Z isomers. Isomers assigned based off of previous work done by Zard.[49]

Major (E) Isomer (11a):

$^{1H}$ NMR (600 MHz, $CDCl_3$) δ 5.99 (d, 1H), 4.33 (q, 2H), 2.50 (m, 1H), 1.75-1.45 (m, 14H), 1.39 (t, 3H)

$_{13}$C NMR (151 MHz, $CDCl_3$) δ 152.2, 131.9 (q), 120.0, 119.0, 65.6, 34.3, 30.8, 26.9, 26.1, 24.9, 14.1

$_{19}$F NMR (376 MHz, $CDCl_3$) δ −70.5 Minor (Z) isomer (11b):

$^{1H}$ NMR (600 MHz, $CDCl_3$) δ 4.96 (p, 1H), 4.28 (m, 2H), 2.44 (m, 2H), 2.22 (d, 1H), 2.00 (m, 2H), 1.75-1.45 (m, 9H), 1.36 (t, 3H)

$_{13}$C NMR (151 MHz, $CDCl_3$) δ 154.4, 132.7 (q), 122.7, 117.2, 65.0, 46.4, 40.3, 38.7, 35.0 (d), 31.8 (d), 24.8 (d)

$_{19}$F NMR (376 MHz, $CDCl_3$) δ −73.8

HRMS (HESI) Exact mass calcd for $C_{14}H_{21}F_3O_3Na$ $[M+Na]^+$, 317.1340. Found 317.1329.

12

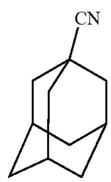

1-adamantanecarbonitrile (12): Prepared according to General Procedure D on 0.200 mmol scale with p-toluenesulfonyl cyanide trap giving 64% yield by $^{1}$H NMR as an average of two experiments. Spectral data is consistent literature values.[59]

13

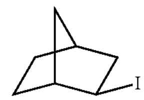

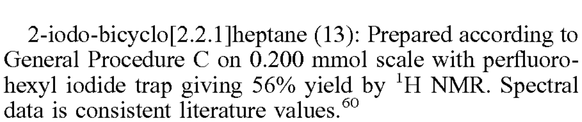

2-iodo-bicyclo[2.2.1]heptane (13): Prepared according to General Procedure C on 0.200 mmol scale with perfluorohexyl iodide trap giving 56% yield by $^{1}$H NMR. Spectral data is consistent literature values.[60]

14

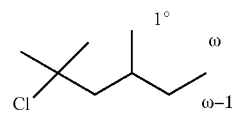

3-methyl-chloro-pentane (14): Prepared according to General Procedure I on 0.200 mmol scale with $CCl_4$ trap giving 64% GC yield. GC data obtained using Method 1, supported by comparison with independently synthesized product.

TABLE 7

| Product | Retention time (min) | Peak Area (%) |
|---|---|---|
| 3° | 3.697 | 6.2 |
| w-1 | 4.123 | 32.8 |
| w-1 (diastereomer) | 4.209 | 31.8 |
| 1° | 4.884 | 3.8 |
| w | 4.987 | 25.5 |

15

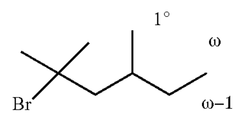

3-methyl-bromo-pentane (15): Prepared according to General Procedure I on 0.200 mmol scale with $BrCCl_3$ trap giving 62% GC yield. GC data obtained using Method 1, supported by comparison with independently synthesized product.

TABLE 8

| Product | Retention time (min) | Relative Area (%) |
|---|---|---|
| 3° | 6.063 | 1.0 |
| w-1 | 6.670 | 31.1 |
| w-1 (diastereomer) | 6.846 | 30.1 |
| 1° | 7.690 | 5.9 |
| w | 7.926 | 31.9 |

16

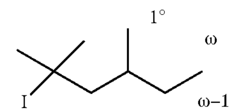

3-methyl-iodo-pentane (16): Prepared according to General Procedure I on 0.200 mmol scale with perfluorohexyl iodide trap giving 54% GC yield. GC data obtained using Method 2, supported by comparison with previously published work and independently synthesized terminal product.

TABLE 9

| Product | Retention time (min) | Relative Area (%) |
|---|---|---|
| 3° | 3.958 | 1.7 |
| ω-1 | 5.046 | 31.5 |
| ω-1 (diastereomer) | 5.185 | 31.4 |
| 1° | 5.674 | 3.7 |
| ω | 5.885 | 31.7 |

17

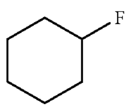

Cyclohexyl fluoride (17): Prepared according to General Procedure A on 0.200 mmol scale with NFSI trap giving 50% GC yield. GC data obtained using Method 1, supported by comparison to commercially available product.

TABLE 10

| Compound | Ret Time (min) | Percent area (%) |
|---|---|---|
| Fluorocyclohexane | 2.83 | 70.484 |
| Dodecane standard | 25.0 | 29.516 |

18

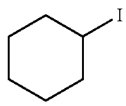

Cyclohexyl iodide (18): Prepared according to General Procedure C on 0.200 mmol scale with perfluorohexyl iodide trap giving 63% GC yield. GC data obtained using Method 3, supported by comparison to commercially available product.

TABLE 11

| Compound | Ret Time (min) | Percent area (%) |
|---|---|---|
| Iodocyclohexane | 7.457 | 72.626 |
| Dodecane standard | 12.707 | 27.374 |

Scheme 30

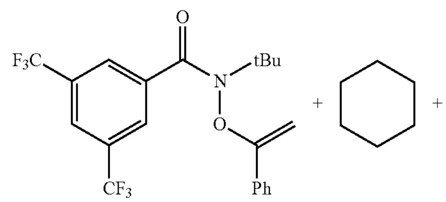

-continued

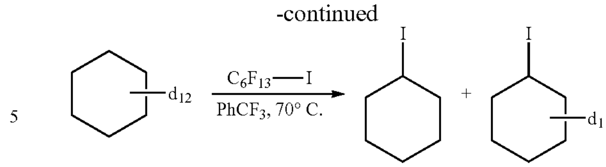

Competition Experiment: To a flame dried 1 dram vial with stir bar was added alkenylhydroxyamide reagent 1 (172 mg, 0.400 mmol). In the glovebox, reagent was dissolved in $PhCF_3$ (0.20 mL), cyclohexane (216 μL, 2.00 mmol), cyclohexane-d12 (216 μL, 2.00 mmol) were added. Mixture was heated to 70° C. for 15 minutes, then was diluted with $CH_2Cl_2$, passed over a short silica plug, and analyzed by GCMS using an Agilent 7820A GC System with an Agilent 5977E MSD to determine the ratio of non-deuterated to deuterated product ($k_H/k_D$=6.4).

19

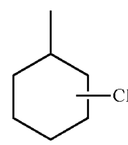

Methylcyclohexyl-chloride (19): Prepared according to General Procedure C on 0.200 mmol scale with CCH trap giving 56% yield of secondary chloride products by NMR. Selectivity data obtained by GC using Method 2, supported by comparison with previously published worked from our laboratory.[16]

TABLE 12

| Peak | Retention Time (min) | Rel % Area |
|---|---|---|
| 3° | 4.009 | 3.2 |
| 3-cis, 2-trans | 4.58 | 46.1 |
| 4-trans | 4.73 | 26.9 |
| 3-trans | 4.82 | 12.2 |
| 4-cis | 5.06 | 10.0 |
| 2-cis | 5.95 | 1.6 |

20

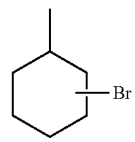

Methylcyclohexyl-bromide (20): Prepared according to General Procedure C on 0.200 mmol scale with $BrCCl_3$ trap giving 76% GC yield. GC data obtained using Method 2, supported by comparison with previously published worked from our laboratory.[15]

TABLE 13

| Peak | Retention Time (min) | Rel % Area |
|---|---|---|
| 3° | 6.185 | 0.8 |
| 3-cis, 4-trans | 7.007 | 45.3 |
| 3-trans | 7.243 | 29.1 |

TABLE 13-continued

| Peak | Retention Time (min) | Rel % Area |
|---|---|---|
| 4-cis | 7.373 | 13.8 |
| 2-cis | 7.766 | 11.0 |

21a

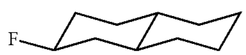

C3α

21b

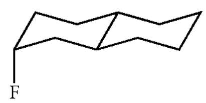

C3β

21c

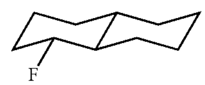

C2α

21d

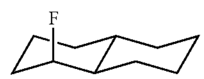

C2β

Fluoro-trans-decalin (21): Prepared according to General Procedure A on 0.200 mmol scale with NFSI trap giving 50% yield by $^{19}F$ NMR (1-bromo-4-fluorobenzene added as internal standard). Regioisomers assigned by comparison to known literature values: 5% C3α 21a ($^{19}F$ NMR: −167.8 ppm), 17% C313 21b (−183.0 ppm), 16% C2α 21c (−177.3 ppm), 12% C213 21d (−196.6). Spectral data is consistent literature values.[61]

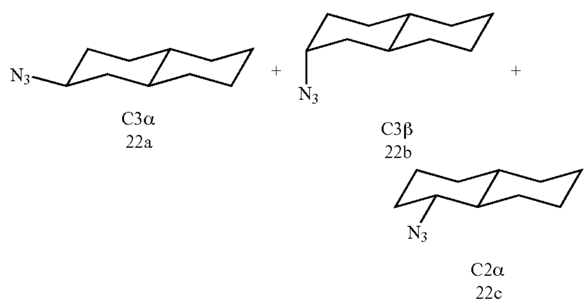

C3α 22a + C3β 22b + C2α 22c

Azido-trans-decalin (22): Prepared according to General Procedure B on 0.200 mmol scale with $PhSO_2N_3$ trap giving 50% yield by $^1H$ NMR (15% C3α 22a by tt at 3.26 ppm, 17% C3β 22b by p at 3.94 ppm, 18% C2α 22c by m at 3.85 ppm). Spectral data is consistent literature values.[62]

23

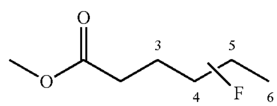

Fluoro-methyl-hexanoate (23): Prepared according to General Procedure A on 0.200 mmol scale with NFSI trap giving 52% yield by $^{19}F$ NMR as an average of two experiments (1-bromo-4-fluorobenzene added as internal standard). Regioisomers assigned by comparison to known literature values: 33% yield 5-fluoro ($^{19}F$ NMR: −173.2 ppm) 13% 4-fluoro (−183.9 ppm), <1% 6-fluoro (−219.0 ppm), 6% 3-fluoro (−179.8 ppm, assigned by analogy to previously observed selectivity). Spectral data is consistent literature values.[63,64]

24

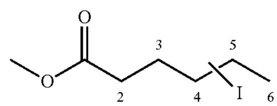

Iodo-methyl-hexanoate (24): Prepared according to General Procedure C on 0.200 mmol scale with perfluorohexyl iodide trap giving 49% GC yield. GC data obtained using Method 3, supported by comparison with previously published work and independently synthesized 5-iodo product.

TABLE 14

| Product | Retention time (min) | Relative Area (%) |
|---|---|---|
| 2 | 13.665 | 6.6 |
| 3 | 14.260 | 13.2 |
| 4 | 15.852 | 15.8 |
| 5 | 16.617 | 52.4 |
| 6 | 19.384 | 11.9 |

25

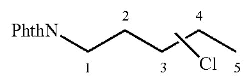

N-pentylphthalimidyl chloride (25): Prepared according to General Procedure C on 0.200 mmol scale with CCH trap giving 66% yield by $^1H$ NMR. GC data used for selectivity, obtained using Method 2, supported by comparison with previously published work.[16]

TABLE 15

| Product | Retention time (min) | Relative Area (%) |
|---|---|---|
| 1 | — | — |
| 2 | — | — |
| 3 | 11.389 | 5.0 |
| 4 | 11.951 | 81.1 |
| 5 | 12.779 | 13.9 |

26

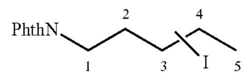

N-pentylphthalimidyl iodide (26): Prepared according to General Procedure C on 0.200 mmol scale with perfluorohexyl iodide trap giving 53% GC yield. GC data obtained using Method 4, supported by comparison with previously published work and independently synthesized 4-iodo product.[15]

TABLE 16

| Product | Retention time (min) | Relative Area (%) |
|---|---|---|
| 1 | — | — |
| 2 | — | — |
| 3 | 13.505 | 7.0 |
| 4 | 14.618 | 79.4 |
| 5 | 17.067 | 13.6 |

27

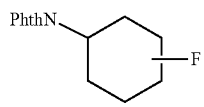

N-cyclohexylphthalimidyl fluoride (27): Prepared according to General Procedure H on 0.200 mmol scale with NFSI trap giving 70% combined yield by $^{19}F$ NMR (1-bromo-4-fluorobenzene added as internal standard). Regioisomers assigned by comparison to literature values and independent synthesis: 4% 4-trans ($^{19}F$ NMR: −172.2 ppm), 12% 4-cis (−185.7 ppm), 40% 3-trans (−185.5 ppm), 14% 3-cis (−169.3 ppm).[65]

28

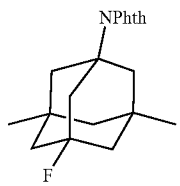

3-fluoro-N-phthalimidyl memantine (28): Prepared according to General Procedure A on 0.200 mmol scale with NFSI trap giving 68% yield by $^1H$ NMR. Purified via silica gel column chromatography using ethyl acetate/hexanes ($R_f$=0.5 in 15% ethyl acetate in hexanes, slightly UV active and stains with $KMnO_4$).

$^{1H}$ NMR (600 MHz, $CDCl_3$) δ 7.79 (m, 2H), 7.71 (m, 2H), 2.61 (d, 2H), 2.14 (dd, 4H), 1.65 (dm, 4H), 1.22 (dm, 2H), 1.03 (s, 6H)

$_{13}C$ NMR (151 MHz, $CDCl_3$) δ 169.4, 133.9, 131.7, 122.7, 49.0, 47.6 (d), 44.9, 43.7, 34.8, 34.7, 29.2

$_{19}F$ NMR (376 MHz, $CDCl_3$) δ −135.70

HRMS (HESI) Exact mass calcd for $C_{20}H_{22}FNO_2Na$ $[M+Na]^+$, 350.1532. Found 350.1521.

29

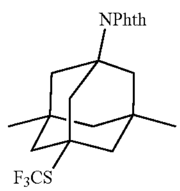

3-trifluoromethlthio-N-phthalimidyl memantine (29): Prepared according to General Procedure D on 0.200 mmol scale with $PhSO_2SCF_3$ trap giving >95% yield by 1H NMR. Purified via silica gel column chromatography using 38:1:1 hexanes: ethyl acetate: DCM ($R_f$=0.2 in solvent mixture).

$_1H$ NMR (600 MHz, $CDCl_3$) δ 7.79 (m, 2H), 7.71 (m, 2H), 2.70 (br s, 2H), 2.20 (dd, 4H), 1.75 (dd, 4H), 1.28 (m, 2H), 1.01 (s, 6H)

$_{13}C$ NMR (151 MHz, $CDCl_3$) δ 169.4, 133.9, 131.7, 122.7, 61.5, 51.3, 48.8, 48.3, 44.7, 44.1, 34.1, 29.6

$_{19}F$ NMR (376 MHz, $CDCl_3$) δ −33.9

HRMS (HESI) Exact mass calcd for $C_{21}H_{22}F_3NO_2SNa$ $[M+Na]^+$, 432,1221. Found 432.1209.

30

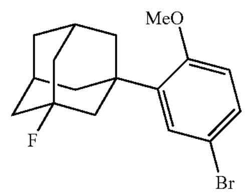

(5S)-1-(5-bromo-2-methoxyphenyl)-3-fluoroadamantane (30): Prepared according to General Procedure A on 0.200 mmol scale with NFSI trap giving 72% yield by $^1H$ NMR. Isolated by silica gel chromatography using 78/1/1 pentanes/DCM/$Et_2O$.

$^{1H}$ NMR (600 MHz, $CDCl_3$) δ 7.32 (dd, 1H), 7.29 (d, 1H), 6.77 (d, 1H), 3.84 (s, 3H), 2.40 (br s, 2H), 2.23 (d, 2H), 2.00 (br s, 4H), 1.95 (br s, 4H), 1.66 (m, 2H)

$_{13}C$ NMR (151 MHz, $CDCl_3$) δ 157.5, 138.1, 129.9, 129.6, 113.3, 113.2, 93.9, 92.7, 55.2, 45.1 (d), 42.1 (d), 41.5 (d), 38.8 (d), 35.2 (d), 31.5 (d)

$_{19}F$ NMR (376 MHz, $CDCl_3$) δ −129.6

HRMS (EI) Exact mass calcd for $C_{17}H_{20}BrFOH$ $[M+H]^+$, 339.0760. Found 338.0711.

31

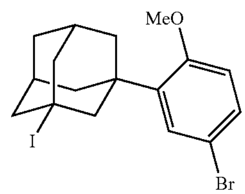

(5S)-1-(5-bromo-2-methoxyphenyl)-3-iodoadamantane (31): Prepared according to General Procedure C on 0.200 mmol scale with perfluorohexyl iodide trap giving >95% yield by $^1H$ NMR. Isolated by silica gel chromatography using 78/1/1 hexanes/DCM/EtOAc.

$^{1H}$ NMR (600 MHz, $CDCl_3$) δ 7.32 (dd, 1H), 7.26 (d, 1H), 6.76 (d, 1H), 3.85 (s, 3H), 2.96 (s, 2H), 2.66 (d, 4H), 2.23 (d, 2H), 2.12 (br s, 2H), 2.05 (d, 2H), 1.83 (br s, 2H)

$_{13}C$ NMR (151 MHz, $CDCl_3$) δ 157.5, 138.0, 129.9, 129.4, 113.3, 113.2, 55.3, 54.2, 51.7, 50.6, 41.9, 38.5, 35.0, 33.1

HRMS (APCI) Exact mass calcd for $C_{17}H_{20}BrIOH$ $[M+H]^+$, 446.9820. Found 446.9808.

32

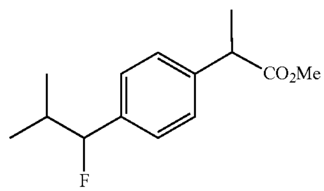

Methyl 2-(4-(1-fluoro-2-methylpropyl)phenyl)propanoate (32): Prepared according to General Procedure H on 0.200 mmol scale with NFSI trap giving 67% yield (>20:1 rr) by $^{1}$H NMR as an average of 2 experiments. Physical and spectral data is consistent literature values.[66]

33

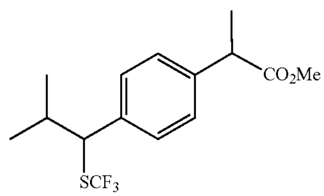

Methyl 2-(4-(1-trifluoromethylthio-2-methylpropyl)phenyl)propanoate (33): Prepared according to General Procedure J on 0.200 mmol scale with $PhSO_2SCF_3$ trap giving 48% yield by $^{1H}$ NMR. Spectral data is consistent literature values.[67]

34

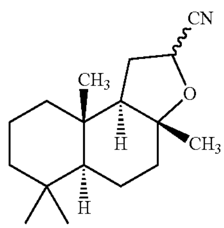

(3aR,9aS,9bR)-3a,6,6,9a-tetramethyldodecahydronaphtho[2,1-b]furan-2-carbonitrile (34): Prepared according to General Procedure D on 0.200 mmol scale with p-toluenesulfonyl cyanide trap giving 84% yield as a 1.3:1 mixture of diastereomers by $^{1}$H NMR. Spectral data is consistent literature values.[59]

35

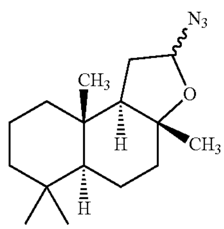

(3aR,9aS,9bR)-2-azido-3a,6,6,9a-tetramethyldodecahydronaphtho[2,1-b]furan (35)

Prepared according to General Procedure B on 0.200 mmol scale with $PhSO_2N_3$ trap giving 56% yield by $^{1}$H NMR (1.5:1 mix of diastereomers). Spectral data is consistent literature values.[58]

36a

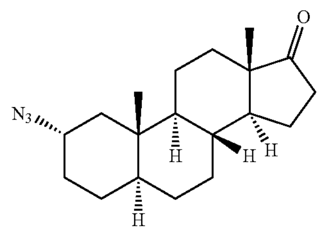

2α = 34%

36b

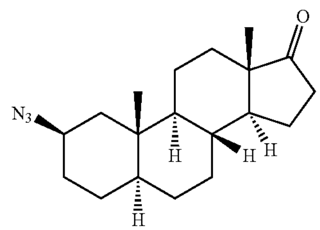

2β = 14%

36c

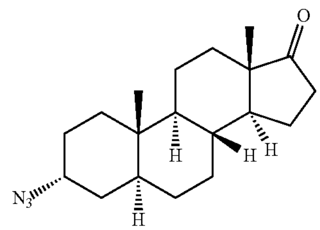

3α = 15%

36d

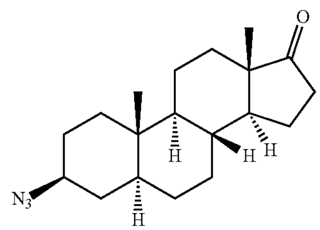

3β = 7%

(2S,5S,8R,9S,10S,13S,14S)-2-azido-10,13-dimethylhexadecahydro-17H-cyclopenta[a]phenanthren-17-one (36a): Prepared according to General Procedure B on 0.200 mmol scale with $PhSO_2N_3$ trap giving 70% combined yield by $^{1}$H NMR. Regioisomers assigned by comparison to known literature values and NMR analysis: 34% 2α 36a ($^{1}$H NMR: 3.14 (dtd)), 14% 213 36b (3.41, m), 15% 3α 36c (3.91, m)[68], 7% 313 36d (3.30, m)[68], Product isolated by silica gel chromatography (10% ethyl acetate in hexanes) as a mixture of regioisomers. Major product peak presents as a doublet of triplet of doublets (J=20.1, 11.4, 4.4 Hz, see below), suggesting it is coupled to 4 protons (2 presenting the same J value and 2 presenting different J values); assuming this does not arise from long range coupling (typified by J values of 1-3 Hz), this eliminates sites of functionalization a to tertiary and quaternary centers and limits possible sites of functionalization to the 2 and 3 positions. As spectrum does not match literature values for azidation products at the 3 position, major product must be at the 2 position, and is assumed to be the 2α product by comparison to Groves' fluorination of deoxyandrosterone (in our hands gave >4 fluorination products, but 2α as major product).[68,69] Major (2α) isomer:

$^1$H NMR (600 MHz, $CDCl_3$) δ 3.14 (dtd, 1H), 2.48 (dd, 1H), 2.20-0.90 (m, 21H), 0.86 (s, 3H), 0.84 (s, 3H)

$^{13}$C NMR (151 MHz, $CDCl_3$) δ 221.1, 61.8, 54.5, 51.3, 47.8, 46.0, 37.5, 35.8, 34.7, 32.1, 31.5, 30.7, 30.3, 27.5, 23.6, 21.7, 20.4, 13.8, 13.1

HRMS (HESI) Exact mass calcd for $C_{19}H_{29}N_3OH$ $[M+H]^+$, 316.2389. Found 316.2380

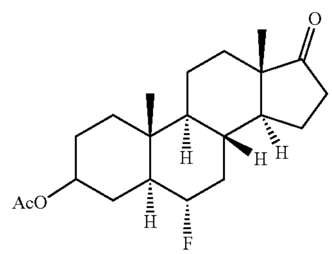

6α (34%)

37a

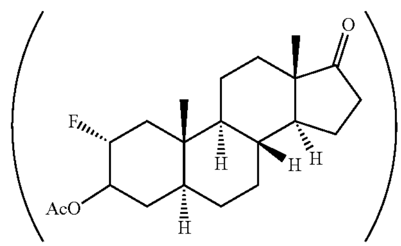

2α (13%)

37b (3S,5S,6S,8R,9S,10R,13S,14S)-6-fluoro-10,13-dimethyl-17-oxohexadecahydro-1H-cyclopenta[a]phenanthren-3-yl acetate (37a): Prepared according to General Procedure H on 0.200 mmol scale with NFSI trap giving 47% combined yield by $^{19}$F NMR (1-bromo-4-fluorobenzene added as internal standard). Assignment of the major product (6α, 37a, $^{19}$F NMR: −180.6 ppm) was assigned in comparison to previous selectivity observed in our laboratory, along with comparison to literature values to previous characterization of said product.[17,24] Minor product assigned by comparison to previous selectivity observed in our lab (2α, 37b, −193.1 ppm). Physical and spectral data is consistent literature values.[24]

38

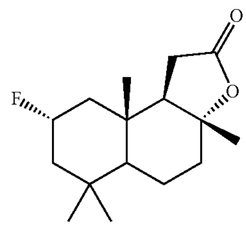

(3aR,8S,9aS,9bR)-8-fluoro-3a,6,6,9a-tetramethyldecahydronaphtho[2,1-b]furan-2 (1H)-one (38): Prepared according to General Procedure A on 0.200 mmol scale with NFSI trap giving 74% yield by $^1$H NMR. Spectral data is consistent literature values.[63]

39

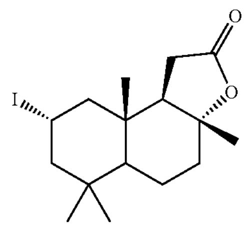

(3aR,8S,9aS,9bR)-8-iodo-3a,6,6,9a-tetramethyldecahydronaphtho[2,1-b]furan-2 (1H)-one (39): Prepared according to General Procedure C on 0.200 mmol scale with perfluorohexyl iodide trap giving >95% yield by $^1$H NMR as an average of two experiments. Purified via silica gel column chromatography using 5% EtOAc in hexanes (Rf=0.3 in 15% EtOAc/hexanes, stains with CAM).

1H NMR (600 MHz, $CDCl_{(3)}$ 6 4.58 (tt, 1H), 2.43 (dd, 1H), 2.28 (m, 2H), 2.20 (dm, 1H), 2.12 (dt, 1H), 2.03 (dd, 1H), 1.92 (m, 2H), 1.74 (m, 2H), 1.33 (m, 4H), 1.20 (dd, 1H), 0.98 (s, 3H), 0.95 (s, 3H), 0.91 (s, 3H)

$_{13}$C NMR (151 MHz, $CDCl_3$) 6 176.01, 85.7, 58.3, 55.6, 55.5, 52.9, 39.6, 38.4, 37.5, 32.6, 28.5, 22.8, 21.6, 21.0, 20.4, 15.3

HRMS (HESI) Exact mass calcd for $C_{16}H_{25}IO_2Na$ $[M+Na]^+$, 399.0797. Found 399.0786.

40

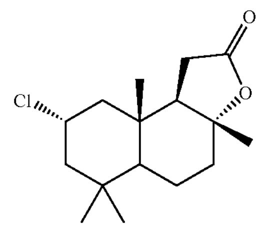

(3aR,8S,9aS,9bR)-8-chloro-3a,6,6,9a-tetramethyldecahydronaphtho[2,1-b]furan-2 (1H)-one (40): Prepared according to General Procedure C on 0.200 mmol scale with $CCl_4$ trap giving 71% yield by $^1$H NMR. The same conditions but initiating using blue LED conditions (2× Kessil H150 440 nm) and fan cooling showed >95% yield by $^1$H NMR. Spectral data is consistent literature values.[16]

41

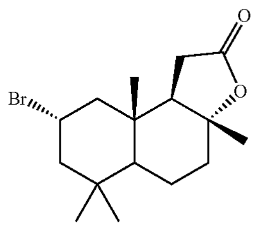

(3aR,8S,9aS,9bR)-8-bromo-3a,6,6,9a-tetramethyldecahydronaphtho[2,1-b]furan-2 (1H)-one (41): Prepared according to General Procedure C on 0.200 mmol scale with $BrCCl_3$ trap giving 90% yield by $^1$H NMR. Spectral data is consistent literature values.[15]

42

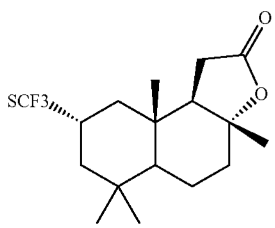

(3aR,8S,9aS,9bR)-8-trifluoromethylthio-3a,6,6,9a-tetramethyldecahydronaphtho[2,1-b]furan-2 (1H)-one (42): Prepared according to General Procedure D on 0.200 mmol scale with $PhSO_2SCF_3$ trap giving 85% yield by 1H NMR. Spectral data is consistent literature values.[17]

43

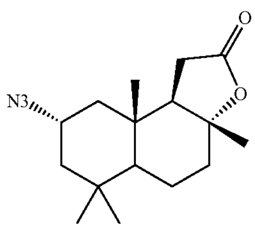

(3aR,8S,9aS,9bR)-8-azido-3a,6,6,9a-tetramethyldecahydronaphtho[2,1-b]furan-2 (1H)-one (43): Prepared according to General Procedure D on 0.200 mmol scale with $PhSO_2N_3$ trap giving 76% yield by $^1$H NMR. Spectral data is consistent literature values. 17

44

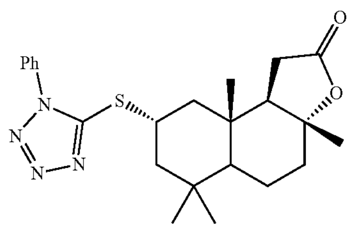

(3aR,8S,9aS,9bR)-3a,6,6,9a-tetramethyl-8-((1-phenyl-1H-tetrazol-5-yl)thio)decahydronaphtho[2,1-b]furan-2 (1H)-one (44): Prepared via a modified general procedure: to a flame dried 1-dram screw cap vial equipped with a stir bar was added sclareolide (251 mg, 1.00 mmol), reagent 1 (863 mg, 2.00 mmol), and disulfide S21 (1.42 g, 4.00 mmol). In glovebox was added chlorobenzene solvent (1.00 mL), vial was capped and taped. The reaction was heated to 80° C. and stirred overnight. Crude product was analyzed by $^1$H NMR giving a 74% yield. The products were further purified by silica gel column chromatography. The crude residue was purified using flash column chromatography on silica (3 DCM: 3 Hexanes: 0.75 $Et_2O$) to afford pure 45 as a white-yellow solid (285 mg, 67% yield).

$^{1H}$ NMR (600 MHz, $CDCl_3$) δ 7.56 (m, 5H), 4.33, (tt, J=12.8, 7.4 Hz, 1H), 2.46 (dd, J=15.5 Hz, 1H), 2.21 (dd, J=22.4, 6.7 Hz, 1H), 2.05 (m, 3H), 1.99 (dd, J=22.0, 7.4 Hz, 1H), 1.92 (m, 1H), 1.70 (td, 14.8, 4.2 Hz, 1H), 1.41 (m, 2H), 1.37 (s, 3H), 1.26 (m, J=12.4 Hz 2H), 1.14 (dd, 15.3, 3.5H 1H), 1.10 (s, 3H), 1.01 (s, 3H), 0.98 (s, 3H)

$_{13}$C NMR (151 MHz, $CDCl_3$) δ 176.13, 153.60, 133.66, 130.17, 129.80, 124.44, 123.92, 85.93, 58.73, 56.15, 48.19, 46.13, 40.83, 38.47, 37.81, 35.36, 32.88, 28.70, 21.65, 21.21, 20.29, 15.56

HRMS (APCI) Exact mass calcd for $C_{23}H_{30}N_4O_2S$ $[M+H]^+$ 427.2168. Found, 427.2159

Scheme 31

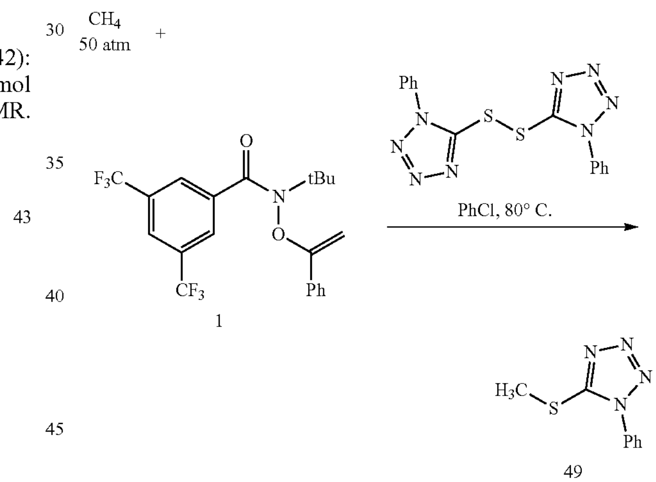

1

49

5-(methylthio)-1-phenyl-1H-tetrazole (48): To a parr bomb under argon atmosphere, vinylhydroxyamide reagent 1 (433 mg, 0.500 mmol) and disulfide S21 (708 mg, 1.00 mmol) were dissolved in PhCl (0.5 ml). The bomb was sealed prior to removal from the glovebox. The bomb was purged with methane twice carefully so as to not expose to air prior to pressurizing at 50 atm. The reaction was heated to 80° C. and stirred overnight. Upon completion of the reaction, the bomb was allowed to cool to room temperature. The reaction mixture was filtered and concentrated under reduced pressure, giving the product in a 20% yield ($^1$H NMR, 82.83, s, 3H).[70]

$^1$H NMR (600 MHz, $CDCl_3$) δ 7.57 (m, 5H), 2.85 (s, 3H)

$^{13}$C NMR (151 MHz, $CDCl_3$) δ 154.8, 133.6, 130.0, 129.7, 123.6, 15.3

Example 6: Further Derivitization of Functionalized Products

Scheme 32

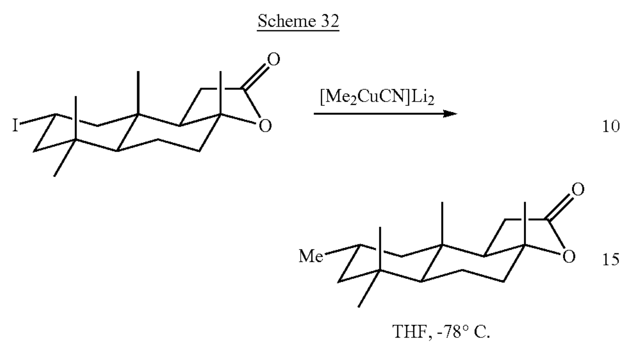

(3aR,9aS,9bR)-3a,6,6,8,9a-pentamethyldecahydronaphtho[2,1-b]furan-2 (1H)-one (45): Adapted from literature procedure.[71] To a flame dried round bottom flask under argon atmosphere, CuCN (179 mg, 1 equiv, 2.00 mmol) was dissolved in THF (10.0 ml). The flask was capped and sealed with Teflon tape prior to removal from the glovebox. This solution was cooled to −78° C. and methyllithium (2.50 ml, 1.6 M in $Et_2O$, 4.00 mmol) was added dropwise. This solution was stirred for 3 hours until was homogenous, tan color. To a separate flame dried vial in the glovebox was added iodosclareolide 39 (37.6 mg, 0.100 mmol) and THF (0.125 ml), vial capped and taped. Vial was cooled to −78° C. and 1.00 ml of the $[Me_2CuCN]Li_2$ solution was added dropwise. The reaction was stirred for 3 h before slowly warming to room temperature. The reaction was quenched with saturated aqueous $NH_4Cl$ before the addition of 25% aqueous $NH_3$, water, and diethyl ether. This solution was stirred for 30 min the organic layer was separated. The aqueous layer was diluted with brine and extracted twice with diethyl ether. The combined organic layers were dried over $MgSO_4$ and concentrated to afford the crude product. The crude residue was purified via silica gel chromatography (10% EtOAc in Hexanes) affording product as a white solid (22.5 mg, 0.086 mmol, 86% isolated (66% isolated overall from sclareolide)).

$^{1H}$ NMR (600 MHz, $CDCl_3$) δ 2.41 (dd, J=15.3 Hz, 1H), 2.25 (dd, J=22.4, 6.6 Hz 1H), 2.08 (dt, J=12.6, 6.6 Hz, 1H), 1.95 (dd, J=21.3, 5.9, 1H), 1.88 (m, 1H), 1.81 (tdt, 1H), 1.69 (m, J=29.9 Hz, 1H), 1.41 (s, 3H), 1.33 (d, 3H), 1.25 (bs, 1H), 0.99 (dd, J=15.5, 2.7 Hz 1H), 0.92 (s, 3H), 0.89 (s, 3H), 0.87 (d, 6.1 Hz, 3H), 0.84 (s, 3H), 0.69 (m, 1H)

$_{13}C$ NMR (151 MHz, $CDCl_3$) 176.90, 86.43, 59.13, 51.44, 48.43, 38.69, 36.71, 33.75, 33.22, 29.72, 28.74, 23.75, 22.57, 21.63, 21.52, 20.47, 15.88

HRMS (HESI) Exact mass calculated for $C_{17}H_{29}O_2$ $[M+H]^+$ 265.2089. Found 265.2161.

Scheme 33

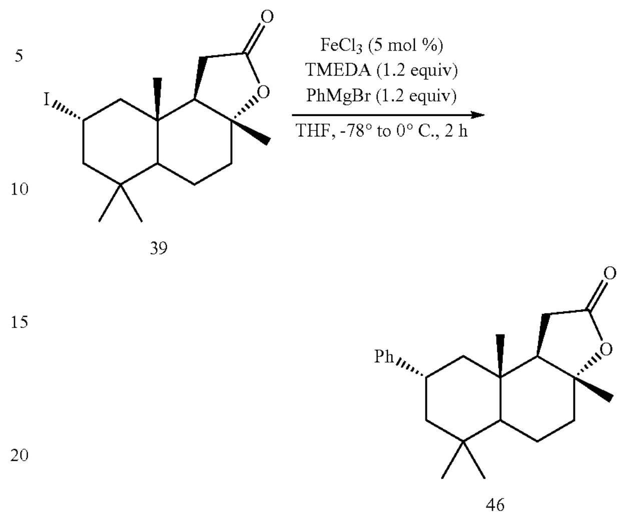

39

46

(3aR,8S,9aS,9bR)-3a,6,6,9a-tetramethyl-8-phenyldecahydronaphtho[2,1-b]furan-2 (1H)-one (46): Adapted from literature procedure.[72] To a flame-dried round bottom flask with a stir bar was added iodosclareolide (94.1 mg, 0.250 mmol), FeCl3 (2.0 mg, 0.0125 mmol), THF (0.125 mL). Mixture was cooled to −78° C. To this solution was added a mixture of tetramethylethylenediamine (TMEDA) (45.0 μL, 0.300 mmol) and phenylmagnesium bromide (1.0 M, 300 μL, 0.300 mmol) dropwise over 10 minutes. Resulting solution was immersed in an ice bath and let stir at 0° C. for 3 hours. At the end of the reaction, mixture was quenched with saturated aqueous $NH_4Cl$, layers separated, aqueous extracted 2× with ether (25 mL), combined organics were dried over $MgSO_4$, filtered, and concentrated. Product was further purified by silica gel column chromatography (10% EtOAc in hexanes) to obtain product as a white solid (47 mg, 58% yield (57% overall from sclareolide). Coupling constants of benzylic hydrogen peak of 12.7 and 3.5 Hz suggest a diaxial hydrogen relationship and allow us to assign the phenyl group as equatorial.

$^{1H}$ NMR (600 MHz, $CDCl_3$) 6 7.33 (t, 2H), 7.23 (m, 3H), 3.00 (tt, 1H), 2.44 (dd, 1H), 2.25 (dd, 1H), 2.15 (dt, 1H), 2.07 (dd, 1H), 1.98 (dm, 1H), 1.69 (td, 1H), 1.66 (ddm, 2H), 1.45 (t, 2H), 1.39 (s, 3H), 1.29 (m, 1H), 1.21 (m, 1H), 3.02 (s, 3H), 0.99 (s, 3H), 0.99 (s, 3H)

$_{13}C$ NMR (151 MHz, $CDCl_3$) 6 176.6, 146.2, 128.5, 127.0, 126.2, 86.2, 59.1, 56.4, 49.9, 47.2, 38.7, 36.9, 35.5, 34.1, 33.1, 28.7, 21.7, 21.3, 20.5, 15.8

HRMS (HESI) Exact mass calcd for $C_{22}H_{30}O_2H$ $[M+H]^+$, 327.2324. Found 327.2315.

Scheme 34

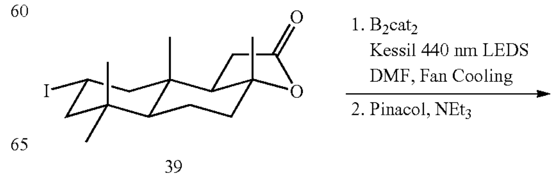

39

-continued

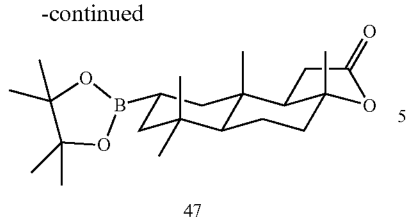

47

(3aR,9aS,9bR)-3a,6,6,9a-tetramethyl-8-(4,4,5,5-tetramethyl-1,3,2-dioxaborolan-2-yl) decahydronaphtho[2,1-b]furan-2 (1H)-one (47): Prepared according to a literature procedure.[35] To a flame dried vial was added iodosclareolide 39 (37.6 mg, 0.100 mmol). Vial brought into the glovebox, and $B_2cat_2$ (95.1 mg, 4.0 equiv, 0.400 mmol) was added. Mixture was then dissolved in DMF (0.30 mL), capped, and taped. The reaction mixture was irradiated from the side with a Kessil 440 nm BLED positioned 2 cm away from the vial under fan cooling for 24 h. Upon completion of the reaction, a mixture of $NEt_3$ (0.25 g, 0.350 ml, 25 equiv, 2.5 mmol) and pinacol (47.3 mg, 4.0 equiv, 0.400 mmol) was added. The mixture was stirred for 1 h at room temperature. The reaction solution was poured into water and extracted with EtOAc (3×20 mL). The combined organic layers were washed with brine, dried over $MgSO_4$, and concentrated en vacuo to afford the crude product. The crude residue was purified via flash column chromatography on silica (2-5% EtOAc in Hexanes) as a white solid (25.2 mg, 67% isolated yield (66% overall from sclareolide)).

$^{1H}$ NMR (600 MHz, $CDCl_3$) 6 2.38 (dd, J=15.8 Hz, 1H), 2.28 (dd, J=22.4, 5.7 Hz, 1H), 2.06 (dt, J=12.9, 6.8 Hz, 1H), 1.95 (dd, J=21.3, 6.6 Hz, 1H), 1.87 (m, 1H), 1.67 (td, J=29.8, 4.6 Hz, 1H), 1.47 (ddd, 1H), 1.43-1.33 (m, 3H), 1.32 (s, 3H), 1.25 (m, 1H), 1.23 (s, 12H), 1.18 (t, J=27.4, 13.7 Hz, 1H), 1.04 (m, 2H), 0.90 (s, 3H), 0.88 (s, 3H), 0.82 (s, 3H)

$_{13}$C NMR (151 MHz, $CDCl_3$) δ 177.06, 86.53, 83.22, 59.13, 56.55, 43.38, 40.74, 38.86, 36.20, 33.26, 33.09, 28.88, 24.88, 21.72, 20.99, 20.68, 15.26

HRMS (HESI) Exact Mass calculated for $C_{22}H_{38}O_4B$ $[M+H]^+$ 377.2785. Found, 377.2853.

Scheme 35

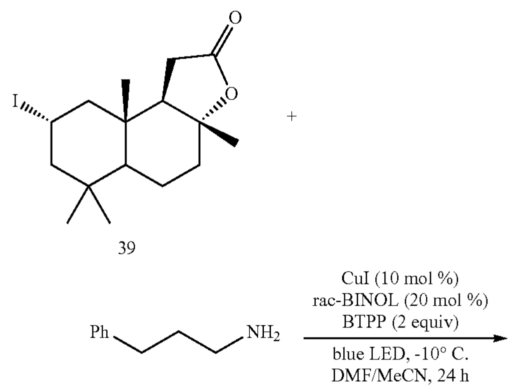

39

-continued

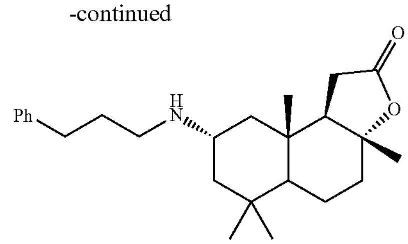

48

(3aR,8S,9aS,9bR)-3a,6,6,9a-tetramethyl-8-((3-phenylpropyl)amino) decahydronaphtho[2,1-b]furan-2 (1H)-one (48): Prepared according to an adapted literature procedure.[36] To a flame dried vial with a stir bar was added copper iodide (3.8 mg, 0.020 mmol), rac-BINOL (11.4 mg, 0.0400 mmol). In glovebox was added DMF (0.20 mL), acetonitrile (0.80 mL), tert-butylimino-tri (pyrrolidino)phosphorane (BTPP) (122 μL, 0.400 mmol). Mixture stirred in glovebox 5 minutes. Then, 3-phenyl-1-propylamine (28.4 μL, 0.200 mmol), iodo-sclareolide (75.3 mg, 0.200 mmol) were added. Vial was capped and taped, and thoroughly sealed with parafilm. Vial was immersed in a cryobath (isopropanol used as solvent) at −10° C., irradiated with 3 Kessil H150 440 nm blue LED lamps for 24 hours (see picture below). At end of reaction, mixture was concentrated in vacuo to remove acetonitrile. Resulting residue was taken up in dichloromethane and washed with 30 mL of an aqueous 5% lithium chloride solution. Layers were separated and aqueous was extracted twice more with dichloromethane. Combined organic layers were dried over $MgSO_4$, filtered, and concentrated. $^1H$ NMR analysis showed a 61% yield with reference to HMDS internal standard over an average of two experiments (59% yield overall from sclareolide).

Resultant residue was further purified by silica gel chromatography with a solvent system of 20% EtOAc/20% MeOH in hexanes, doped with triethylamine, to afford the product 47 as a yellow oil (32 mg, 42% isolated yield).

$^{1H}$ NMR (600 MHz, $CDCl_3$) 6 7.31 (t, 2H), 7.22 (m, 3H), 2.85 (m, 1H), 2.69 (m, 4H), 2.44 (m, 1H), 2.27 (dd, 1H), 2.11 (dm, 1H), 1.98 (dd, 1H), 1.92 (dm, 1H), 1.86 (m, 2H), 1.77 (dm, 1H), 1.73 (m, 2H), 1.40 (m, 1H), 1.35 (s, 3H), 1.09 (dm, 1H), 1.02 (m, 1H), 0.96 (s, 3H), 0.95 (s, 3H), 0.84 (m, 1H)

$_{13}$C NMR (151 MHz, $CDCl_3$) 6 176.5, 141.8, 128.4, 128.3, 125.9, 86.1, 59.0, 56.5, 49.4, 46.4, 38.5, 36.8, 34.1, 33.6, 33.2, 31.8, 29.7, 28.7, 21.7, 21.6, 20.3, 16.1

HRMS (HESI) Exact Mass calculated for C25H37NO2H [M+X]+ 384.2903. Found, 384.2892.

Scheme 36

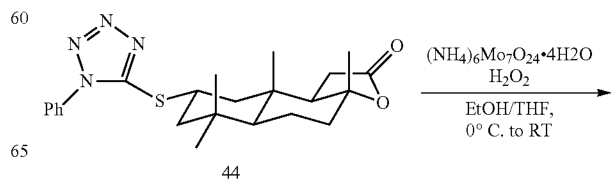

44

-continued

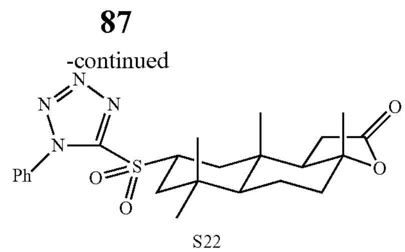

S22

(3aR,9aS,9bR)-3a,6,6,9a-tetramethyl-8-((1-phenyl-1H-tetrazol-5-yl) sulfonyl) decahydronaphtho[2,1-b]furan-2(1H)-one (S22): Prepared according to a literature procedure.[73] To a one-dram vial equipped with a stir bar was added sulfide 44 (85.2 mg, 0.200 mmol) and $(NH_4)_6Mo_7O_{24}\cdot 4H_2O$ (24.7 mg, 0.10 equiv). EtOH/THF (1:1, 1.00 ml) was added and the solution was cooled to 0° C. 30% aq. $H_2O_2$ (82.0 μl, 0.800 mmol, 4.0 equiv) was added and the reaction was allowed to warm to room temperature. The reaction was allowed to run overnight. Upon completion as monitored by TLC analysis, the solution was cooled to 0° C. and quenched with 10% aq. $Na_2S_2O_3$. The solution was diluted with brine and washed with DCM (3×1.00 ml). The combined organic layers were dried over $MgSO_4$, filtered through a short silica plug, and concentrated en vacuo. The product was purified via flash column chromatography on silica (3:3:0.75 DCM/hexanes/diethyl ether) (64.2 mg, 70% yield).

$^{1H}$ NMR (600 MHz, $CDCl_3$) δ 7.64 (m, 5H), 4.23 (tt, J=26.3 Hz, 1H), 2.45 (dd, J=15.9 Hz, 1H), 2.24 (dd, J=25.2, 8.5 Hz, 1H), 2.12, dt, J=12.6 Hz, 1H), 2.02 (m, 3H), 1.94 (dq, 1H), 1.72, (td, J=15.3, 5.8 Hz, 1H), 1.57 (t, J=24.7, 12.6 Hz, 1H), 1.45-1.41 (m, 2H), 1.35 (s, 3H), 1.27 (m, 1H), 1.19 (m, 1H), 1.04 (s, 3H), 1.03 (s, 3H), 0.97 (s, 3H)

$^{13}C$ NMR (151 MHz, $CDCl_3$) 175.71, 152.82, 133.16, 131.71, 129.86, 125.36, 85.71, 58.62, 58.52, 56.15, 39.01, 38.43, 37.25, 36.93, 34.50, 32.85, 32.88, 28.71, 21.79, 21.30, 20.37, 15.81, 14.2

HRMS (APCI) Exact mass cacld for $C_{23}H_{31}O_4N_4S$ $[M+H]^+$ 459.2066. Found, 459.2056

Example 7: General Procedure for Functionalization of Olefins

General Polymer Procedure (130° C.): The polyolefin (40 mg) was pre-dissolved in 0.2 mL of chlorobenzene by heating the solution for 30 min at 130° C. with magnetic stirring. The pre-dissolved polyolefin, amide reagent 1, and radical trap were then combined in a 1-dram reaction vial and diluted with 0.5 mL of chlorobenzene in a nitrogen-filled glovebox. The vial was equipped with a magnetic stir bar under inert atmosphere and sealed with electrical tape. The reaction was heated and stirred on a magnetic stir plate at the desired temperature. After completion of the reaction, the solution was precipitated into acetone and collected via Büchner filtration with nylon filter paper to yield the functionalized commodity polyolefins.

Characterization of Polymer Functionalization Products

Scheme 37

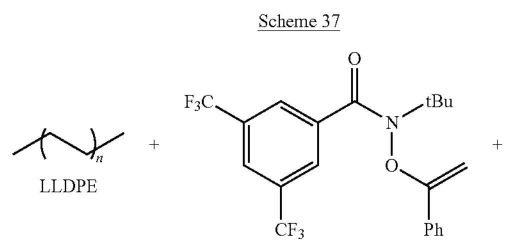

-continued

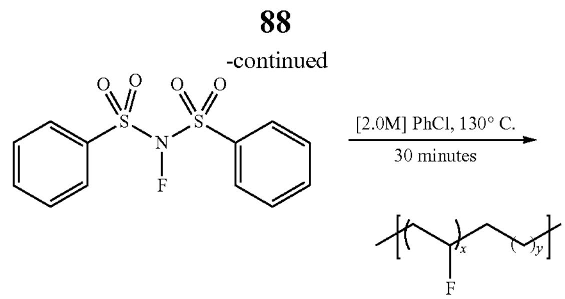

Fluorinated LLDPE (P1): DOW™ DNDA-1081 NT 7 Linear Low Density Polyethylene Resin, (1-phenylvinyloxy)amide, and N-fluorobenzenesulfonimide were reacted according to General Procedure I. LLDPE (RI=19 kg/mol, RI Đ=4.76, MALS dn/dc=0.105, =1.58×10$^4$ g/mol±3.74%, MALS Đ=2.97±3.77%, 19% branched, 40 mg, 0.143 mmol) reacted with (1-phenylvinyloxy)amide (62 mg, 0.14 mmol) and N-fluorobenzenesulfonimide (90 mg, 0.28 mmol) in chlorobenzene (0.7 mL) upon heating at 130° C. for 30 min. The resultant material (26 mg) was 5 mol % fluorinated LLDPE. Collection of the filtrate revealed 85% conversion of the amide reagent by $^{19}F$ NMR. The following was gathered using 5 mol % fluorinated LLDPE:

$^{1H}$ NMR (500 MHz, $C_2D_2Cl_4$, 110° C.) δ 4.60 (bs), 4.50 (bs), 1.73 (bs), 1.56 (bs), 1.41 (bs), 1.02 (bs). $^{19}F$ NMR (400 MHz, $C_2D_2Cl_4$, 80° C.) δ −179.53 (bs). IR (neat, ATR, $cm^{-1}$) 2917, 2850, 1472, 1374, 1279, 1169, 1140, 1087, 1069, 1000, 864, 750, 719. GPC (TCB, 140° C.): RI=17 kg/mol, RI Đ=4.76; MALS dn/dc=0.105, =2.96×10$^4$ g/mol±3.38%, MALS Đ=3.58±3.42%. TGA (° C.) parent Td=428, product Td=294. DSC (° C.): parent=125 with 41% crystallinity (DH=122 J/g), product=112 with 30% crystallinity (DH=86 J/g).

Determination of percent fluorination of LLDPE: Upon purification, the percent fluorination of LLDPE can be determined through integration of the $^1H$ NMR. Considering the composition of the polymer, the peaks between 0.8-2.0 ppm were set to total to 4 protons. The protons alpha the incorporated fluorine group that appear between 4.4-4.6 ppm are used to determine mol % fluorination per repeat unit. Only secondary C—H fluorination was observed.

Scheme 38

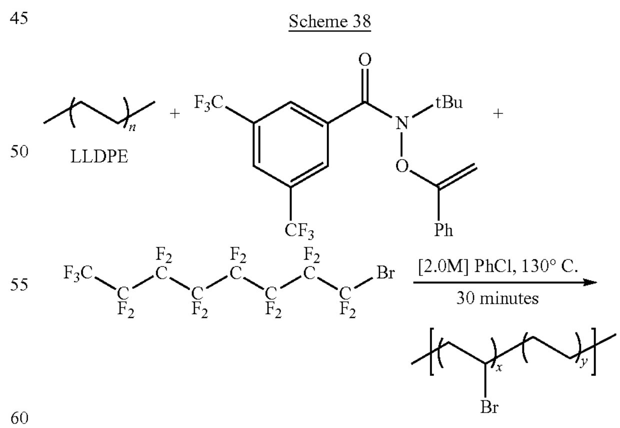

Brominated LLDPE (P2): DOW™ DNDA-1081 NT 7 Linear Low Density Polyethylene Resin, (1-phenylvinyloxy)amide, and 1-bromoheptadecafluorooctane were reacted according to General Procedure I. LLDPE (=19 kg/mol, Đ=4.76, 19% branched, 40 mg, 1.4 mmol) reacted with (1-phenylvinyloxy)amide (62 mg, 0.14 mmol) and 1-bromoheptadecafluorooctane (74$_{jt}$L, 0.29 mmol) in chlorobenzene (0.4 mL) upon heating at 130° C. for 30 min. The resultant material (30 mg) was 4 mol % brominated LLDPE. Collection of the filtrate revealed 77% conversion of the amide reagent by $^{19}F$ NMR.

The following was gathered using 4 mol % brominated LLDPE:

$^{1H}$ NMR (500 MHz, $C_2D_2Cl_4$, 110° C.) δ 4.11 (bs), 1.89 (bs), 1.61 (bs), 1.46 (bs), 1.35 (bs), 0.96 (bs). IR (neat, ATR, $cm^{-1}$): 2916, 2849, 1464, 1463, 1242, 1240, 1142, 813, 722, 719. GPC (TCB, 140° C.)=20 kg/mol, Đ=4.58. TGA (° C.) parent Td=428, product Td=270. DSC (° C.): parent=125 with 41% crystallinity (DH=122 J/g), product=119 with 18% crystallinity (DH=53.2 J/g).

Determination of percent bromination of LLDPE: Upon purification, the percent bromination of LLDPE can be determined through integration of the $^1H$ NMR. Considering the composition of the polymer, the peaks between 0.8-2.0 ppm were set to total to 4 protons. The protons alpha the incorporated bromine group that appear at 4.1 ppm are used to determine mol % bromination per repeat unit. Only secondary C—H bromination was observed.

Scheme 39

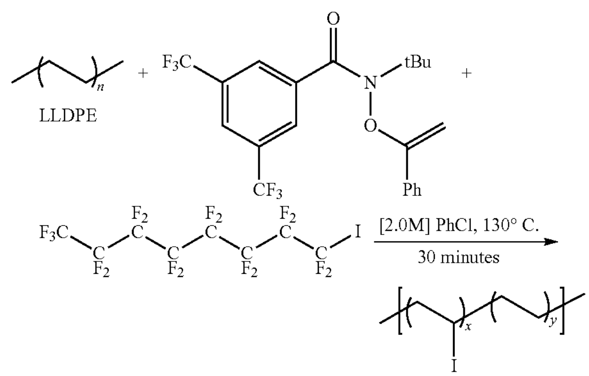

Iodinated LLDPE (P3): DOW™ DNDA-1081 NT 7 Linear Low Density Polyethylene Resin, (1-phenylvinyloxy) amide, and 1-iodoperfluorooctane were reacted according to General Polymer Procedure. LLDPE (=19 kg/mol, Đ=4.76, 19% branched, 40 mg, 1.43 mmol) reacted with (1-phenylvinyloxy)amide (62 mg, 0.14 mmol) and 1-iodoperfluorooctane (81 μL, 0.29 mmol) in chlorobenzene (0.7 mL) upon heating at 130° C. for 30 min. The resultant material (39 mg) was 4 mol % iodinated LLDPE. Collection of the filtrate revealed 79% conversion of the functionalized amide to the parent amide by $^{19}F$ NMR.

The following was gathered using 4 mol % iodinated LLDPE:

$^1H$ NMR (500 MHz, C2D2$Cl_4$, 110° C.) δ 4.21 (bs), 1.95 (bs), 1.79 (bs), 1.57 (bs), 1.44 (bs), 1.36 (bs), 0.98 (bs). IR (neat, ATR, $cm^{-1}$) 2916, 2848, 1644, 1549, 1463, 1367, 1241, 1219, 1178, 1154, 1146, 907, 720. GPC (TCB, 140° C.): =22 kg/mol, Đ=4.19. TGA (° C.) parent Td=428, product Td=225 (Td1=194, Td2=318). DSC (° C.): parent=125 with 41% crystallinity (DH=122 J/g), product=95 with 21% crystallinity (DH=63 J/g).

Determination of percent iodination of LLDPE: Upon purification, the percent iodination of LLDPE can be determined through integration of the 1H NMR. Considering the composition of the polymer, the peaks between 0.8-2.0 ppm were set to total to 4 protons. The protons alpha the incorporated iodo group that appear between 4.15-4.3 ppm are used to determine mol % iodination per repeat unit. Only secondary C—H iodination was observed.

Scheme 40

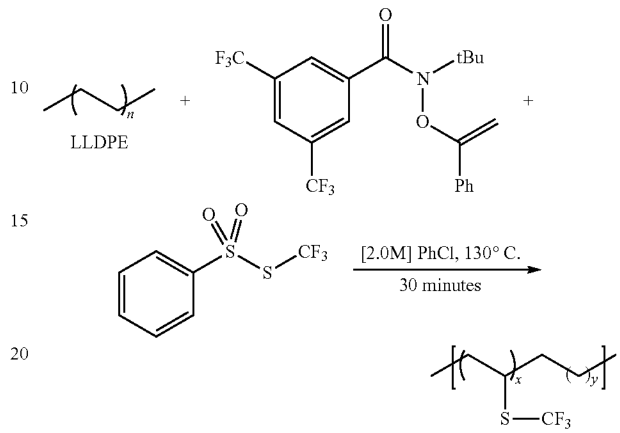

Trifluoromethylthiolated LLDPE (P4): DOW™ DNDA-1081 NT 7 Linear Low Density Polyethylene Resin, (1-phenylvinyloxy)amide, and S-(trifluoromethyl)benzenesulfonothioate were reacted according to General Polymer Procedure. LLDPE (=19 kg/mol, Đ=4.76, 19% branched, 15 mg, 0.54 mmol) reacted with (1-phenylvinyloxy)amide (23 mg, 0.05 mmol) and S-(trifluoromethyl)benzenesulfonothioate (26 mg, 0.11 mmol) in chlorobenzene (0.4 mL) upon heating at 130° C. for 30 min. The resultant material (10 mg) was 3 mol % trifluoromethylthiolated LLDPE. Collection of the filtrate revealed 91% conversion of the functionalized amide to the parent amide by $^{19}F$ NMR.

The following was gathered using 3 mol % trifluoromethylthiolated LLDPE:

$^1H$ NMR (500 MHz, C2D2Cl4, 110° C.) δ 3.25 (bs), 1.79 (bs), 1.61 (bs), 1.55 (bs), 1.49 (bs), 1.41 (bs), 1.02 (bs). $^{19}F$ NMR (400 MHz, C2D2Cl4, 80° C.) δ −41.00, −39.87, −39.85. IR (neat, ATR, $cm_{-1}$) 2917, 2849, 1648, 1549, 1464, 1367, 1280, 1277, 1148, 1107, 907, 731, 720. GPC (TCB, 140° C.): M=22 kg/mol, Đ=7.74. TGA (° C.) parent Td=428, product $T_d$=317. DSC (° C.): parent $T_m$=125 with 41% crystallinity (DH=122 J/g), product $T_m$=103 with 12% crystallinity (DH=35.2 J/g).

Determination of percent trifluoromethylthiolation of LLDPE: Upon purification, the percent trifluoromethylation of LLDPE can be determined through integration of the $^1H$ NMR. Considering the composition of the polymer, the peaks between 0.8-2.0 ppm were set to total to 4 protons. The protons alpha the incorporated trifluoromethylthiol group that appear between 3.2-3.3 ppm are used to determine mol % trifluoromethylthiolation per repeat unit. Only secondary C—H trifluoromethylthiolation was observed.

Scheme 41

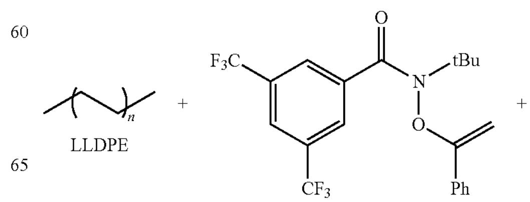

-continued

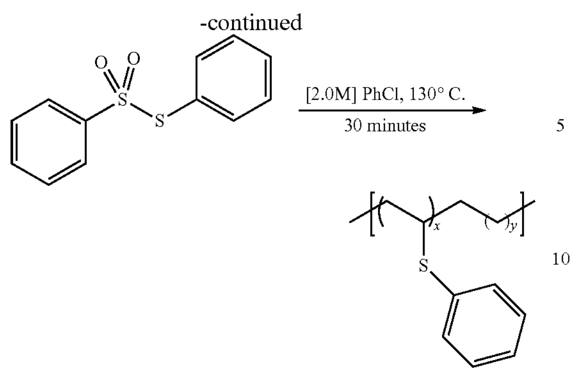

Thiophenolated LLDPE (P5): DOW™ DNDA-1081 NT 7 Linear Low Density Polyethylene Resin, (1-phenylvinyloxy)amide, and S-phenyl benzenesulfonothioate were reacted according to General Procedure I. LLDPE (M=19 kg/mol, Đ=4.76, 19% branched, 40 mg, 1.43 mmol) reacted with (1-phenylvinyloxy)amide (62 mg, 0.14 mmol) and S-phenyl benzenesulfonothioate (72 mg, 0.29 mmol) in chlorobenzene (0.7 mL) upon heating at 130° C. for 30 min. The resultant material (42 mg) was 7 mol % functionalized LLDPE. Collection of the filtrate revealed 90% conversion amide reagent by $^{19}F$ NMR. Employing phenyl disulfide or 2-(phenyldisulfaneyl)pyridine instead of S-phenyl benzenesulfonothioate yielded products with similar NMR peaks and GPC traces of 3 mol % and 4 mol % materials, respectively.

The following was gathered using 7 mol % thiophenolated LLDPE:

$^{1H}$NMR (500 MHz, $C_2D_2Cl_4$, 110° C.) δ 7.52 (bs), 7.37 (bs), 7.30 (bs), 3.19 (bs), 1.74 (bs), 1.62 (bs), 1.61 (bs), 1.45 (bs), 1.37 (bs), 1.04 (bs). IR (neat, ATR, $cm^{-1}$): 2917, 2849, 1586, 1464, 1439, 1279, 1149, 1026, 721, 694, 691. GPC (TCB, 140° C.): M=22 kg/mol, Đ=4.34. TGA (° C.) parent $T_d$=428, product $T_d$=317. DSC (° C.): parent $T_m$=125 with 42% crystallinity (DH=122 J/g), product $T_m$=55 with 10% crystallinity (DH=28 J/g).

Determination of percent thiophenolation of LLDPE: Upon purification, the percent thiophenolation of LLDPE can be determined through integration of the $^1H$ NMR. Considering the composition of the polymer, the peaks between 0.8-2.0 ppm were set to total to 4 protons. The protons alpha the incorporated thiophenol group that appear at 3.2 ppm are used to determine mol % thiophenolation per repeat unit. The aromatic region between 7.30-7.55 ppm were integrated and divided by 5 to confirm the percent incorporation concluded from the alpha protons. Only secondary C—H functionalization was observed.

Azidated LLDPE (P6):

Scheme 42

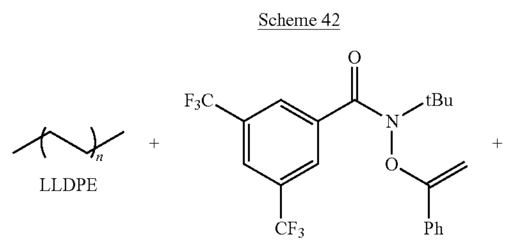

-continued

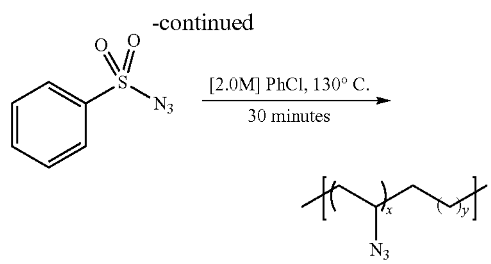

DOW™ DNDA-1081 NT 7 Linear Low Density Polyethylene Resin, (1-phenylvinyloxy)amide, and benzenesulfonyl azide were reacted according to General Procedure I. LLDPE (=19 kg/mol, Đ=4.76, 19% branched, 20 mg, 0.71 mmol) reacted with (1-phenylvinyloxy)amide (31 mg, 0.071 mmol) and benzenesulfonyl azide (26 mg, 0.14 mmol) in chlorobenzene (0.4 mL) upon heating at 130° C. for 30 min. The resultant material (14 mg) was 4 mol % azidated LLDPE. Collection of the filtrate revealed 86% conversion of the amide reagent by $^{19}F$ NMR. Increasing the stoichiometry of the reagents increased the percent incorporation of the azide group.

The following was gathered using 4 mol % azidated LLDPE:

$^{1H}$ NMR (500 MHz, $C_2D_2Cl_4$, 110° C.) δ 3.34 (bs), 1.64 (bs), 1.49 (bs), 1.40 (bs), 1.02 (bs). IR (neat, ATR, $cm^{-1}$) 2917, 2849, 2097, 1464, 1342, 1278, 1247, 1142, 720. GPC (TCB, 140° C.)=20 kg/mol, Đ=3.78. TGA (° C.) parent $T_d$=428, product $T_d$=377. DSC (° C.): parent=125 with 41% crystallinity (DH=122 J/g), product=98 with 10% crystallinity (DH=31 J/g).

Determination of percent azidation of LLDPE: Upon purification, the percent azidation of LLDPE can be determined through integration of the $^1H$ NMR. Considering the composition of the polymer, the peaks between 0.8-2.0 ppm were set to total to 4 protons. The protons alpha the incorporated azide group that appear at 3.3 ppm are used to determine mol % azidation per repeat unit.

Scheme 43

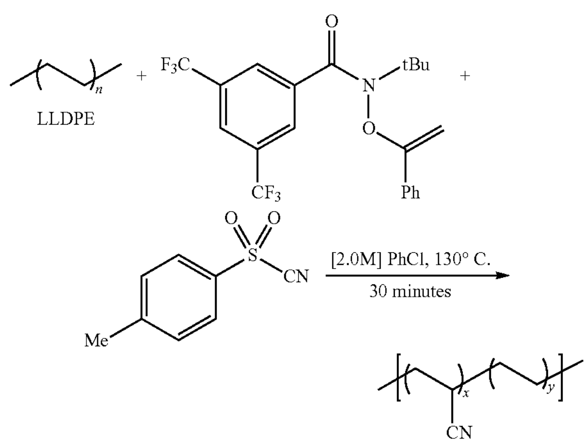

Cyanated LLDPE (P7): DOW™ DNDA-1081 NT 7 Linear Low Density Polyethylene Resin, (1-phenylvinyloxy) amide, and tosyl cyanide were reacted according to General Procedure I. LLDPE ($M_n$=19 kg/mol, Đ=4.76, 19% branched, 40 mg, 1.43 mmol) reacted with (1-phenylvinyloxy)amide (120 mg, 0.29 mmol) and tosyl cyanide (100 mg, 0.57 mmol) in chlorobenzene (0.7 mL) upon heating at 130° C. for 30 min. The resultant material was 7 mol % cyanated LLDPE (36 mg). Similar characterization data was obtained using other stoichiometric ratios of (1-phenylvinyloxy) amide 1 and tosyl cyanide to repeat unit (see Table S1 for exact conditions). See accompanying tables and figures for more information.

The following was gathered using 7 mol % cyanated LLDPE:

$^{1H}$ NMR (500 MHz, $C_2D_2Cl_4$, 110° C.) δ 2.58 (bs), 1.71 (bs), 1.64 (bs), 1.56 (bs), 1.41 (bs), 1.02 (bs). $^{13}$C NMR (101 MHz, $C_2D_2Cl_4$, 80° C.) δ 122.5, 74.3, 74.1, 73.8, 32.4, 32.2, 31.8, 31.6, 29.8, 29.6, 29.2, 27.3, 27.2, 26.9, 23.1, 14.2, 14.2. IR (neat, ATR, $cm^{-1}$) 2918, 2850, 2237, 1467, 1378, 720. GPC (TCB, 140° C.) M=21 kg/mol, Đ=3.98. TGA (° C.) parent $T_d$=428, product $T_d$=339. DSC (° C.): parent $T_m$=125 with 42% crystallinity (DH=122 J/g), product $T_m$=96 with 2% crystallinity (DH=6 J/g).

Determination of percent cyanation of LLDPE: Upon purification, the percent cyanation of LLDPE can be determined through integration of the $^{1}$H NMR. Considering the composition of the polymer, the peaks between 0.8-2.0 ppm were set to total to 4 protons. The protons alpha the incorporated cyano group that appear at 2.6 ppm are used to determine mol % cyanation per repeat unit. Only secondary C—H cyanation was observed in all cases. Table 17 shows results of cyanation of LLDPE at various target functionalizations dictated by the stoichiometry of the reagents. r.u.=repeat unit of the polyolefin. Percent conversion was determined with respect to amide reagent by $^{19}$F NMR. Percent functionalization was determined by $^{1}$H NMR. Molecular weight ($M_n$) and dispersity (Đ) were determined by HT GPC.

TABLE 17

| Reagent Loading (r.u.:amide:trap) | % conversion | % functionalization | $M_n$ | Đ |
|---|---|---|---|---|
| 10:1:2 | 90% | 7 mol % | 19 | 3.93 |
| 10:1:2 | 88% | 6 mol % | 20 | 4.78 |
| 5:1:2 | 85% | 11 mol % | 25 | 3.55 |
| 5:1:2 | 90% | 7 mol % | 21 | 3.85 |

Scheme 44

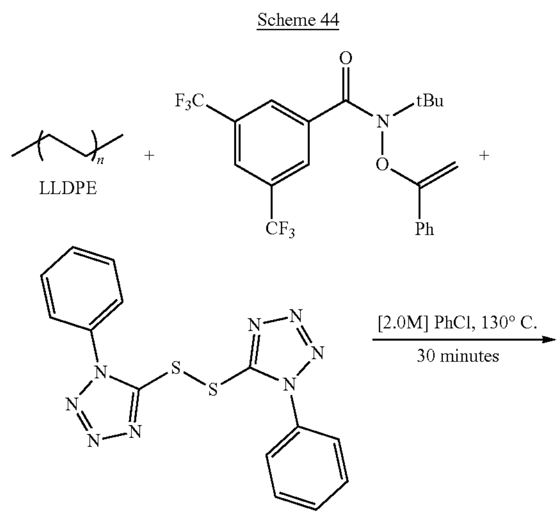

-continued

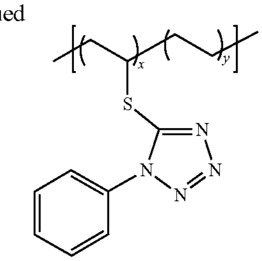

Phenyl tetrazole LLDPE (P8): DOW™ DNDA-1081 NT 7 Linear Low Density Polyethylene Resin, (1-phenylvinyloxy)amide, and phenyl tetrazole dimer were reacted according to General Polymer Procedure. LLDPE (=19 kg/mol, Đ=4.76, 19% branched, 20 mg, 0.71 mmol) reacted with (1-phenylvinyloxy)amide (31 mg, 0.071 mmol) and phenyl tetrazole dimer (51 mg, 0.14 mmol) in chlorobenzene (0.4 mL) upon heating at 130° C. for 30 min. The resultant material (14 mg) was 2 mol % phenyl tetrazolated LLDPE. Collection of the filtrate revealed 82% conversion of the functionalized amide to the parent amide by $^{19}$F NMR.

The following was gathered using 2 mol % phenyl tetrazolated LLDPE:

$^{1H}$ NMR (500 MHz, $C_2D_2Cl_4$, 110° C.) δ 7.63 (bs), 3.96 (bs), 1.83 (bs), 1.46 (bs), 1.35 (bs), 0.96 (bs). IR (neat, ATR, $cm^{-1}$) 2916, 2849, 1599, 1500, 1462, 1394, 1386, 1245, 1238, 1074, 1073, 1017, 1015, 979, 911, 758, 719, 694. GPC (TCB, 140° C.): =21 kg/mol, Đ=5.58. TGA (° C.) parent Td=428, product $T_d$=229 ($T_{d1}$=141, $T_{d2}$=373). DSC (° C.): parent=125 with 41% crystallinity (DH=122 J/g), product=91 with 6% crystallinity (DH=17 J/g).

Determination of percent phenyl tetrazolation of LLDPE: Upon purification, the percent phenyl tetrazolation of LLDPE can be determined through integration of the $^{1}$H NMR. Considering the composition of the polymer, the peaks between 0.8-2.0 ppm were set to total to 4 protons. The protons alpha the incorporated thioether group that appear between 3.9-4.0 ppm are used to determine mol % phenyl tetrazole per repeat unit. These protons were in agreement with the aromatic protons observed around 7.6 ppm.

Scheme 45

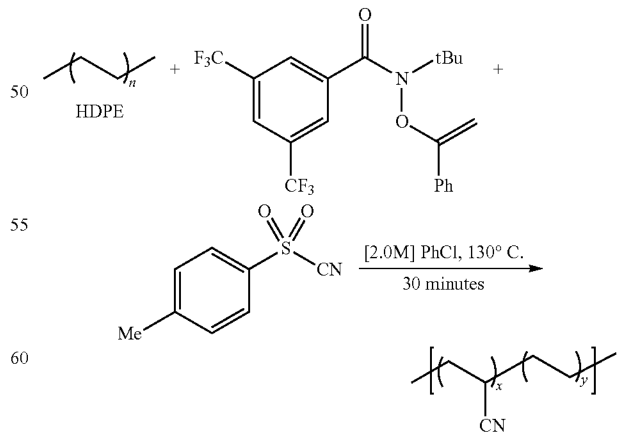

Cyanated HDPE (P9): ExxonMobil™ High Density Polyethylene, (1-phenylvinyloxy)amide, and tosyl cyanide were reacted according to General Procedure I. HDPE (Mn=32 kg/mol, Đ=4.27, 0% branched, 40 mg, 1.43 mmol) reacted with (1-phenylvinyloxy)amide (62 mg, 0.14 mmol) and tosyl cyanide (52 mg, 0.28 mmol) in chlorobenzene (0.7 mL) upon heating at 130° C. for 30 min. The resultant material (22 mg) was 5 mol % cyanated HDPE as whitish flakes. Collection of the filtrate revealed 84% conversion of the amide reagent by $^{19}F$ NMR. The following was gathered using 5 mol % cyanated HDPE:

$^{1}H$ NMR (500 MHz, C2D2Cl4, 110° C.) δ 2.58 (bs), 1.67 (bs), 1.40 (bs), 1.01 (bs). IR (neat, ATR, cm-1) 2916, 2849, 2240, 1473, 1463, 723. GPC (TCB, 140° C.)=28 kg/mol, Đ=5.24. TGA (° C.) parent Td=433, product Td=320. DSC (° C.): parent=129 with 62% crystallinity (DH=183 J/g), product=105 with 20% crystallinity (DH=59 J/g).

Determination of percent cyanation of HDPE: Upon purification, the percent cyanation of HDPE can be determined through integration of the $^{1}H$ NMR. Considering the composition of the polymer, the peaks between 0.8-2.0 ppm were set to total to 4 protons. The protons alpha the incorporated cyano group that appear at 2.6 ppm are used to determine mol % cyanation per repeat unit. Only secondary C—H cyanation was observed.

Scheme 46

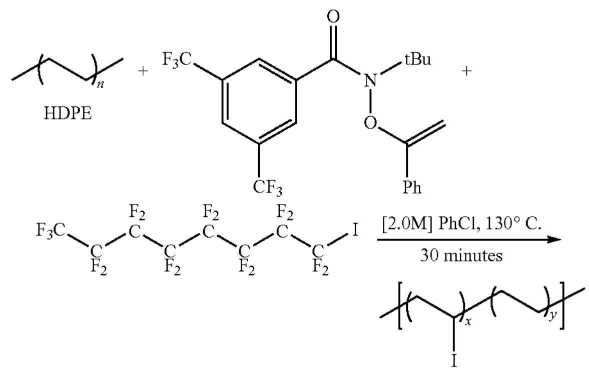

Iodinated HDPE (P10): ExxonMobil™ High Density Polyethylene, (1-phenylvinyloxy)amide, and perfluorooctyl iodide were reacted according to General Procedure I. HDPE (=38 kg/mol, Đ=8.13, 0% branched, 40 mg, 1.43 mmol) reacted with (1-phenylvinyloxy)amide (62 mg, 0.14 mmol) and perfluorooctyl iodide (81 μL, 0.28 mmol) in chlorobenzene (0.7 mL) upon heating at 130° C. for 30 min. The resultant material (44 mg) was 2 mol % iodinated HDPE as whitish flakes. Collection of the filtrate revelated 74% conversion of the amide reagent by $^{19}F$ NMR.

The following was gathered using 2 mol % iodinated HDPE:

$^{1H}$ NMR (500 MHz, $C_2D_2Cl_4$, 110° C.) δ 4.21 (bs), 1.94 (bs), 1.78 (bs), 1.62 (bs), 1.46 (bs), 1.36 (bs), 0.97 (bs). IR (neat, ATR, $cm^{-1}$) 2916, 2849, 1473, 1463, 1281, 1143, 1063, 801, 721, 719. GPC (TCB, 140° C.)=41 kg/mol, Đ=7.38. TGA (° C.) parent $T_d$=433, product $T_d$=251 ($T_{d1}$Đ=202, $T_{d2}$=388). DSC (° C.): parent=129 with 62% crystallinity (DH=183 J/g), product=111 with 26% crystallinity (DH=75 J/g).

Determination of percent iodination of HDPE: Upon purification, the percent iodination of HDPE can be determined through integration of the $^{1}H$ NMR. Considering the composition of the polymer, the peaks between 0.8-2.0 ppm were set to total to 4 protons. The protons alpha the incorporated iodo group that appear at 4.3 ppm are used to determine mol % iodination per repeat unit. Only secondary C—H iodination was observed.

Scheme 47

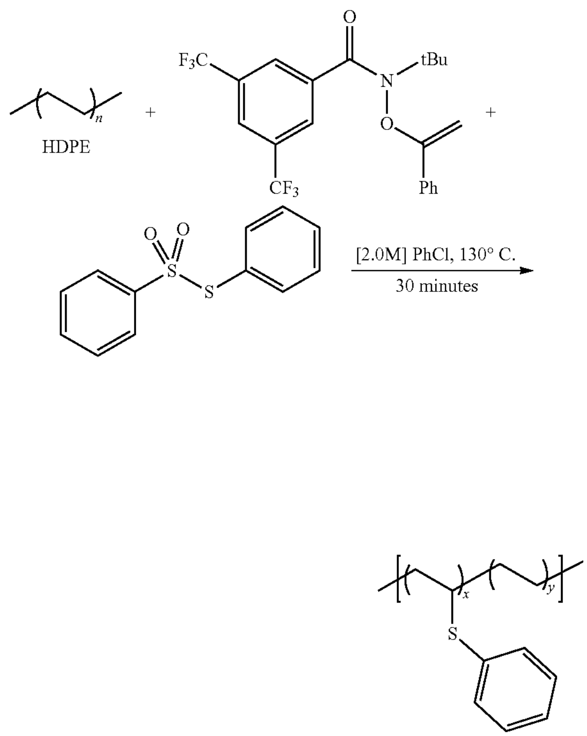

Thiophenolated HDPE (P11): ExxonMobil™ High Density Polyethylene, (1-phenylvinyloxy)amide, and phenyl benzenesulfonate were reacted according to General Procedure I. HDPE (=38 kg/mol, Đ=8.13, 0% branched, 60 mg, 2.1 mmol) reacted with (1-phenylvinyloxy)amide (92 mg, 0.21 mmol) and phenyl benzenesulfonate (110 mg, 0.43 mmol) in chlorobenzene (0.9 mL) upon heating at 130° C. for 30 min. The resultant material (44 mg) was 8 mol % thiophenolated HDPE as whitish flakes. Collection of the filtrate revealed 85% conversion of the amide reagent by $^{19}F$ NMR.

The following was gathered using 8 mol % thiophenolated HDPE:

$^{1H}$ NMR (500 MHz, $C_2D_2Cl_4$, 110° C.) δ 7.43 (bs, 2H), 7.30 (bs, 2H), 7.23 (bs, 1H), 3.10 (bs, 1H), 1.65 (bs), 1.51 (bs), 1.36 (bs), 0.97 (bs). IR (neat, ATR, $cm^{-1}$) 2915, 2849, 1585, 1473, 1463, 1438, 1093, 1027, 1026, 734, 720, 718, 692. GPC (TCB, 140° C.)=43 kg/mol, Đ=7.68. TGA (° C.) parent $T_d$=433, product $T_d$=398. DSC (° C.): parent $T_m$=129 with 62% crystallinity (DH=183 J/g), product $T_m$=124 with 20% crystallinity (DH=57 J/g).

Determination of percent thiophenolation of HDPE: Upon purification, the percent thiophenolation of HDPE can be determined through integration of the $^{1}H$ NMR. Considering the composition of the polymer, the peaks between 0.8-2.0 ppm were set to total to 4 protons. The protons alpha the incorporated thiophenol group that appear at 3.1 ppm are used to determine mol % thiophenolation per repeat unit. The phenyl peaks were found to be in agreement with the alpha protons.

Scheme 48

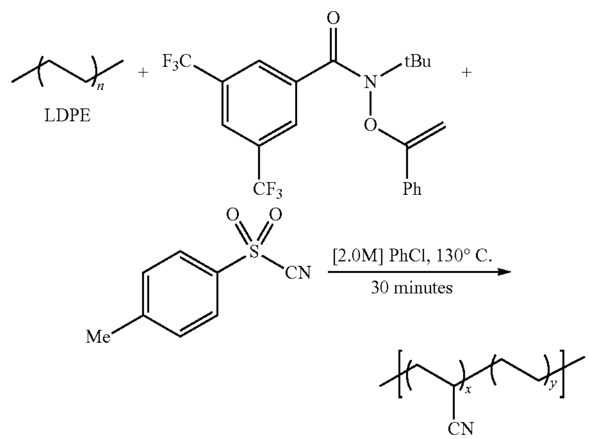

Cyanated LDPE (P12): Dow™ Polyethylene 4012 Low Density, (1-phenylvinyloxy)amide, and tosyl cyanide were reacted according to General Procedure I. LDPE (M=34 kg/mol, Đ=13.5, 49% branched, 40 mg, 1.43 mmol) reacted with (1-phenylvinyloxy)amide (62 mg, 0.14 mmol) and tosyl cyanide (52 mg, 0.28 mmol) in chlorobenzene (0.7 mL) upon heating at 130° C. for 30 min. The resultant material (28 mg) was 5 mol % cyanated LDPE as whitish flakes. Collection of the filtrate revealed 89% conversion of the amide reagent by $^{19}$F NMR.

The following was gathered using 5 mol % cyanated LDPE:

$^{1H}$ NMR (500 MHz, C2D2Cl4, 110° C.) δ 2.54 (bs), 1.66 (bs), 1.50 (bs), 1.44 (bs), 1.36 (bs), 0.97 (bs). IR (neat, ATR, $cm^{-1}$) 2917, 2849, 2239, 1724, 1468, 1378, 1280, 1039, 720. GPC (TCB, 140° C.) M=40 kg/mol, Đ=13.56. TGA (° C.) parent Td=416, product Td=341. DSC (° C.): parent $T_m$=105 with 36% crystallinity (DH=105 J/g), product $T_m$=82 with 10% crystallinity (DH=28 J/g).

Determination of percent cyanation of LDPE: Upon purification, the percent cyanation of LDPE can be determined through integration of the $^1$H NMR. Considering the composition of the polymer, the peaks between 0.8-2.0 ppm were set to total to 4 protons. The protons alpha the incorporated cyano group that appear at 2.6 ppm are used to determine mol % cyanation per repeat unit. Only secondary C—H cyanation was observed.

Scheme 49

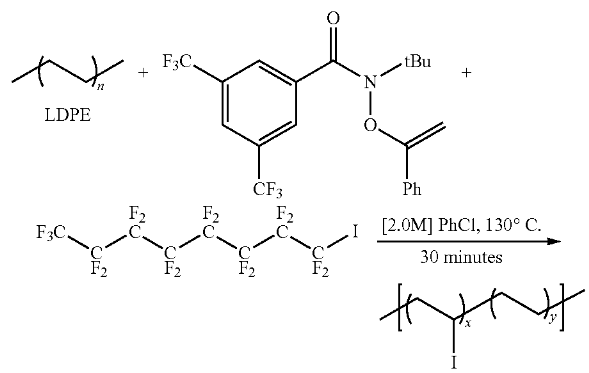

Iodinated LDPE (P13): Dow™ Polyethylene 4012 Low Density, (1-phenylvinyloxy)amide, and perfluorooctyl iodide were reacted according to General Procedure I. LDPE (=41 kg/mol, Đ=17.10, 49% branched, 40 mg, 1.43 mmol) reacted with (1-phenylvinyloxy)amide (62 mg, 0.14 mmol) and perfluorooctyl iodide (81 tL, 0.28 mmol) in chlorobenzene (0.7 mL) upon heating at 130° C. for 30 min. The resultant material (46 mg) was 3 mol % iodinated LDPE as whitish flakes. Collection of the filtrate revealed 75% conversion of the amide reagent $^{19}$F NMR.

The following was gathered using 3 mol % iodinated LDPE:

$^{1H}$ NMR (500 MHz, C2D2Cl4, 110° C.) δ 4.21 (bs), 1.97 (bs), 1.80 (bs), 1.57 (bs), 1.46 (bs), 1.36 (bs), 0.97 (bs). IR (neat, ATR, $cm^{-1}$) 2916, 2849, 1465, 1463, 1368, 1281, 1217, 1214, 1145, 719. GPC (TCB, 140° C.)=49 kg/mol, Đ=15.16. TGA (° C.) parent Td=416, product Td=245 (Td1=189, Td2=383). DSC (° C.): parent=105 with 36% crystallinity (DH=105 J/g), product=89 with 16% crystallinity (DH=46 J/g).

Determination of percent iodination of LDPE: Upon purification, the percent iodination of LDPE can be determined through integration of the $^1$H NMR. Considering the composition of the polymer, the peaks between 0.8-2.0 ppm were set to total to 4 protons. The protons alpha the incorporated iodo group that appear at 4.2 ppm are used to determine mol % iodination per repeat unit. Only secondary C—H iodination was observed.

Scheme 50

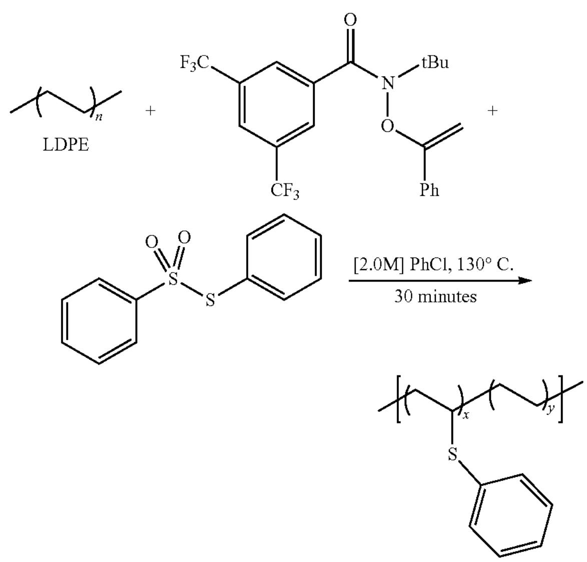

Thiophenolated LDPE (P14): Dow™ Polyethylene 4012 Low Density, (1-phenylvinyloxy)amide, and phenyl benzenesulfonate were reacted according to General Procedure I. LDPE (=34 kg/mol, Đ=13.5, 49% branched, 40 mg, 1.43 mmol) reacted with (1-phenylvinyloxy)amide (62 mg, 0.14 mmol) and phenyl benzenesulfonate (72 mg, 0.28 mmol) in chlorobenzene (0.7 mL) upon heating at 130° C. for 30 min. The resultant material (34 mg) was 6 mol % phenyl thioether LDPE as whitish flakes. Collection of the filtrate revealed 93% conversion of amide reagent by $^{19}$F NMR.

The following was gathered using 6 mol % thiophenolated LDPE:

[1H] NMR (500 MHz, C2D2Cl4, 110° C.) δ 7.44 (bs, 2H), 7.31 (bs, 2H), 7.23 (bs, 1H), 3.11 (bs, 1H), 1.66 (bs), 1.53 (bs), 1.36 (bs), 0.98 (bs). IR (neat, ATR, $cm^{-1}$) 2917, 2850, 1585, 1464, 1438, 1366, 1280, 1141, 1092, 1068, 1025, 746, 720, 691. GPC (TCB, 140° C.) M=65 kg/mol, Đ=13.76. TGA (° C.) parent Td=416, product Td=391. DSC (° C.): parent $T_m$=105 with 36% crystallinity (DH=105 J/g), product $T_m$=74 with 11% crystallinity (DH=32 J/g).

Determination of percent thiophenolation of LDPE: Upon purification, the percent thiophenolation of LDPE can be determined through integration of the $^1$H NMR. Considering the composition of the polymer, the peaks between 0.8-2.0 ppm were set to total to 4 protons. The protons alpha the incorporated thiophenol group that appear at 3.1 ppm are used to determine mol % thiophenol per repeat unit. Only secondary C—H thiophenolation was observed. The phenyl peaks were found to be in agreement with the alpha protons.

Scheme 51

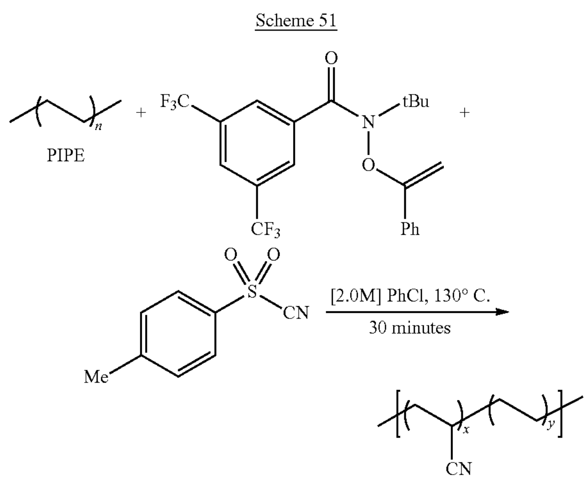

Cyanated PIPE (P15): Post-industrial PE (PIPE) gathered from remnants of packaging forms, (1-phenylvinyloxy) amide, and tosyl cyanide were reacted according to General Procedure I. PIPE (M=45 kg/mol, Đ=8.65, 40 mg, 1.43 mmol) reacted with (1-phenylvinyloxy)amide (62 mg, 0.14 mmol) and tosyl cyanide (52 mg, 0.28 mmol) in chlorobenzene (0.7 mL) upon heating at 130° C. for 30 min. The resultant material (30 mg) was 5 mol % cyanated PIPE as whitish flakes. Collection of the filtrate revealed 90% conversion of the amide reagent by $^{19}$F NMR.

The following was gathered using 5 mol % cyanated PIPE:

[1H] NMR (500 MHz, $C_2D_2Cl_4$, 110° C.) δ 2.53 (bs), 1.66 (bs), 1.62 (bs), 1.52 (bs), 1.44 (bs), 1.36 (bs), 1.25 (bs), 0.98 (bs). IR (neat, ATR, $cm^{-1}$) 2917, 2850, 2240, 1468, 1378, 1000, 720. GPC (TCB, 140° C.) M=48 kg/mol, Đ=8.44. TGA (° C.) parent $T_d$=412, product $T_d$=393. DSC (° C.): parent $T_m$=109 with 24% crystallinity (DH=72 J/g), product $T_m$=87 with 21% crystallinity (DH=60 J/g).

Determination of percent cyanation of PIPE: Upon purification, the percent cyanation of PIPE can be determined through integration of the $^1$H NMR. Considering the composition of the polymer, the peaks between 0.8-2.0 ppm were set to total to 4 protons. The protons alpha the incorporated cyano group that appear at 2.6 ppm are used to determine mol % cyanation per repeat unit. Only secondary C—H cyanation was observed.

Scheme 52

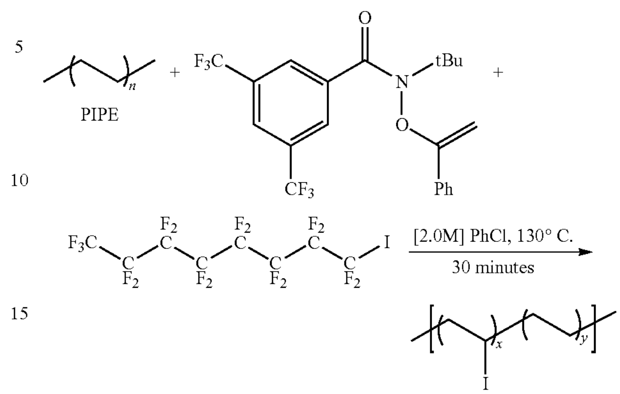

Iodinated PIPE (P16): Post-industrial PE (PIPE) gathered from remnants of packaging forms, (1-phenylvinyloxy) amide, and perfluorooctyl iodide were reacted according to General Procedure I. PIPE (=48 kg/mol, Đ=14.07, 40 mg, 1.43 mmol) reacted with (1-phenylvinyloxy)amide (62 mg, 0.14 mmol) and perfluorooctyl iodide (81 jtL, 0.28 mmol) in chlorobenzene (0.7 mL) upon heating at 130° C. for 30 min. The resultant material (47 mg) was 4 mol % iodinated PIPE as whitish flakes. Collection of the filtrate revealed 75% conversion of the amide reagent by $^{19}$F NMR.

The following was gathered using 4 mol % iodinated PIPE:

$^1$H NMR (500 MHz, C2D2Cl4, 110° C.) δ. IR (neat, ATR, cm-$^1$) 2916, 2849, 1473, 1464, 1366, 1281, 1241, 1216, 1146, 730, 719. GPC (TCB, 140° C.)=57 kg/mol, Đ=12.60. TGA (° C.) parent Td=412, product Td=234 (Td1=197, Td2=383). DSC (° C.): parent=109 with 24% crystallinity (DH=72 J/g), product=88 with 13% crystallinity (DH=37 J/g).

Determination of percent iodination of PIPE: Upon purification, the percent iodination of PIPE can be determined through integration of the 1H NMR. Considering the composition of the polymer, the peaks between 0.8-2.0 ppm were set to total to 4 protons. The protons alpha the incorporated iodo group that appear at 4.2 ppm are used to determine mol % iodination per repeat unit. Only secondary C—H iodination was observed.

Scheme 53

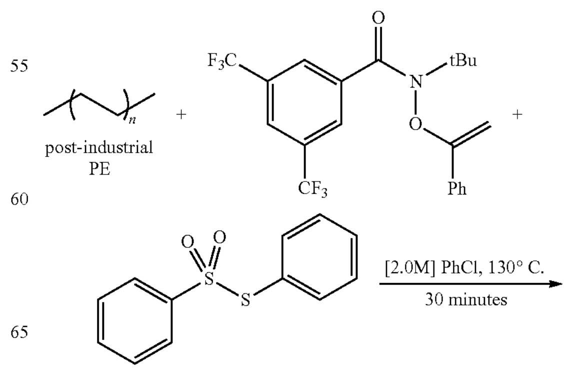

-continued

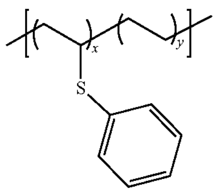

Thiophenolated PIPE (P17): Post-industrial PE (PIPE) gathered from remnants of packaging forms, (1-phenylvinyloxy)amide, and phenyl benzenesulfonate were reacted according to General Procedure I. PIPE (=48 kg/mol, Đ=14.07, 40 mg, 1.43 mmol) reacted with (1-phenylvinyloxy)amide (62 mg, 0.14 mmol) and phenyl benzenesulfonate (72 mg, 0.28 mmol) in chlorobenzene (0.7 mL) upon heating at 130° C. for 30 min. The resultant material (37 mg) was 6 mol % thiophenolated PIPE as whitish flakes. Collection of the filtrate revealed 91% conversion of the amide reagent by $^{19}$F NMR.

The following was gathered using 6 mol % thiophenolated PIPE:

$^{1H}$ NMR (500 MHz, $C_2D_2Cl_4$, 110° C.) δ 7.44 (bs, 2H), 7.30 (bs, 2H), 7.23 (bs, 1H), 3.11 (bs, 1H), 1.66 (bs), 1.52 (bs), 1.44 (bs), 1.36 (bs), 0.97 (bs). IR (neat, ATR, $cm^{-1}$) 2917, 2849, 1739, 1586, 1467, 1438, 1370, 1279, 1242, 1090, 1068, 1026, 746, 694, 692. GPC (TCB, 140° C.)=66 kg/mol, Đ=11.73. TGA (° C.) parent $T_d$=412, product $T_d$=391. DSC (° C.): parent=109 with 24% crystallinity (DH=72 J/g), product=76 with 8% crystallinity (DH=24 J/g).

Determination of percent thiophenolation of PIPE: Upon purification, the percent thiophenolation of PIPE can be determined through integration of the $^{1}$H NMR. Considering the composition of the polymer, the peaks between 0.8-2.0 ppm were set to total to 4 protons. The protons alpha the incorporated thiophenol group that appear at 3.1 ppm are used to determine mol % thiophenolation per repeat unit. The phenyl protons were in agreement with the alpha protons.

Scheme 54

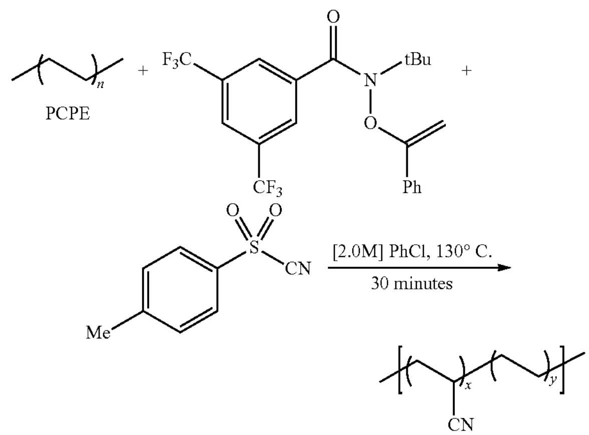

Cyanated PCPE (P18): Post-consumer PE (PCPE) gathered from PE foam television packaging, (1-phenylvinyloxy)amide, and tosyl cyanide were reacted according to General Procedure I. PCPE (=34 kg/mol, Đ=7.80, 40 mg, 1.43 mmol) reacted with (1-phenylvinyloxy)amide (60 mg, 0.14 mmol) and tosyl cyanide (52 mg, 0.28 mmol) in chlorobenzene (0.7 mL) upon heating at 130° C. for 30 min. The resultant material (36 mg) was 6 mol % cyanated PCPE as whitish flakes. Collection of the precipitate confirmed 90% conversion of the amide $^{19}$F NMR.

The following was gathered using 7 mol % cyanated PCPE:

1H NMR (500 MHz, C2D2Cl4, 110° C.) δ 2.60 (bs), 1.67 (bs), 1.44 (bs), 1.37 (bs), 0.99 (bs). IR (neat, ATR, cm-1): 2916, 2849, 2239, 1681, 1468, 1379, 1305, 1278, 1152, 1146, 1129, 1038, 1012, 812, 719. GPC (TCB, 140° C.) M=33 kg/mol, Đ=7.34. TGA (° C.) parent Td=414° C., product Td=370° C. DSC (° C.): parent Tm=111° C. with 37% crystallinity (DH=111 J/g), product Tm=89° C. with 16% crystallinity (DH=48 J/g).

Determination of percent cyanation of PCPE: Upon purification, the percent cyanation of PCPE can be determined through integration of the 1H NMR. Considering the composition of the polymer, the peaks between 0.8-2.0 ppm were set to total to 4 protons. The protons alpha the incorporated cyano group that appear at 2.6 ppm are used to determine mol % cyanation per repeat unit. Only secondary C—H cyanation was observed.

Scheme 55

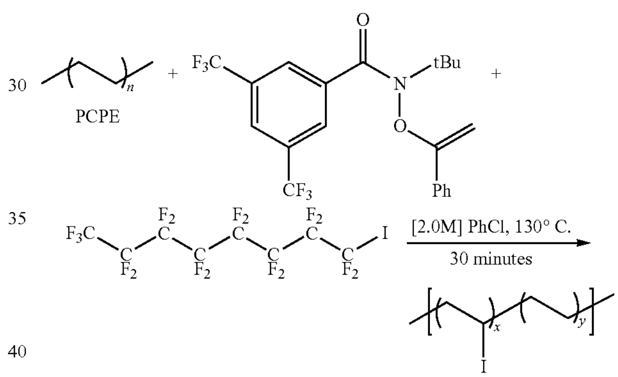

Iodinated PCPE (P19): Post-consumer PE (PCPE) gathered from PE foam television packaging, (1-phenylvinyloxy)amide, and perfluorooctyl iodide were reacted according to General Procedure I. PCPE (M=40 kg/mol, Đ=12.08, 40 mg, 1.43 mmol) reacted with (1-phenylvinyloxy)amide (60 mg, 0.14 mmol) and perfluorooctyl iodide (81 jtL, 0.28 mmol) in chlorobenzene (0.7 mL) upon heating at 130° C. for 30 min. The resultant material (47 mg) was 3 mol % iodinated PCPE as whitish flakes. Collection of the precipitate confirmed 74% conversion of the amide reagent by $^{19}$F NMR.

The following was gathered using 3 mol % iodinated PCPE:

$^{1}$H NMR (500 MHz, C2D2Cl4, 110° C.) δ 4.21 (bs), 1.94 (bs), 1.80 (bs), 1.61 (bs), 1.57 (bs), 1.45 (bs), 1.36 (bs), 0.97 (bs). IR (neat, ATR, cm-$^{1}$) 2916, 2849, 1473, 1462, 1367, 1281, 1238, 1216, 1146, 722, 719. GPC (TCB, 140° C.) Mn=44 kg/mol, Đ=11.36. TGA (° C.) parent Td=414, product Td=231 (Td1=190, Td2=385). DSC (° C.): parent Tm=111° C. with 37% crystallinity (DH=111 J/g), product Tm=95° C. with 18% crystallinity (DH=52 J/g).

Determination of percent iodination of PCPE: Upon purification, the percent iodination of PCPE can be determined through integration of the 1H NMR. Considering the composition of the polymer, the peaks between 0.8-2.0 ppm were set to total to 4 protons. The protons alpha the incorporated iodo group that appear at 4.2 ppm are used to determine mol % iodination per repeat unit. Only secondary C—H iodination was observed.

Scheme 56

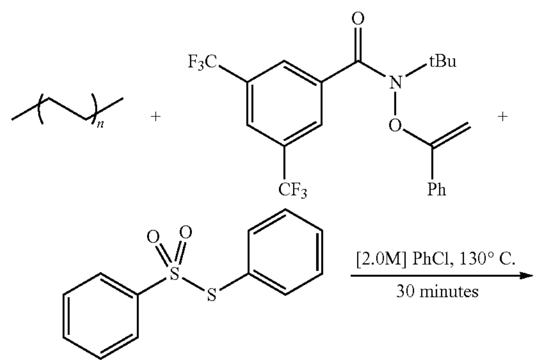

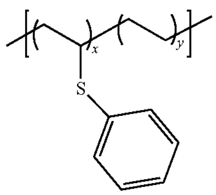

Thiophenolated PCPE (P20): Post-consumer PE (PCPE) gathered from PE foam television packaging, (1-phenylvinyloxy)amide, and phenyl benzenesulfonate were reacted according to General Procedure I. PCPE (=40 kg/mol, Đ=12.08, 40 mg, 1.43 mmol) reacted with (1-phenylvinyloxy)amide (60 mg, 0.14 mmol) and phenyl benzenesulfonate (72 mg, 0.28 mmol) in chlorobenzene (0.7 mL) upon heating at 130° C. for 30 min. The resultant material (35 mg) was 6 mol % thiophenolated PCPE as whitish flakes. Collection of the precipitate confirmed 91% conversion of the amidyl reagent to the parent amide by $^{19}F$ NMR.

The following was gathered using 6 mol % thiophenolated PCPE:

$^{1H}$ NMR (500 MHz, $C_2D_2Cl_4$, 110° C.) δ 7.50 (bs, 2H), 7.36 (bs, 2H), 7.29 (bs, 1H), 3.16 (bs, 1H), 1.71 (bs), 1.58 (bs), 1.50 (bs), 1.41 (bs), 1.03 (bs). IR (neat, ATR, $cm^{-1}$) 2916, 2848, 1584, 1467, 1439, 1369, 1304, 1093, 1027, 1025, 718, 694, 692. GPC (TCB, 140° C.)=55 kg/mol, Đ=10.25. TGA (° C.) parent $T_d$=414, product $T_d$=392. DSC (° C.): parent=111° C. with 37% crystallinity (DH=111 J/g), product=79° C. with 9% crystallinity (DH=26 J/g).

Determination of percent thiophenolation of PCPE: Upon purification, the percent thiophenolation of PCPE can be determined through integration of the $^{1}H$ NMR. Considering the composition of the polymer, the peaks between 0.8-2.0 ppm were set to total to 4 protons. The protons alpha the incorporated thiophenol group that appear at 3.1 ppm are used to determine mol % thiophenol per repeat unit. The phenyl protons were in agreement with the alpha protons.

Scheme 57

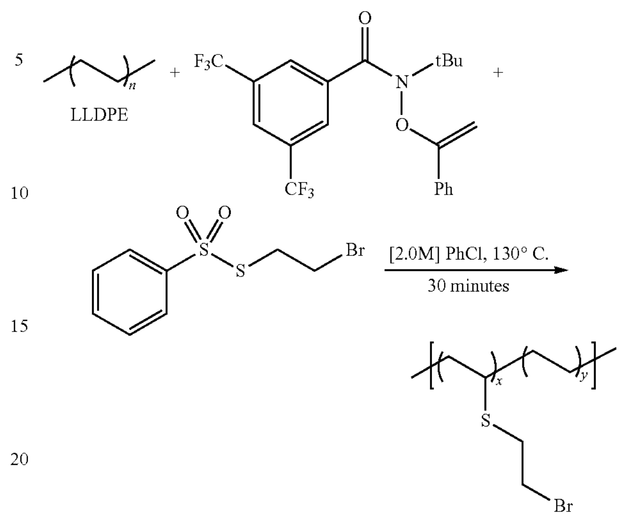

Bromoethylthiolated LLDPE (P21): DOW™ DNDA-1081 NT 7 Linear Low Density Polyethylene Resin, (1-phenylvinyloxy)amide, and S-(2-bromoethyl)benzenesulfonothioate were reacted according to General Polymer Procedure. LLDPE (=18 kg/mol, Đ=9.31, 19% branched, 40 mg, 1.43 mmol) reacted with (1-phenylvinyloxy)amide (62 mg, 0.14 mmol) and S-(2-bromoethyl)benzenesulfonothioate (80 mg, 0.29 mmol) in chlorobenzene (0.7 mL) upon heating at 130° C. for 30 min. The resultant material (44 mg) was 5 mol % bromoethylthiolated LLDPE. Collection of the filtrate revealed 86% conversion of the amide reagent by $^{19}F$ NMR.

The following was gathered using 5 mol % bromoethylthiolated LLDPE:

$^{1H}$ NMR (500 MHz, $C_2D_2Cl_4$, 110° C.) δ 3.53 (bs, 2H), 3.00 (bs, 2H), 2.68 (bs, 1H), 1.63 (bs), 1.49 (bs), 1.36 (bs), 0.98 (bs). IR (neat, ATR, $cm^{-1}$) 2917, 2849, 1577, 1541, 1473, 1463, 1369, 1279, 1250, 1188, 1140, 722, 720. GPC (TCB, 140° C.): =25 kg/mol, Đ=9.32. TGA (° C.) parent $T_d$=428, product $T_d$=235 ($T_{d1}$=159, $T_{d2}$=380). DSC (° C.): parent=125 with 41% crystallinity (DH=122 J/g), product=100 with 11% crystallinity (DH=32 J/g).

Determination of percent bromoethylthiolation of LLDPE: Upon purification, the percent bromoethylthiolation of LLDPE can be determined through integration of the $^{1}H$ NMR. Considering the composition of the polymer, the peaks between 0.8-2.0 ppm were set to total to 4 protons. The protons alpha the incorporated bromo group that appear around 3.5 ppm are used to determine mol % bromoethylthiolation per repeat unit. The protons alpha the bromide atom were in agreement with the protons alpha the sulfur atom. Only secondary C—H functionalization was observed.

Scheme 58

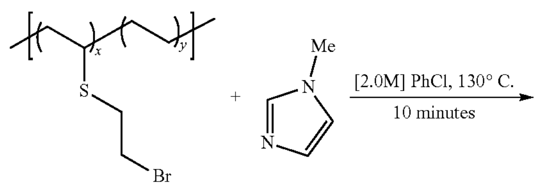

-continued

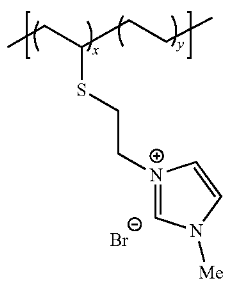

Imidazolium-functional LLDPE (P22): Bromoethylthiolated LLDPE (5 mol % funct, 590 mg, 21 mmol polyolefin, 1.1 mmol bromoethylthiol) reacted with methyl imidazole (1.7 mL, 21 mmol) in chlorobenzene (7 mL) upon heating at 130° C. for 10 min. The resultant material (582 mg) was 4 mol % imidazolium-functional LLDPE.

The following was gathered using 4 mol % imidazolium-functional LLDPE:

$_1$H NMR (500 MHz, $C_2D_2Cl_4$, 110° C.) δ 10.55 (bs, 1H), 7.30 (bs, 2H), 4.62 (bs, 2H), 4.14 (bs, 3H), 3.13 (bs, 2H), 2.73 (bs, 1H), 1.63 (bs), 1.46 (bs), 1.36 (bs), 0.98 (bs). IR (neat, ATR, $cm^{-1}$) 3409, 3105, 3046, 2917, 2850, 1573, 1468, 1279, 1172, 732, 719. TGA (° C.) parent $T_d$=428, product $T_d$=257 ($T_{d1}$=200, $T_{d2}$=343). DSC (° C.): parent=125 with 41% crystallinity (DH=122 J/g), product=97 with 5% crystallinity (DH=14 J/g).

Determination of percent imidazolium functionalization of LLDPE: Upon purification, the percent imidazolium functionalization of LLDPE can be determined through integration of the $^{1H}$ NMR. Considering the composition of the polymer, the peaks between 0.8-2.0 ppm were set to total to 4 protons. The protons alpha the incorporated imidazolium group that appear around 4.6 ppm are used to determine mol % functionalization per repeat unit. The protons alpha the imidazolium moiety were in agreement with the other protons located along on the side chain.

Only secondary C—H functionalization was observed.

Example 8: Tensile Testing Experiments

Polymer films (0.1-0.3 mm) suitable for dynamic mechanical analysis (DMA) were prepared by melt-pressing using a PHI Manual Compression Press. DOW™ DNDA-1081 NT 7 Linear Low Density Polyethylene Resin (LLDPE) and 4 mol % imidazolium bromide LLDPE ($Im^+$-LLDPE) samples between two Kapton films (pre-treated with Frekote 770-NC) were placed between steel electrically heated platens at force 5000 psi and 150° C. for 3 minutes. Brass shims of 4 to 12 mil thickness were used to control ultimate film thickness. Films were removed from the melt press at the indicated temperature and quenched to room temperature by rapid heat transfer to an aluminum surface.

Specimens for analysis were cut into dog-bones using an ISO 527 Type 5B cutting die to standard dimensions. Test specimens were affixed to hand-tightened rubber grips on an Instron 5566 Universal Testing Machine. Tensile stress and strain were measured at room temperature using an extension speed of 1.0 mm/s. Measurements were repeated for at least 3 specimens and the values reported are averaged from the measured data. (Table 18)

TABLE 18

DMA results from thin film tensile axial pull of 0.2 mm thick LLDPE and 0.2 mm thick $Im^+$-LLDPE samples at a rate of 1.0 mm/s.

| Polymer | E (MPa) | $\sigma_b$ (MPa) | $\varepsilon_B$ | $U_T$ (MPa) |
|---|---|---|---|---|
| LLDPE | 25 | 12 | 275% | 413 |
| LLDPE | 29 | 13 | 283% | 444 |
| LLDPE | 28 | 13 | 191% | 303 |
| LLDPE average | 27 | 13 | 250% | 387 |
| LLDPE st. dev. | 2 | 1 | 51% | 74 |
| $Im^+$-LLDPE | 1.7 | 14 | 738% | 694 |
| $Im^+$-LLDPE | 1.9 | 16 | 686% | 745 |
| $Im^+$-LLDPE | 2.1 | 14 | 602% | 648 |
| $Im^+$-LLDPE average | 1.9 | 15 | 675% | 696 |
| $Im^+$-LLDPE st. dev. | 0.2 | 1 | 69% | 49 |

Example 10: Preparation of a N-iPr Hydroxamate

Reactions were completed as depicted in Scheme 59.

Scheme 59

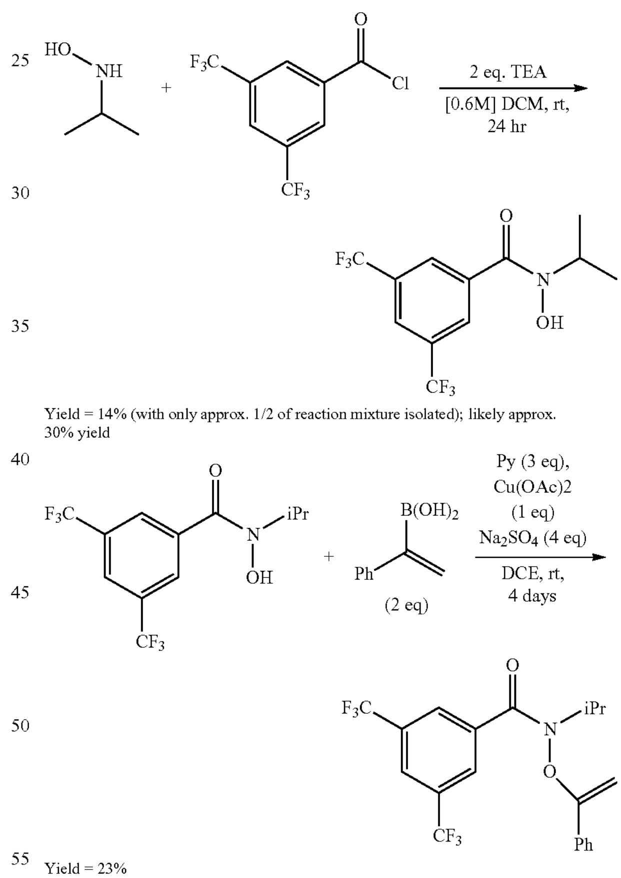

Example 11: C—H Functionalization Using a N-iPr Hydroxamate

Reactions were completed as depicted in Schemes 60 and 61. The results show the efficacy of hydroxamates where one of R1[a], R1[b] and R1[c] is hydrogen.

Scheme 59: Full conversion; 69% amide; <5% acetophenone; 11% acetophenone dimer. All yields based on crude NMR.

Scheme 60
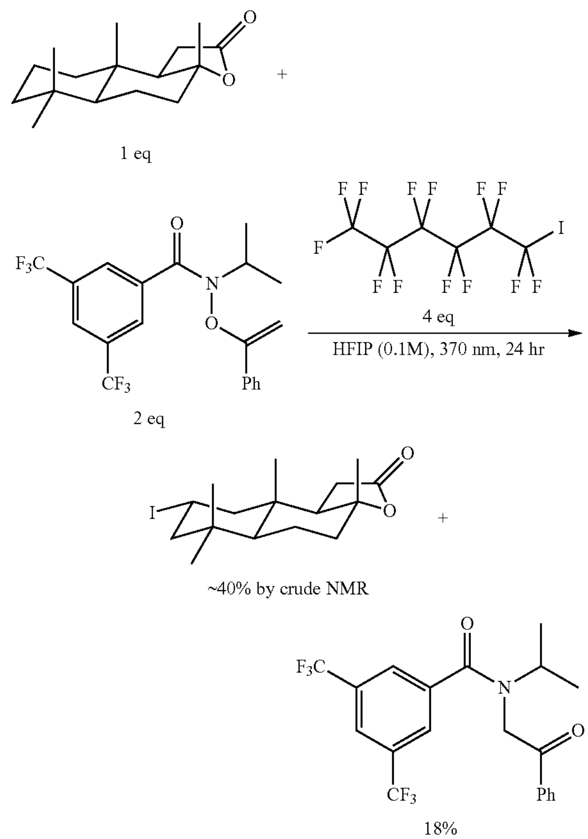
Scheme 61
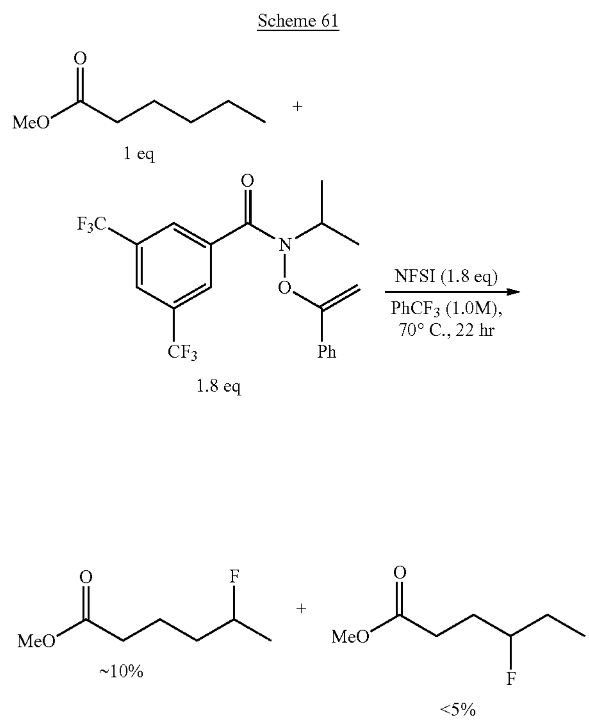
Example 12: Comparative C—H Functionalization
Reactions were completed as depicted in Schemes 62 and 63.
Scheme 62
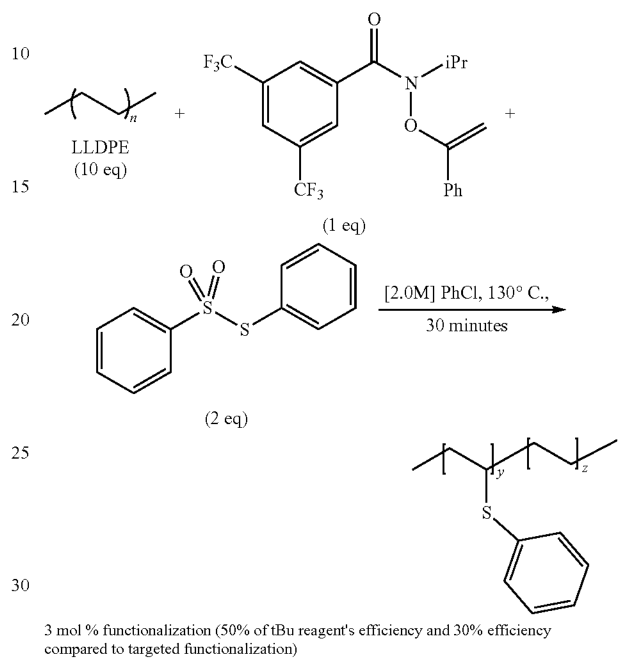
3 mol % functionalization (50% of tBu reagent's efficiency and 30% efficiency compared to targeted functionalization)
Scheme 63
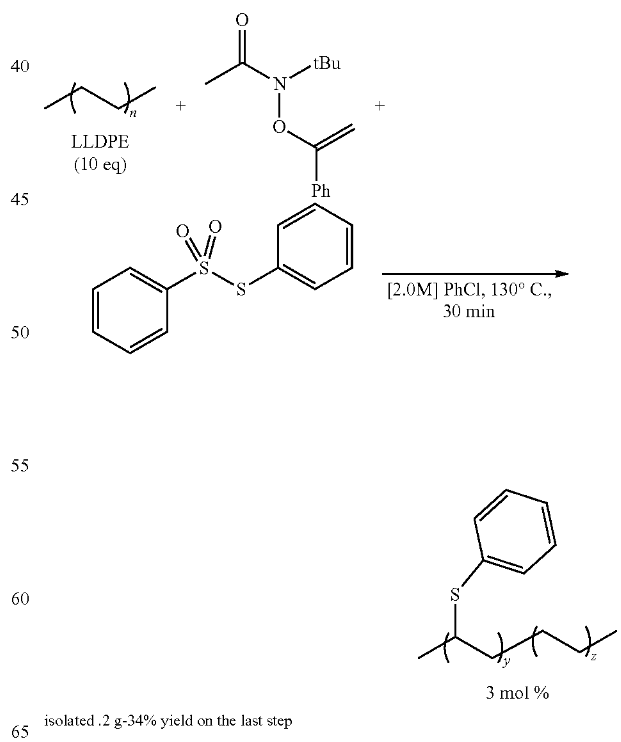
isolated .2 g-34% yield on the last step

Example 13: Synthesis of Exemplary Formula TA-1 Compound

Figure 15:
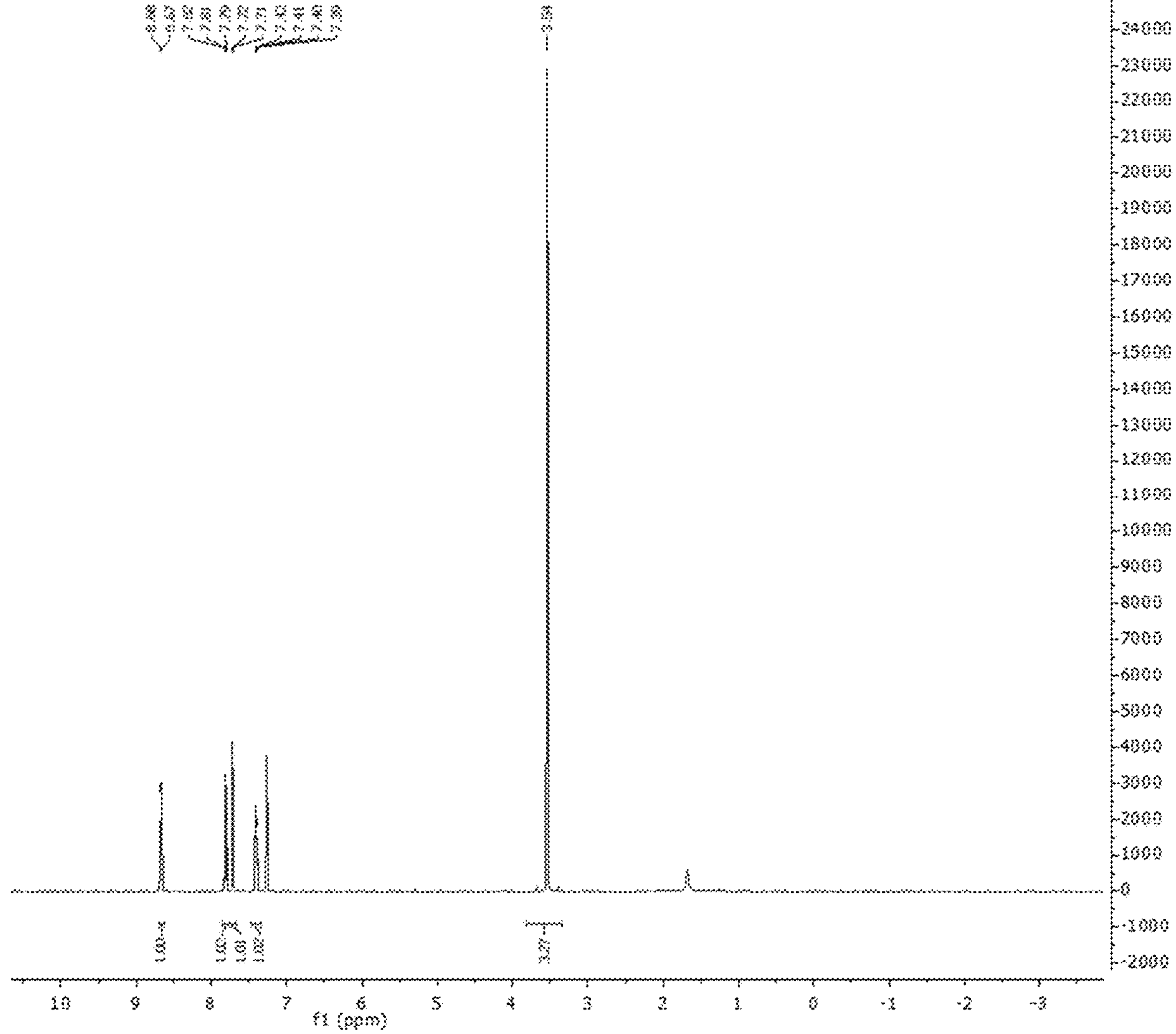
FIG. 15 is a NMR spectra for an exemplary compound of Formula TA-1.

Reactions were completed as depicted in Scheme 64. NMR data are depicted in FIG. 15.

Scheme 64

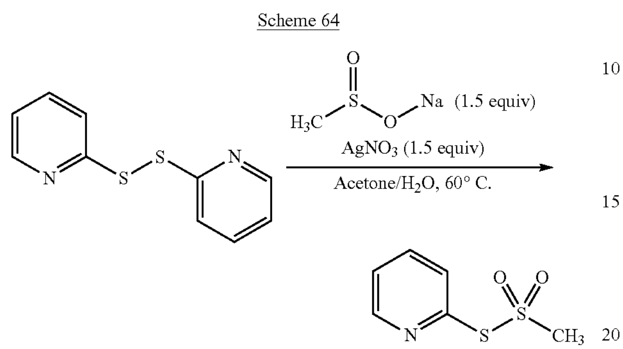

Example 14: C—H Heteroaryl Functionalization

A variety of heterocyclic sulfones of Formula TA-1 were used to demonstrate C—H heteroarylation. Reactions were completed as depicted in Scheme 65.

Scheme 65

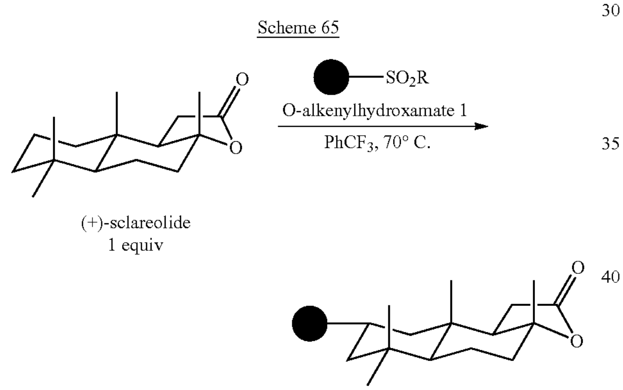

Results are shown in the table below.

18

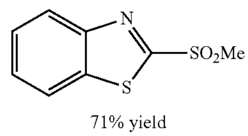

71% yield

19

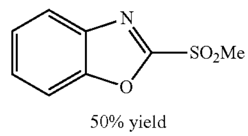

50% yield

20

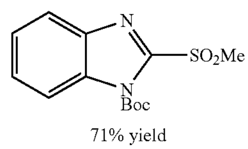

71% yield

-continued

21

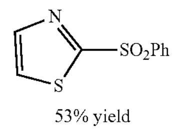

53% yield

22

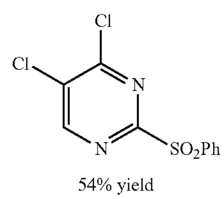

54% yield

23

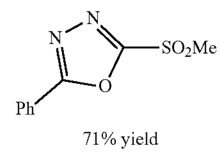

71% yield

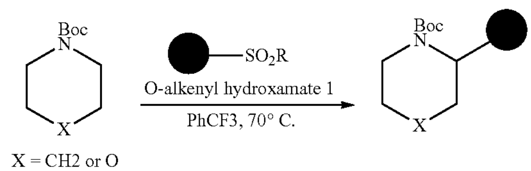

24

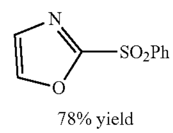

78% yield

25

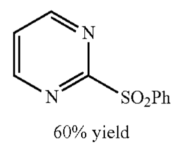

60% yield

26

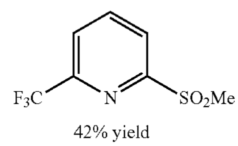

42% yield

27

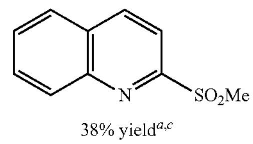

38% yield[a,c]

28

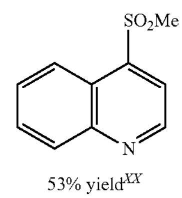

53% yield[XX]

Experiments were performed for the C—H benzothiazolylation of a range of simple substrates using reagent 1 and 2-(methylsulfonyl)benzothiazole as coupling partner in $PhCF_3$ at 70° C. (Scheme B). The reactions of common cyclic and bridged hydrocarbons provided the C—H heteroarylation products 2-6 in good yield (58-75%). Notably, the functionalization of norbornane proceeded with excellent exo stereoselectivity (>20:1 dr), and that of adamantane provided a single regioisomer resulting from functionalization at the less hindered tertiary C—H site. The reaction of 2-adamantanone occurred selectively at the more electron-rich tertiary C—H site distal from the ketone functionality; previous heteroarylation of this substrate using decatungstate as catalyst proceeded with modest regioselectivity. (76) Simple heterocycles also reacted efficiently, delivering products 7-9 with excellent regioselectivity and good yield (47-91% yield).

The functionalization of N-Boc morpholine delivered a single regioisomer (8), in contrast to decatungstate-catalyzed functionalization of this substrate. (76) Heteroarylation of [2.2.1] oxabicycloheptane produced product 10 in moderate yield (44%), but with high diastereoselectivity. Linear substrates also participate in the reaction, as demonstrated by the functionalization of the pinacol acetal of 2-pentanone, providing 11 albeit with modest regioselectivity.

A major advantage of this system is the efficient reactivity achieved with substrate as limiting reagent-critical to applications in late-stage functionalization. As shown in Scheme B, a diverse sample of complex molecules was successfully functionalized, enabling the direct, site-selective introduction of heteroaromatic groups in a practical manner. Heteroarylation of differin (adapalene) precursor 1-(5-bromo-2-methoxyphenyl) adamantane afforded product 13 in 54% isolated yield. As observed with adamantane and 2-adamantanone, the reaction was highly regioselectivity for the least sterically encumbered tertiary C—H bond. LSF of the terpenoid natural product (+)-longifolene proceeded exclusively at the least hindered methylene site, demonstrating the ability to perform the C—H heteroarylation in the presence of alkenes. The benzothiazolylation of (−)-ambroxide afforded 15 in 45% isolated yield as a single diastereomer, highlighting the potential for stereoselective C—H functionalization using the present strategy; alternative LSFs of this substrate by us and others were not stereoselective. (74, 81, 85) This feature was further demonstrated by C—H heteroarylation of the sesquiterpene cedryl acetate, which produced 16 in good yield (55%) as single diastereomers favoring the most accessible methylene site (2.7:1 rr). Common substrate (+)-sclareolide was functionalized with substrate as limiting reagent to afford 17 in 71% isolated yield. In contrast, prior C—H heteroarylation of this substrate using nickel/polyoxometalate dual-catalysis required the use of (+)-sclareolide in excess (5 equiv). (76) As a final demonstration of the capabilities of the C—H heteroarylation in LSF, trans-androsterone acetate was derivatized in 44% yield favoring the $C_6$ position on the B-ring (2.5:1 rr) with high stereoselectivity.

Exemplary heteroaryl coupling partners in the transformation are shown in the table above. In addition to benzothiazole, both benzoxazole and benzimidazole sulfones 19 and 20 were good coupling partners, generating C—H heteroarylation products of (+)-sclareolide in good yield. 1,2-Azoles also reacted efficiently, as 2-(phenylsulfonyl) thiazole participated in the LSF in 53% yield. The LSFs transferring either a pyrimidine or oxadiazole heterocycle were also successful using partners 22 or 23, respectively.

Experiments were performed by exploring the heteroaryl scope with either N-Boc piperidine or N-Boc morpholine as substrate owing to difficulties in product isolation using (+)-sclareolide as substrate in these examples. Reactions using 2-(phenylsulfonyl) oxazole (24) and 2-(phenylsulfonyl)pyrimidine (25) both proceeded in good yield. Notably, both transformations involving pyrimidine substrates (22 and 25) proceeded with complete regioselectivity for the 2-position; Minisci-type C—H functionalizations using pyrimidines are known to produce regioisomeric mixtures. (84) Attempts to extend the heteroarene scope to pyridines were initially unsuccessful, as reactions using either 2-(methylsulfonyl)- or 2-(phenylsulfonyl)-pyridine proceeded in low yields (<15%). Potentially, the use of a more electron-deficient pyridine could facilitate alkyl radical addition and heterocycle transfer. Heteroarylation with 2-(methylsulfonyl)-6-trifluoromethylpyridine (26) was indeed more efficient (42% yield). Finally, both 2- and 4-(methylsulfonyl) quinolines 27 and 28 delivered the desired C—H heteroarylation products in moderate yields. Importantly, in both cases the reactions were completely regioselective for the sulfonylated position of the heterocycle. Minisci-type heteroarylations using quinolines typically produce regioisomeric mixtures or dialkylation products, unless one of the sites is substituted. (85)

Example 15: Heteroarylation of C—H Bonds for Late-Stage Functionalization

Reactions were completed as depicted in Schemes 66 and 67.

Scheme 66

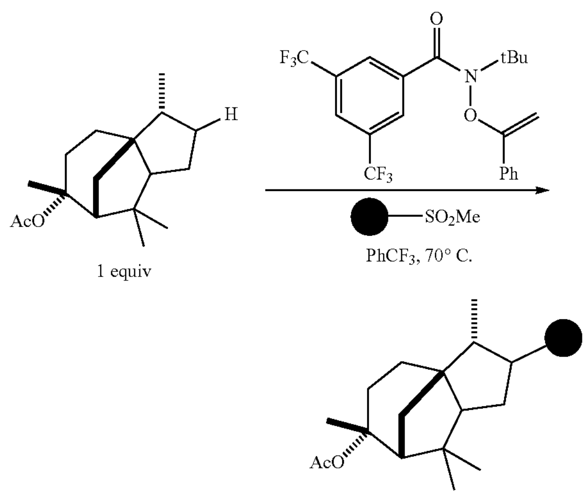

Scheme 67

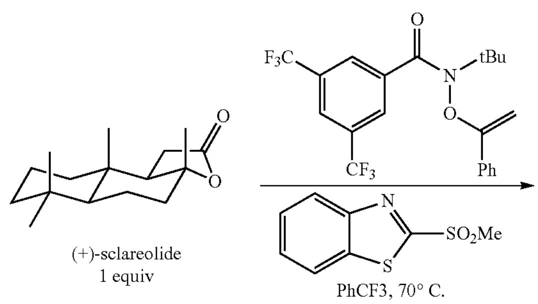

(+)-sclareolide
1 equiv

-continued

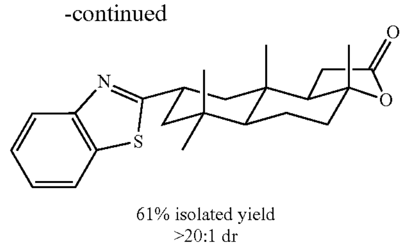

61% isolated yield
>20:1 dr

Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

BIBLIOGRAPHY

1. J. F. Hartwig, Evolution of C—H Bond Functionalization from Methane to Methodology. *J. Am. Chem. Soc.* 138, 2-24 (2016).
2. H. M. L. Davies, Finding Opportunities from Surprises and Failures. Development of Rhodium-Stabilized Donor/Acceptor Carbenes and Their Application to Catalyst-Controlled C—H Functionalization. *J. Org. Chem.* 84, 12722-12745 (2019).
3. M. C. White, Adding Aliphatic C—H Bond Oxidations to Synthesis. *Science* 335, 807-809 (2012).
4. B. Hong, T. Luo, X. Lei, Late-Stage Diversification of Natural Products. *ACS Cent. Sci.* 6, 622-635 (2020).
5. T. Cernak, K. D. Dykstra, S. Tyagarajan, P. Vachal, S. W. Krska, The medicinal chemist's toolbox for late stage functionalization of drug-like molecules. *Chem. Soc. Rev.* 45, 546-576 (2016).
6. D. E. MacArthur, D. Waughray, M. R. Stuchtey, The New Plastics Economy Rethinking the Future of Plastics. *World Economic Forum* (2016).
7. J. B. Williamson, S. E. Lewis, R. R. Johnson, I. M. Manning, F. A. Leibfarth, F. A. C—H Functionalization of Commodity Polymers. *Angew. Chem. Int. Ed.* 58, 8654-8668 (2019).
8. P. F. Britt, G. W. Coates, K. I. Winey, Basic Energy Sciences Roundtable: Chemical Upcycling of Polymers. *Office of Science and Technical Information* (2019).
9. Q. An, Z. Wang, Y. Chen, X. Wang, K. Zhang, H. Pan, W. Liu, Z. Zuo, Cerium-Catalyzed C—H Functionalizations of Alkanes Utilizing Alcohols as Hydrogen Atom Transfer Agents. *J. Am. Chem. Soc.* 142, 6216-6226 (2020).
10. N. K. Boaen, M. A. Hillmyer, Post-polymerization functionalization of polyolefins. *Chem. Soc. Rev.* 34, 267-275 (2005).
11. D. C. Blakemore, L. Castro, I. Churcher, D. C. Rees, A. W. Thomas, D. M. Wilson, A. Wood, Organic synthesis provides opportunities to transform drug discovery. *Nature Chemistry* 10, 383-394 (2018).
12. D. Ravelli, M. Fagnoni, T. Fukuyama, T. Nishikawa, I. Ryu, Site-Selective C—H Functionalization by Decatungstate Anion Photocatalysis: Synergistic Control by Polar and Steric Effects Expands the Reaction Scope. *ACS Catal.* 8, 701-713 (2018).
13. M. C. White, J. Zhao, Aliphatic C—H Oxidations for Late-Stage Functionalization. *J. Am. Chem. Soc.* 140, 13988-14009 (2018).
14. K. Liao, Y.-F. Yang, Y. Li, J. N. Sanders, K. N. Houk, D. G. Musaev, H. M. L. Davies, Design of catalysts for site-selective and enantioselective functionalization of non-activated primary C—H bonds. *Nature Chem.* 10, 1048-1055 (2018)
15. V. A. Schmidt, R. K. Quinn, A. T. Brusoe, E. J. Alexanian, Site-Selective Aliphatic C—H Bromination Using N-Bromoamides and Visible Light. *J. Am. Chem. Soc.* 136, 14389-14392 (2014).
16. R. K. Quinn, Z. A. Könst, S. E. Michalak, Y. Schmidt, A. R. Szklarski, A. R. Flores, S. Nam, D. A. Horne, C. D. Vanderwal, E. J. Alexanian, Site-Selective Aliphatic C—H Chlorination Using N-Chloroamides Enables a Synthesis of Chlorolissoclimide. *J. Am. Chem. Soc.* 138, 696-702 (2016).
17. W. L. Czaplyski, C. G. Na, E. J. Alexanian, C—H Xanthylation: A Synthetic Platform for Alkane Functionalization. *J. Am. Chem. Soc.* 138, 13854-13857 (2016).
18. C. M. Plummer, H. Zhou, W. Zhu, H. Huang, L. Liu, Y. Chen, Mild halogenation of polyolefins using an N-haloamide reagent. *Polym. Chem.* 9, 1309-1317 (2018).
19. J. B. Williamson, W. L. Czaplyski, E. J. Alexanian, F. A. Leibfarth, Regioselective C—H Xanthylation as a Platform for Polyolefin Functionalization. *Angew. Chem. Int. Ed.* 57, 6261-6265 (2018).

20. J. B. Williamson, C. G. Na, R. R. Johnson, W. F. M. Daniel, E. J. Alexanian, F. A. Leibfarth, Chemo- and Regioselective Functionalization of Isotactic Polypropylene: A Mechanistic and Structure-Property Study. *J. Am. Chem. Soc.* 141, 12815-12823 (2019).
21. A. Artaryan, A. Mardyukov, K. Kulbitski, I. Avigdori, G. A. Nisnevich, P. R. Schreiner, M. Gandelman, Aliphatic C—H Bond Iodination by a N-Iodoamide and Isolation of an Elusive N-Amidyl Radical. *J. Org. Chem.* 82, 7093-7100 (2017).
22. C. R. Pitts, S. Bloom, R. Woltornist, D. J. Auvenshine, L. R. Ryzhkov, M. A. Siegler, T. Lectka, Direct, Catalytic Monofluorination of $sp^3$ C—H Bonds: A Radical-Based Mechanism with Ionic Selectivity. *J. Am. Chem. Soc.* 136, 9780-9791 (2014).
23. K. A. Margrey, W. L. Czaplyski, D. A. Nicewicz, E. J. Alexanian, A General Strategy for Aliphatic C—H Functionalization Enabled by Organic Photoredox Catalysis. *J. Am. Chem. Soc.* 140, 4213-4217 (2018).
24. R. D. Chambers, T. Nakano, M. Parsons, G. Sandford, A. S. Batsanov, J. A. K. Howard, Elemental fluorine Part 22. Fluorination of 3b-acetoxy-5a-androstan-17-one using fluorine and Selectfluor. *J. Fluorine Chem.* 811-816 (2008).
25. A. Rahimi, J. M. Garcia. Chemical recycling of waste plastics for new materials production. *Nat. Rev. Chem.* 1, 1-11 (2017).
26. A. E. Hamielec, P. E. Gloor, S. Zhu, Kinetics of, free radical modification of polyolefins in extruders—chain scission, crosslinking and grafting. *Can. J. Chem. Eng.* 69, 611-618 (1991).
27. M. Häußler, M. Eck, D. Rothauer, S. Mecking, Closed-loop recycling of polyethylene-like materials. *Nature,* 590, 423-427 (2021).
28. D. Liu, C. W. Bielawski, Direct azidation of isotactic polypropylene and synthesis of 'grafted to' derivatives thereof using azide-alkyne cycloaddition chemistry. *Polym. Int.* 66, 70-76 (2017).
29. C. M. Plummer, L. Li, Y. Chen, The post-modification of polyolefins with emerging synthetic methods. *Polym. Chem.* 11, 6862-6872 (2020).
30. H. Schönherr, T. Cernak, Profound Methyl Effects in Drug Discovery and a Call for New C—H Methylation Reactions. *Angew. Chem. Int. Ed.* 52, 12256-12267 (2013).
31. K. Feng, R. E. Quevedo, J. T. Kohrt, M. S. Oderinde, U. Reilly, M. C. White, Late-stage oxidative C(sp3)-H methylation. *Nature* 580, 621-627 (2020).
32. I. B. Perry, T. F. Brewer, P. J. Sarver, D. M. Schultz, D. A. DiRocco, D. W. C. MacMillan, Direct arylation of strong aliphatic C—H bonds. *Nature* 560, 70-75 (2018).
33. R. Oeschger, B. Su, I. Yu, C. Ehinger, E. Romero, S. He, J. Hartwig, Diverse functionalization of strong alkyl C—H bonds by undirected borylation. *Science* 368, 736-741 (2020).
34. C. Shu, A. Noble, V. K. Aggarwal, Metal-free photoinduced C(sp3)-H borylation of alkanes. *Nature* 586, 714-719 (2020).
35. Y. Cheng, C. Mück-Lichtenfeld, A. Studer, Metal-Free Radical Borylation of Alkyl and Aryl Iodides. *Angew. Chem. Int. Ed.* 57, 16832-16836 (2018).
36. C. D. Matier, J. Schwaben, J. C. Peters, G. C. Fu, Copper-Catalyzed Alkylation of Aliphatic Amines Induced by Visible Light. *J. Am. Chem. Soc.* 139, 17707-17710 (2017).
37. R. R. Merchant, J. T. Edwards, T. Qin, M. M. Kruszyk, C. Bi, G. Che, D.-H. Bao, W. Qiao, L. Sun, M. R. Collins, O. O. Fadeyi, G. M. Gallego, J. J. Mousseau, P. Nuhant, P. S. Baran, Modular radical cross-coupling with sulfones enables access to $sp^3$-rich (fluoro)alkylated scaffolds. *Science* 360, 75-80 (2018).
38. M. M. Tierney, S. Crespi, D. Ravelli, E. J. Alexanian, Identifying Amidyl Radicals for Intermolecular C—H Functionalizations. *J. Org. Chem.* 84, 12983-12991 (2019).
39. B. P. Grady, Review and critical analysis of the morphology of random ionomers across many length scales. *Polym. Eng. Sci.* 48, 1029-1051 (2008).
40. C. Vadenbo, S. Hellweg, T. F. Astrup, Let's Be Clear (er) about Substitution: A Reporting Framework to Account for Product Displacement in Life Cycle Assessment. *J. Ind. Ecol.* 21, 1078-1089 (2017).
41. P. F. Alewood; I. C. Calder; R. L. Richardson. An Improved Preparation of N-(t-Butyl)-N-(3,5-Dinitrobenzoyl)-Nitroxyl. *Synthesis* 1981, 2, 121-122.
42. Piou, T.; Rovis, T. $R^h$(III)-Catalyzed Cyclopropanation Initiated by C—H Activation: Ligand Development Enables a Diastereoselective [2+1] Annulation of N-Enoxyphthalimides and Alkenes. *J. Am. Chem. Soc.* 2014, 136, 11292-11295.
43. Meyer, D.; Jangra, H.; Walther, F.; et al. A Third Generation of Radical Fluorinating Agents Based on N-Fluoro-N-Arylsulfonamides. *Nat Commun* 2018, 9, 1-10.
44. Chavez-Flores, D.; Salvador, J. M. Facile Conversion of Racemic Ibuprofen to (S)-Ibuprofen. *Tetrahedron: Asymmetry* 2012, 23, 237-239.
45. Koch, V.; Bräse, S. Pd-Mediated Cross-Coupling of C-17 Lithiated Androst-16-En-3-01 Access to Functionalized Arylated Steroid Derivatives. *Org. Biomol. Chem.* 2017, 15, 92-95.
46. Fredo Naciuk, F.; do Nascimento Faria, J.; Gonçalves Eufrásio, A.; et al. Development of Selective Steroid Inhibitors for the Glucose-6-Phosphate Dehydrogenase from *Trypanosoma Cruzi. ACS Med. Chem. Lett.* 2020, 11, 1250-1256.
47. Li, H.; Shan, C.; Tung, C.-H.; et al. Dual Gold and Photoredox Catalysis: Visible Light-Mediated Intermolecular Atom Transfer Thiosulfonylation of Alkenes. *Chem. Sci.* 2017, 8, 2610-2615.
48. Meyer, D.; Renaud, P. Enantioselective Hydroazidation of Trisubstituted Non-Activated Alkenes. *Angewandte Chemie International Edition* 2017, 56, 10858-10861.
49. Anthore, L.; Zard, S. Z. A Convergent Radical Based Route to Trifluoromethyl Ketones and to α,β-Unsaturated Trifluoromethyl Ketones. *Org. Lett.* 2015, 17, 3058-3061.
50. Li, X.; Liu, L.; Liu, G.; et al. Efficient Dye-Sensitized Solar Cells with Potential-Tunable Organic Sulfide Mediators and Graphene-Modified Carbon Counter Electrodes. *Advanced Functional Materials* 2013, 23, 3344-3352.
51. K. Yadav, A.; P. Srivastava, V.; S. Yadav, L. D. An Easy Access to Fluoroalkanes by Deoxygenative Hydrofluorination of Carbonyl Compounds via Their Tosylhydrazones. *Chemical Communications* 2013, 49, 2154-2156.
52. Kennedy, N.; Liu, P.; Cohen, T. Fundamental Difference in Reductive Lithiations with Preformed Radical Anions versus Catalytic Aromatic Electron-Transfer Agents: N,N-Dimethylaniline as an Advantageous Catalyst. *Angewandte Chemie International Edition* 2016, 55, 383-386.
53. Van Oystaeyen, A.; Oliveira, R. C.; Holman, L.; et al. Conserved Class of Queen Pheromones Stops Social Insect Workers from Reproducing. *Science* 2014, 343, 287-290.

54. Bérubé, Sm.; Kamal, F.; Roy, J.; et al. A Dehydrohalogenation Methodology for Synthesizing Terminal Olefins under Mild Conditions. *Synthesis* 2006, 3085-3091.

55. Levy, L. M.; de Gonzalo, G.; Gotor, V. Resolution of N-Protected Cis- and Trans-3-Aminocyclohexanols via Lipase-Catalyzed Enantioselective Acylation in Organic Media. *Tetrahedron: Asymmetry* 2004, 2051-2056.

56. Zeng, C.; Shen, G.; Yang, F.; et al. *Rhodium-Catalyzed Generation of Anhydrous* Hydrogen Iodide: An Effective Method for the Preparation of Iodoalkanes. *Org. Lett.* 2018, 20, 6859-6862.

57. Wu, H.; Xiao, Z.; Wu, J.; et al. Direct Trifluoromethylthiolation of Unactivated C(Sp3)-H Using Silver(I) Trifluoromethanethiolate and Potassium Persulfate. *Angewandte Chemie International Edition* 2015, 54, 4070-4074.

58. Kamijo, S.; Watanabe, M.; Kamijo, K.; et al. Synthesis of Aliphatic Azides by Photoinduced C(Sp3)-H Azidation. *Synthesis* 2016, 115-121.

59. Kamijo, S.; Hoshikawa, T.; Inoue, M. Photochemically Induced Radical Transformation of $C(Sp^3)$—H Bonds to $C(Sp^3)$ CN Bonds. *Organic Letters* 2011, 13, 5928-5931.

60. Kropp, P. J.; Adkins, R. L. Photochemistry of Alkyl Halides. 12. Bromides vs. Iodides. *J. Am. Chem. Soc.* 1991, 113, 2709-2717.

61. Chambers, R. D.; Kenwright, A. M.; Parsons, M.; et al. *Elemental Fluorine. Part* 14.1 Electrophilic Fluorination and Nitrogen Functionalisation of Hydrocarbons. *J. Chem. Soc., Perkin Trans.* 1 2002, 2190-2197.

62. Huang, X.; Bergsten, T. M.; Groves, J. T. Manganese-Catalyzed Late-Stage Aliphatic C—H Azidation. *Journal of the American Chemical Society* 2015, 137, 5300-5303.

63. Halperin, S. D.; Fan, H.; Chang, S.; et al. A Convenient Photocatalytic Fluorination of Unactivated C—H Bonds. *Angewandte Chemie International Edition* 2014, 53, 4690-4693.

64. Larkina, M. S.; Ozerskaya, A. V.; Podrezova, E. V.; et al. Efficient Synthesis of ω-[18F]Fluoroaliphatic Carboxylic Esters and Acids for Positron Emission Tomography. *European Journal of Organic Chemistry* 2020, 2020, 6375-6381.

65. Nielsen, M. K.; Ahneman, D. T.; Riera, O.; et al. Deoxyfluorination with Sulfonyl Fluorides: Navigating Reaction Space with Machine Learning. *J. Am. Chem. Soc.* 2018, 140, 5004-5008.

66. Hua, A. M.; Mai, D. N.; Martinez, R.; et al. Radical C—H Fluorination Using Unprotected Amino Acids as Radical Precursors. *Org. Lett.* 2017, 19, 2949-2952.

67. Xu, W.; Wang, W.; Liu, T.; et al. Late-Stage Trifluoromethylthiolation of Benzylic C—H Bonds. *Nat Commun* 2019, 10, 1-8.

68. Wang, Y.; Ji, S.; Wei, K.; et al. Epiandrosterone-Derived Prolinamide as an Efficient Asymmetric Catalyst for Michael Addition Reactions of Aldehydes to Nitroalkenes. *RSC Adv.* 2014, 4, 30850-30856.

69. Liu, W.; Huang, X.; Cheng, M.-J.; et al. Oxidative Aliphatic C—H Fluorination with Fluoride Ion Catalyzed by a Manganese Porphyrin. *Science* 2012, 337, 1322-1325.

70. Toda, N.; Asano, S.; Barbas, C. F. Rapid, Stable, Chemoselective Labeling of Thiols with Julia-Kocieński-like Reagents: A Serum-Stable Alternative to Maleimide-Based Protein Conjugation. *Angewandte Chemie International Edition* 2013, 52, 12592-12596.

71. Köhler, F.; Gais, H.-J.; Raabe, G. Asymmetric Synthesis of Highly Substituted γ-Amino Acids from Allyltitanium Sulfoximines. *Org. Lett.* 2007, 9, 1231-1234.

72. Nakamura, M.; Matsuo, K.; Ito, S.; et al. Iron-Catalyzed Cross-Coupling of Primary and Secondary Alkyl Halides with Aryl Grignard Reagents. *J. Am. Chem. Soc.* 2004, 126, 3686-3687.

73. Reiss, T.; Breit, B. Total Synthesis of (+)-Bourgeanic Acid Utilizing o-DPPB-Directed Allylic Substitution. *Org. Lett.* 2009, 11, 3286-3289.

74. (a) Schmidt, V. A.; Quinn, K. R.; Brusoe, A. T; Alexanian, E. J; *J. Am. Chem. Soc.* 2014, 136, 14389. (b) Quinn, K. R.; Konst, Z.; Michalak, S.; Schmidt, Y.; Szklarksi, A.; Flores, Z.; Nam, S.; Horne, D.; Vanderwal, C.; Alexanian, E. *J. J. Am. Chem. Soc.* 2016, 138, 696. (c) Czaplyski, W. L.; Na, C. G.; Alexanian, E. J.; *J. Am. Chem. Soc.* 2016, 138, 13854-13857. (d) Williamson, J. B.; Czaplyski, V. L.; Alexanian, E. J.; Leibfarth, F. A.; *Angew. Chem. Int. Ed.* 2018, 57, 6261. (e) Carestia, A. M.; Alexanian, E. J.; *Chem. Sci.* 2018, 9, 5360.

75. Jana, R.; Pathak, T. P.; Sigman, M. S. *Chem. Rev.* 2011, 111, 1417. (b) Tasker, S. Z.; Standley, E. A.; Jamison, T. F. *Nature* 2014, 509, 299. (c) Zuo, Z.; MacMillan, D. W. C. *J. Am. Chem. Soc.* 2014, 136, 5257. (d) Lo, J. C.; Gui, J.; Yabe, Y.; Pan, C. M.; Baran, P. S. *Nature* 2014, 516, 343.

76. Perry, I. B.; Brewer, T. F.; Sarver, P. J.; Schultz, D. M.; DiRocco, MacMillan, D. W. C. *Nature* 2018, 560, 70.

77. (a) Dong, J.; Xia, Q.; Lv, X.; Yan, C.; Song, H.; Liu, Y.; Wang, Q. *Org. Lett.* 2018, 20, 5661. (b) Hao, H—Y.; Mao, Y-J.; Xu, Z—Y.; Lou, S-J.; Xu, D-Q.; *Org. Lett.* 2020, 22, 2396.

78. (a) Jin, J.; MacMillan, D. W. C. *Angew. Chem. Int. Ed.* 2014, 54, 1565. (b) Shao, X.; Wu, X.; Wu, S.; Zhu, C.; *Org. Lett.* 2020, 22, 7450. (c) Cheng, W.-M.; Shang, R.; Fu, Y. *ACS Catal.* 2017, 7, 907.

79. (a) Ikedi, Y.; Matsukawa, Y.; Yonekura, K.; Shirikawa, E.; *Eur. J. Org. Chem.* 2021, 794. (b) Kamijo, S.; Kamijo, K.; Murafuji, T. *J. Org. Chem.* 2017, 82, 2664. (c) Fan, X—Z.; Rong, J-W.; Wu, H-L.; Zhou, Q.; Deng, H—P.; Tan, J. D.; Xue, C—W.; Wu, L-Z.; Tao, H—R.; Wu, *J. Angew. Chem. Int. Ed.* 2018, 57, 8514. (d) Lipp, A.; Lahm, G.; Opatz, T. *J. Org. Chem.* 2016, 4890.

80. For reviews, see: Proctor, R. S. J.; Phipps, R. *J. Angew. Chem. Int. Ed.* 2019, 58, 13666. For representative examples, see: (a) Bissonnette, N. B.; Boyd, M. J.; May, G. D.; Giroux, S.; Nuhant, P. *J. Org. Chem.* 2018, 83, 10933. (b) Liu. P.; Liu, W.; Li, C.-J. *J. Am. Chem. Soc.* 2017, 139, 14315. (c) Wu. X.; See, J. W. T.; Xu, K.; Hirao, H.; Roger, J.; Hierso, J.; Zhou, S. *Angew. Chem. Int. Ed.* 2014, 53, 13573.

81. Fazekas, T. J.; Alty, W. J.; Neidhart, E. Z.; Miller, A. S.; Leibfarth, F. A.; Alexanian, E. *J. Science* 2022, 375, 545.

82. Daly, J. W.; Garrafo, H. M.; Spande, T. F.; Decker, M. W.; Sullivan, J. P.; William, M. *Nat. Prod. Rep.* 2000, 17, 131.

83. (a) Feng, K.; Quevedo, R. E.; Kohrt, J. T.; Oderinde, M. S.; Reilly, U.; White, M. C. *Nature* 2020, 580, 621. (b) Chandra, B.; Singh, K. K.; Gupta, S. S. *Chem. Sci.* 2017, 8, 7545.

84. Li, G.-X.; Morales-Rivera, C. A.; Wang, Y.; Gao, F.; He, G.; Liu, P.; Chen, G. *Chem. Sci.* 2016, 7, 6407.

85. Dong, J.; Lyu, X.; Wang, Z.; Wang, X.; Song, H.; Liu, Y.; Wang, Q. *Chem. Sci.* 2019, 10, 976.

That which is claimed:

1. A compound of Formula I:

I

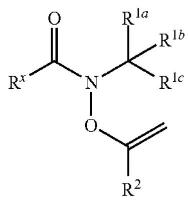

wherein, $R^X$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl, —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted; and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$.

2. The compound of claim 1, wherein $R^{1a}$, $R^{1b}$ and $R^{1c}$ are each independently selected from the group consisting of $C_{3-8}$ cycloalkyl, $C_{2-8}$ heterocyclyl, linear or branched $C_{1-6}$ alkyl, —CN, and —C(═O)-Q-$R^{10a}$.

3. The compound of claim 1, wherein each of $R^{1a}$, $R^{1b}$ and $R^{1c}$ is methyl.

4. A compound of Formula II:

II

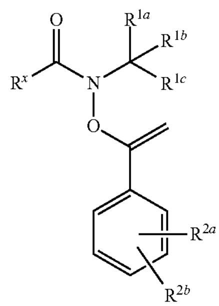

wherein, $R^X$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl, —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

only one or two of $R^{1a}$, $R^{1b}$ and $R^{1c}$ can be hydrogen;

$R^{2a}$ and $R^{2b}$ are each independently selected from the group consisting of hydrogen, halo, optionally substituted linear or branched $C_{1-10}$ alkyl, —CN, $C_{1-6}$ alkoxy, —$NO_2$, —$NR^aR^b$, —(C═O)$OR^c$ and —(C═O)$R^c$, wherein, $R^a$, $R^b$ and $R^c$ are each independently selected from the group consisting of hydrogen, methyl, ethyl, propyl and butyl.

5. The compound of claim 4, wherein $R^{2a}$ and $R^{2b}$ are each hydrogen.

6. The compound of claim 1, wherein $R^x$ is selected from the group consisting of —$CF_3$, methyl, t-butyl and optionally substituted phenyl.

7. The compound of claim 6, wherein the optionally substituted phenyl has the structure:

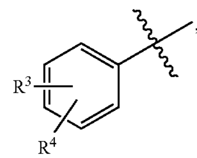

wherein, $R^3$ and $R^4$ are each independently selected from the group consisting of halo-$C_{1-6}$ alkyl, halo, —CN, and —$NO_2$.

8. The compound of claim 7, wherein at least one of $R^3$ and $R^4$ is halo-$C_{1-6}$ alkyl.

9. The compound of claim 7, wherein $R^3$ is selected from the group consisting of F, Cl, —$CF_3$, —$CHF_2$ and $CH_2F$; and $R^4$ is independently selected from the group consisting of F, Cl, —$CF_3$, —$CHF_2$ and $CH_2F$.

10. The compound of claim 1, having a structure of Formula III:

III

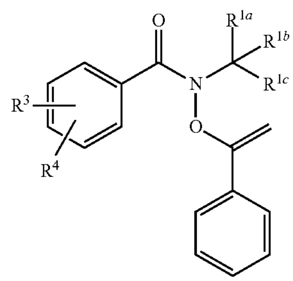

wherein, $R^3$ and $R^4$ are each independently selected from the group consisting of halo-$C_{1-6}$ alkyl, halo, —CN, and —$NO_2$.

11. The compound of claim 10, wherein $R^3$ is selected from the group consisting of F, Cl, —$CF_3$, —$CHF_2$ and $CH_2F$; and $R^4$ is independently selected from the group consisting of F, Cl, —$CF_3$, —$CHF_2$ and $CH_2F$.

12. The compound of claim 1, having the structure:

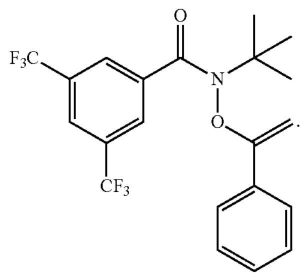 [SMILES: C=C(ON(C(=O)c1cc(C(F)(F)F)cc(C(F)(F)F)c1)C(C)(C)C)c1ccccc1]

13. A mixture comprising:

a solvent;

a compound of Formula I:

I

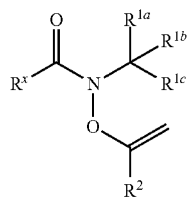

wherein, $R^X$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of hydrogen, $C_{2-8}$ alkenyl, $C_{2-8}$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl, —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted; and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$ and, at least one of the following:

i. a compound of Formula T-A:

T-A

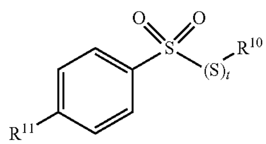

wherein, $R^{11}$ is selected from the group consisting of hydrogen, halo, halo-$C_{1-6}$ alkyl, —CN, $C_{1-6}$ alkyl and $C_{1-6}$ alkoxy;

f is 0 or 1;

$R^{10}$, when f is 1, is selected from the group consisting of halo-$C_{1-6}$ alkyl, and optionally substituted $C_{6-10}$ aryl; or $R^{10}$, when f is 0, is selected from the group consisting of —CN and —$N_3$;

or, i(a) a compound of Formula T-A1:

T-A1

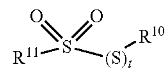

wherein, $R^T$ is selected from the group consisting of $C_{1-6}$ alkyl and $C_{6-10}$ aryl, wherein the $C_{6-10}$ aryl is optionally substituted with $R^{11}$;

$R^{11}$ is selected from the group consisting of hydrogen, phenyl, halo, —C(O)O—$C_{1-6}$ alkyl, halo-$C_{1-6}$ alkyl, —CN, $C_{1-6}$ alkyl and $C_{1-6}$ alkoxy;

f is 0 or 1;

$R^{10}$ is a moiety that along with —$(S)_f$— is an X moiety for transferring and binding to a carbon on a substrate;

or, ii. an external trap selected from the group consisting of

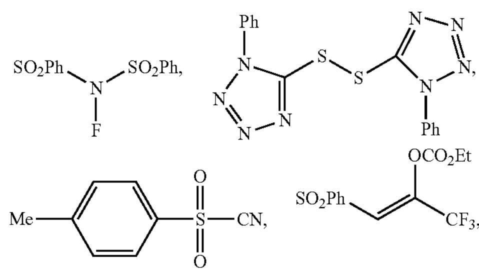

$PhO_2S$—$SCF_3$, $PhO_2S$—SPh, $PhO_2S$—$N_3$, $Cl_3C$—Cl, $Cl_3C$—Br, $F_{13}C_6$—I, $F_{17}C_8$—Br, and $F_{17}C_8$—I.

14. A method of functionalizing a substrate, comprising:

i. in the presence of a radical trap comprising a transfer group X and the substrate, wherein the substrate comprises a C—H bond, allowing a compound of Formula I:

I

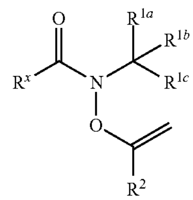

wherein, $R^X$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alky-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl, —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted; and, $R^2$ is a $C_{6-10}$ aryl, wherein the aryl can be optionally substituted one to five times with a substituent selected from the group consisting of $C_{1-6}$ alkyl, halo-$C_{1-6}$ alkyl, halo, —CN, and —$NO_2$;

to contact an initiator to form a nitrogen-centered radical;

ii. allowing the substrate comprising a C—H bond to contact the nitrogen-centered radical to form a substrate radical;

iii. allowing the substrate radical to contact the radical trap comprising a transfer group X, wherein, a C—H bond in the substrate is functionalized to a covalent C—X bond, wherein X is the transfer group; and, wherein the radical trap comprising a transfer group X is selected from the group consisting of:

T-1

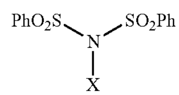

T-3

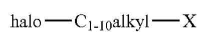

T-4

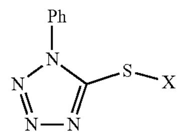

T-5

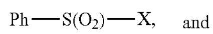

and

T-6

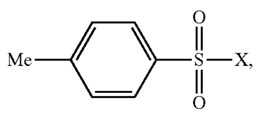

wherein X is selected from the group consisting of —S—$C_{3-8}$ heteroaryl which can be optionally substituted, —$C_{3-8}$ heteroaryl which can be optionally substituted, halogen, —S-halo-$C_{1-6}$ alkyl, —S-Ph, —$NO_2$, —CN, and

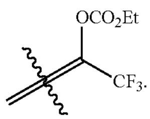

15. The method of claim 14, wherein $R^{1a}$, $R^{1b}$ and $R^{1c}$ are each independently selected from the group consisting of $C_{3-8}$ cycloalkyl, $C_{2-8}$ heterocyclyl, linear or branched $C_{1-6}$ alkyl, —CN, and —C(═O)-Q-$R^{10a}$.

16. The method of claim 15, wherein at least one of $R^{1a}$, $R^{1b}$ and $R^{1c}$ is a linear or branched $C_{1-6}$ alkyl.

17. The method of claim 16, wherein each of $R^{1a}$, $R^{1b}$ and $R^{1c}$ is methyl.

18. A method of functionalizing a substrate, comprising:

i. in the presence of a radical trap comprising a transfer group X and the substrate, wherein the substrate comprises a C—H bond, allowing a compound of Formula II:

II

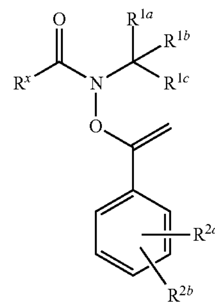

wherein, $R^X$ is an optionally substituted linear or branched $C_{1-10}$ alkyl or optionally substituted $C_{6-10}$ aryl;

$R^{1a}$, $R^{1b}$ and $R^{1c}$ are each independently selected from the group consisting of hydrogen, $C_2$-$C_8$ alkenyl, $C_2$-$C_8$ alkynyl, —$C_1$-$C_3$ alkyl-$C_1$-$C_3$ alkoxy-, $C_{3-8}$ cycloalkyl, $C_{6-10}$ aryl, $C_{3-8}$ heteroaryl, $C_{2-8}$ heterocyclyl, —$C_1$-$C_3$ alkyl-$C_{3-8}$ cycloalkyl, —$C_1$-$C_3$ alkyl-$C_{6-10}$ aryl, —$C_1$-$C_3$ alkyl-$C_{3-8}$ heteroaryl, —$C_1$-$C_3$ alkyl-$C_{2-8}$ heterocyclyl, linear or branched $C_{1-6}$ alkyl, hydroxy-$C_1$-$C_6$-alkyl —CN, and —C(═O)-Q-$R^{10a}$, wherein, Q is O or is absent;

$R^{10a}$ is hydrogen or $C_{1-6}$ alkyl; and wherein, the cycloalkyl, aryl, heteroaryl, heterocyclyl and alkyl can each be independently optionally substituted;

only one or two of $R^{1a}$, $R^{1b}$ and $R^{1c}$ can be hydrogen;

$R^{2a}$ and $R^{2b}$ are each independently selected from the group consisting of hydrogen, halo, optionally substituted linear or branched $C_{1-10}$ alkyl, —CN, $C_{1-6}$ alkoxy, —$NO_2$, —$NR^aR^b$, —(C═O)$OR^c$ and —(C═O)$R^c$, wherein, $R^a$, $R^b$ and $R^c$ are each independently selected from the group consisting of hydrogen, methyl, ethyl, propyl and butyl to contact an initiator to form a nitrogen-centered radical;

ii. allowing the substrate comprising a C—H bond to contact the nitrogen-centered radical to form a substrate radical;

iii. allowing the substrate radical to contact the radical trap comprising a transfer group X, wherein, a C—H bond in the substrate is functionalized to a covalent C—X bond, wherein X is the transfer group; and, wherein the radical trap comprising a transfer group X is selected from the group consisting of:

T-1

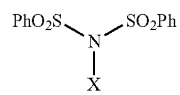

T-3

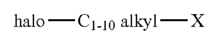

T-4

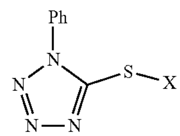

-continued

T-5

$Ph—S(O_2)—X$, and

T-6

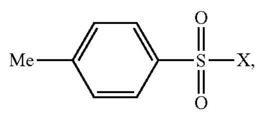

wherein X is selected from the group consisting of —S—$C_{3-8}$ heteroaryl which can be optionally substituted, —$C_{3-8}$ heteroaryl which can be optionally substituted, halogen, —S-halo-$C_{1-6}$ alkyl, —S-Ph, —$NO_2$, —CN, and

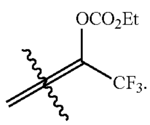

19. The method of claim 14, wherein the compound is a structure of Formula III:

III

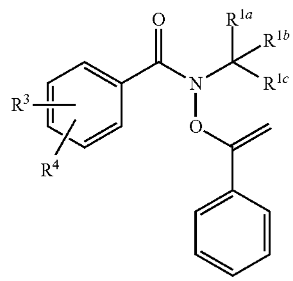

wherein, $R^3$ and $R^4$ are each independently selected from the group consisting of halo-$C_{1-6}$ alkyl, halo, —CN, and —$NO_2$.

* * * * *